(12) United States Patent
Melamed et al.

(10) Patent No.: US 7,899,702 B2
(45) Date of Patent: Mar. 1, 2011

(54) SYSTEM AND METHOD FOR FACILITATING GENERATION AND PERFORMANCE OF ON-LINE EVALUATIONS

(76) Inventors: David P. Melamed, New York, NY (US); Morris Nejat, Short Hills, NJ (US)

( * ) Notice: Subject to any disclaimer, the term of this patent is extended or adjusted under 35 U.S.C. 154(b) by 492 days.

(21) Appl. No.: 11/933,979

(22) Filed: Nov. 1, 2007

(65) Prior Publication Data
US 2008/0126172 A1 May 29, 2008

Related U.S. Application Data

(63) Continuation of application No. 10/106,933, filed on Mar. 25, 2002, now abandoned.

(60) Provisional application No. 60/278,299, filed on Mar. 23, 2001.

(51) Int. Cl.
G06Q 10/00 (2006.01)
(52) U.S. Cl. ..................................................... 705/10
(58) Field of Classification Search .................... 705/10
See application file for complete search history.

(56) References Cited

U.S. PATENT DOCUMENTS

| | | | | |
|---|---|---|---|---|
| 5,692,125 | A * | 11/1997 | Schloss et al. ................. | 705/9 |
| 6,014,760 | A * | 1/2000 | Silva et al. .................... | 714/46 |
| 6,157,808 | A * | 12/2000 | Hollingsworth ............. | 434/350 |
| 6,175,833 | B1 * | 1/2001 | West et al. .................. | 707/102 |
| 6,311,190 | B1 * | 10/2001 | Bayer et al. .............. | 707/104.1 |
| 6,513,042 | B1 * | 1/2003 | Anderson et al. ........... | 707/102 |
| 6,618,734 | B1 * | 9/2003 | Williams et al. ......... | 707/104.1 |
| 6,652,283 | B1 * | 11/2003 | Van Schaack et al. ........ | 434/236 |
| 6,678,355 | B2 * | 1/2004 | Eringis et al. ................. | 379/22 |
| 6,773,266 | B1 * | 8/2004 | Dornbush et al. ........... | 434/322 |
| 2002/0055089 | A1 * | 5/2002 | Scheirer ..................... | 434/350 |
| 2005/0277099 | A1 * | 12/2005 | Van Schaack et al. ....... | 434/322 |
| 2006/0168233 | A1 * | 7/2006 | Alcorn et al. ............... | 709/226 |

OTHER PUBLICATIONS

Mooney, G.A.; Bligh, J G; CyberIST: A virtual game for medical education, May 1998, Medical Teacher, London; 20, 3, Research Library, p. 212.*

(Continued)

*Primary Examiner*—Jonathan G Sterrett
(74) *Attorney, Agent, or Firm*—One, LLP

(57) ABSTRACT

A system and method for facilitating on-line generation and assignment of evaluations for entities of a particular organization comprising: a web-based server device for generating web-based communications for delivery to web-enabled devices over a communications network, and receiving web-based communications via the network; an evaluation build module for initiating a web-based communication via the server device for receipt by a user device, the communication comprising a first interface for receiving user input to generate a customized evaluation for a particular organization including input for specifying a target audience (evaluator) for the evaluation, specifying a subject (evaluatee) of the evaluation, specifying associated evaluation questions for the target audience, and specifying potential answer choice types to be entered by evaluators when completing the evaluation; and, evaluation assignment module for generating an evaluations assignment interface via a web-based communication for receiving user input to selectively assign and schedule by date and date range the generated evaluations to one or more evaluators for receipt at web-enabled devices, wherein the assigned evaluations are capable of being viewed and completed on-line by the evaluators.

12 Claims, 51 Drawing Sheets

OTHER PUBLICATIONS

Mallon, William K; Kassinove, Andrew; "Mandatory reporting laws and the emergency department", Sep. 1999, Topics in Emergency Medicine, vol. 21, Iss.3, p. 63, 10 pgs., ProQuest ID 44501800.*

Mooney, G.A.; Bligh, J G; Leinster, S J; Some techniques for computer-based assessment in medical education, Nov. 1998, Medical Teacher, 20, 6, Research Library, p. 560.*

Friedman, Charles; "The marvelous medical education machine or how medical education can be 'unstuck' in time", Sep. 2000, Medical Teacher, 22, 5; Research Library, p. 496.*

The U.S. Air Force pilot simulated medical unit: A teaching strategy with multiple applications Richard H Eaves, Amanda J Flagg. Journal of Nursing Education. Thorofare:Mar. 2001. vol. 40, Iss. 3, p. 110 (6 pp.).*

Pedagogical agent research at Carte W Lewis Johnson. AI Magazine. La Canada:Winter 2001. vol. 22, Iss. 4, p. 85 (10 pp.).*

Building a better doctor Gene Murti, Ann Jervie Sefton. Quality Progress. Milwaukee:Jun. 2000. vol. 33, Iss. 6, p. 42-51 (10 pp.).*

Development of a competency based training programme to support multidisciplinary working in a combined biochemistry/haematology laboratory R S Woods, W Longmire, M J Galloway, W S A Smellie. Journal of Clinical Pathology. London:May 2000. vol. 53, Iss. 5, p. 401 (4 pp.).*

Computer-based simulations enhance clinical experience of dietetics interns R Elaine Turner, William D Evers, Olivia Bennett Wood, James D Lehman, Louise W Peck. American Dietetic Association. Journal of the American Dietetic Association. Chicago:Feb. 2000. vol. 100, Iss. 2, p. 183-190 (8 pp.).*

Expert systems as a mindtool to facilitate mental model learning Susan Dale Mason-Mason, Martin A Tessmer. Educational Technology, Research and Development. Washington:2000. vol. 48, Iss. 4, p. 43 (20 pp.).*

Instant feedback in the classroom Bruce Upbin. Forbes. New York:Mar. 22, 1999. vol. 163, Iss. 6, p. 68-72 (3 pp.).*

AMEE medical education guide No. 15: Problem-based learing: A practical guide M H Davis, R M Harden. Medical Teacher. London:Mar. 1999. vol. 21, Iss. 2, p. 130-140 (11 pp.).*

How to write short cases for assessing problem-solving skills L W T Schuwirth, D E Blackmore, E Mom, F Van Wildenberg, et al. Medical Teacher. London:Mar 1999. vol. 21, Iss. 2, p. 144-150 (7 pp.).*

Developments in the use of simulators and multimedia computer systems in medical education M S Gordon, S B Issenberg, J W Mayer, J M Feiner. Medical Teacher. London:Jan. 1999. vol. 21, Iss. 1, p. 32-36 (5 pp.).*

Data and Metadata: Development of a digital curriculum Lars Aabakken, Edvin Bach-Gansmo. Medical Teacher. London: Nov. 2000. vol. 22, Iss. 6; p. 572, 4 pgs.*

* cited by examiner

Figure 5(a)

MyEvaluations.com 90

Main[]Mail[]Voluntary[]Reports[]Evaluations[]Users[]Setup[]Password[]Logoff

Add Resident User Profile

Required fields are in bold type.

| | | | |
|---|---|---|---|
| First Name 93 | 91 | Last Name | 92 |
| Password | (Min. 4 alpha-numeric characters) | User Access Level | User 94 |
| Year First Started 96 | | | |
| Pager | 97 | Phone | 98 |
| E-Mail Address | | | 99 |

:::Add Another:::   :::Clear:::   :::Cancel:::

:::Finished:::

Figure 5(b)

My Evaluations.com

Main | Mail | Voluntary | Reports | Evaluations | Users | Setup | Password | Logoff

Edit Hospital/Department Profile

Required fields are in bold type.

| | |
|---|---|
| Hospital Name | Hope Medical Center - Dept. Of Medicine |
| Program Type | Internal Medicine |
| Address | 1002 First Avenue |
| Address (Line 2) | |
| City | Heavenly |
| State | California |
| Postal Code | 90022 |
| Country | United States |
| Phone | 866-422-0554 |
| Fax | 800-865-7753 |

Select the first day of the academic year  7  3

Select the maximum number of evaluation exemptions  1

☑ Enable E-Mail Reminders of Evaluation Assignments

● Program Year Calendar

Figure 6

MyEvaluations.com

Main | Mail | Voluntary | Reports | Evaluations | Users | Setup | Password | Logoff

Hope Medical Center - Dept. Of Medicine
*Current Rotation Block: 3/10/2002 through 4/6/2002*

- Design an Evaluation — 112
- Edit Evaluations — 114
- Assign Evaluations — 116
- Manage Question Database — 118

- Main Menu
- Logoff Steve Fischman (SFischman)

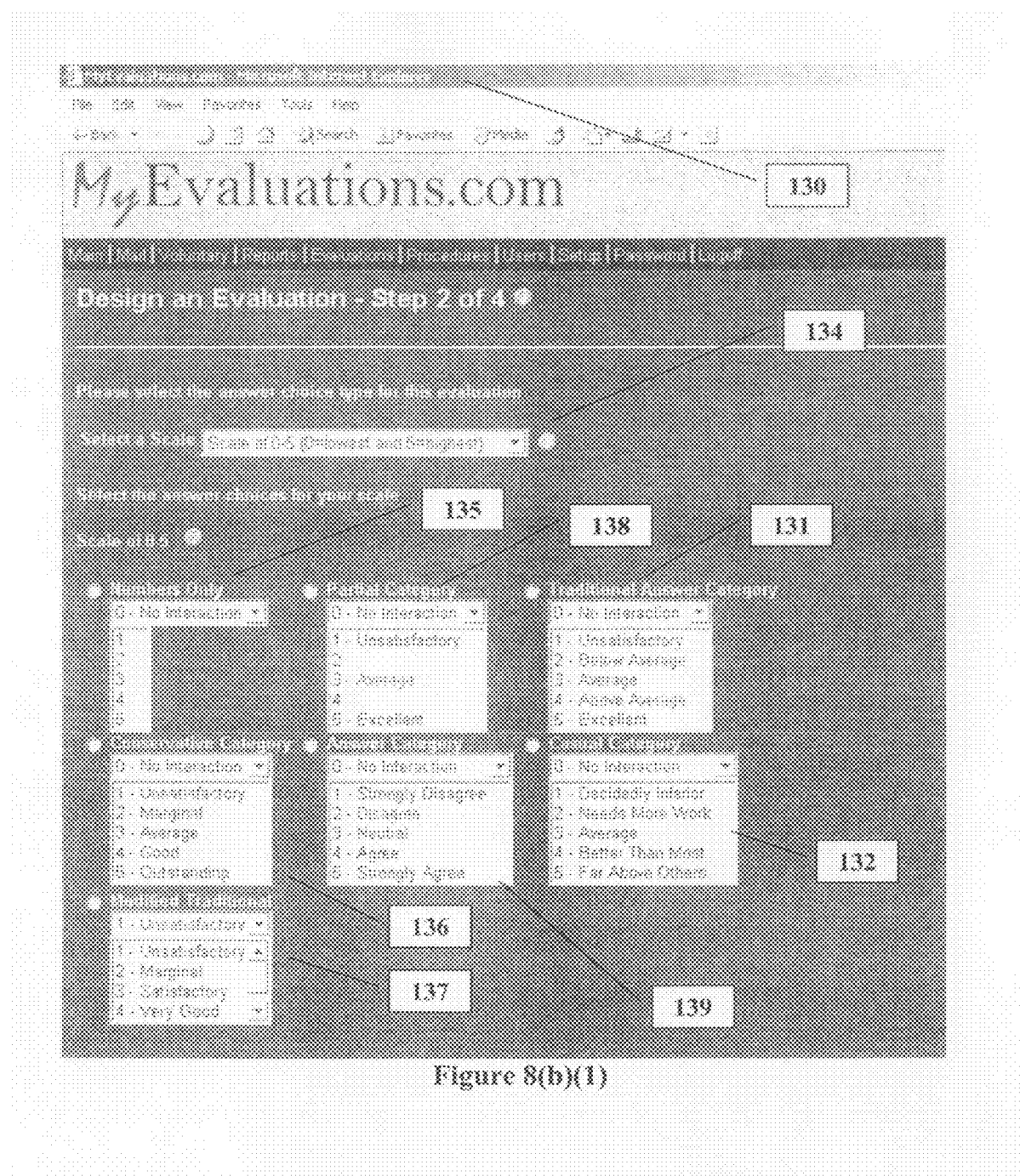
Figure 8(b)(1)

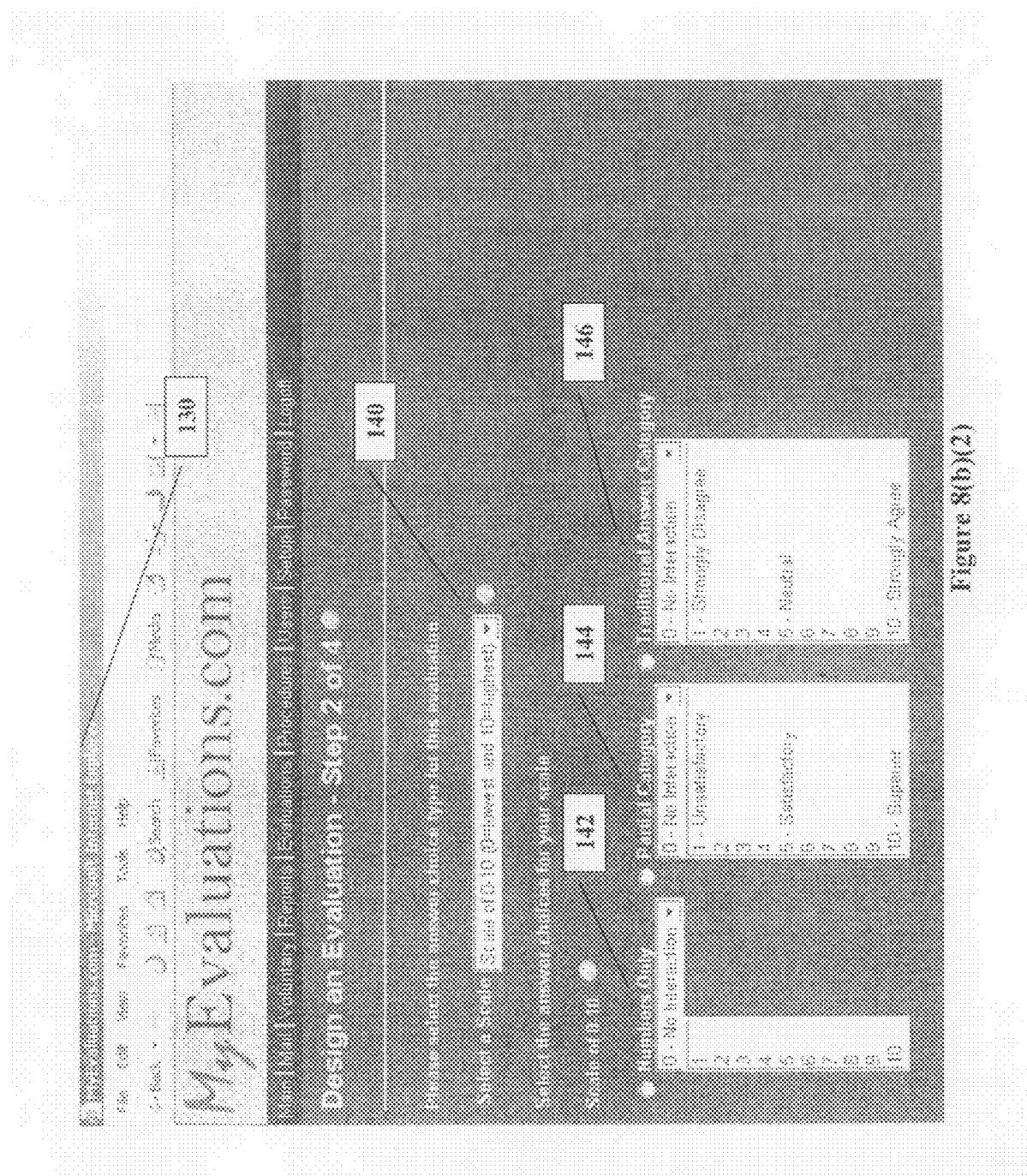
Figure 8(b)(2)

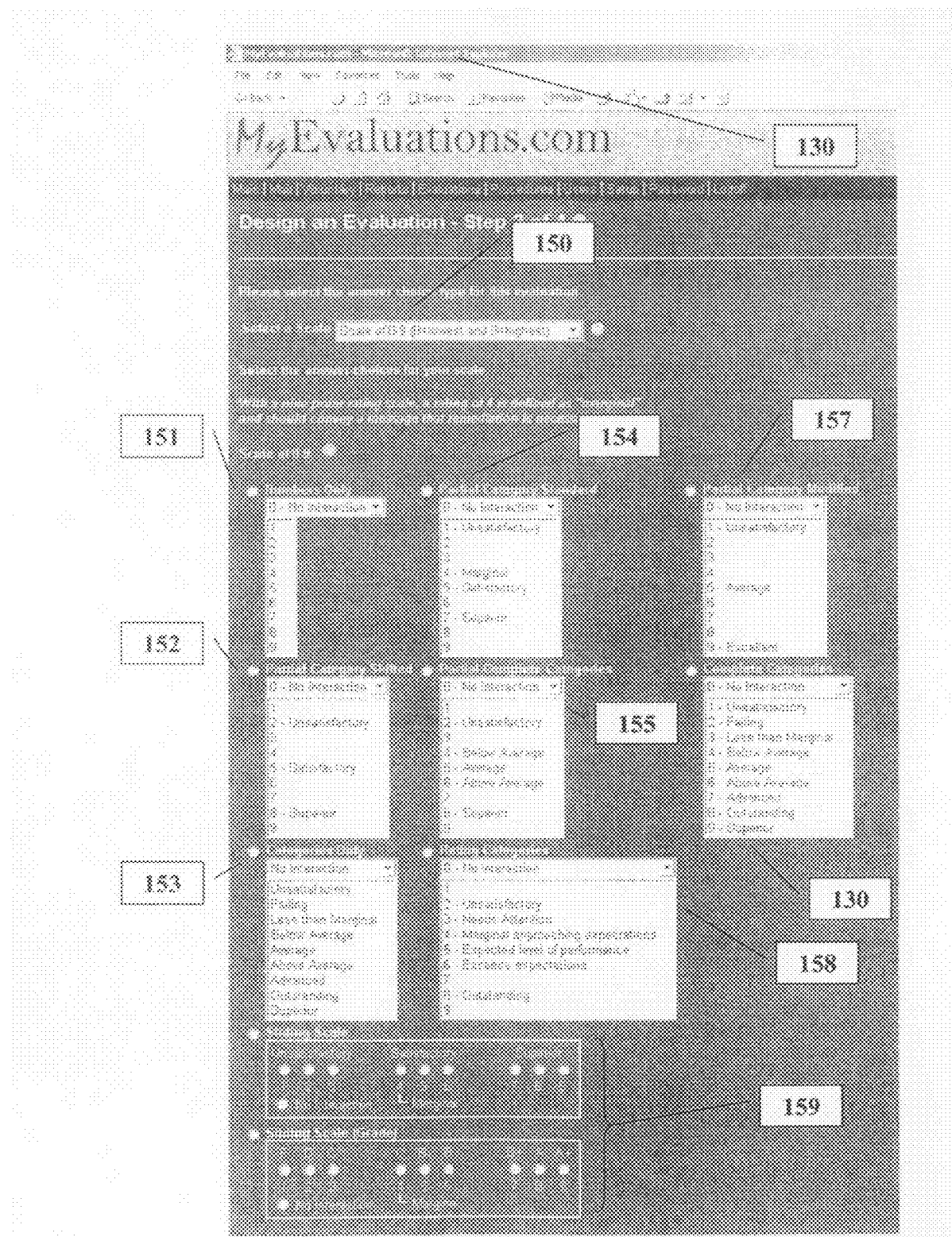
Figure 8(b)(3)

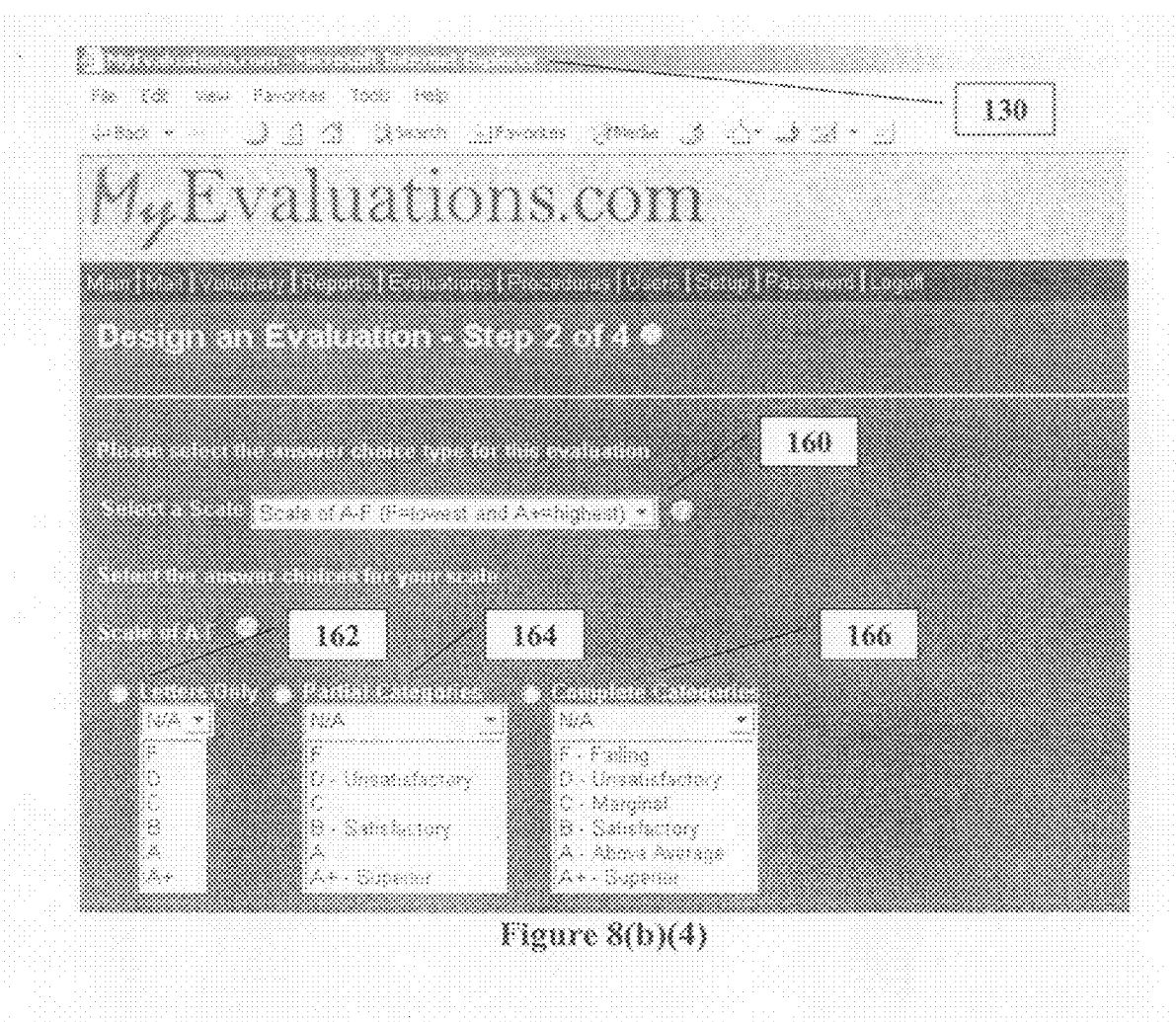
Figure 8(b)(4)

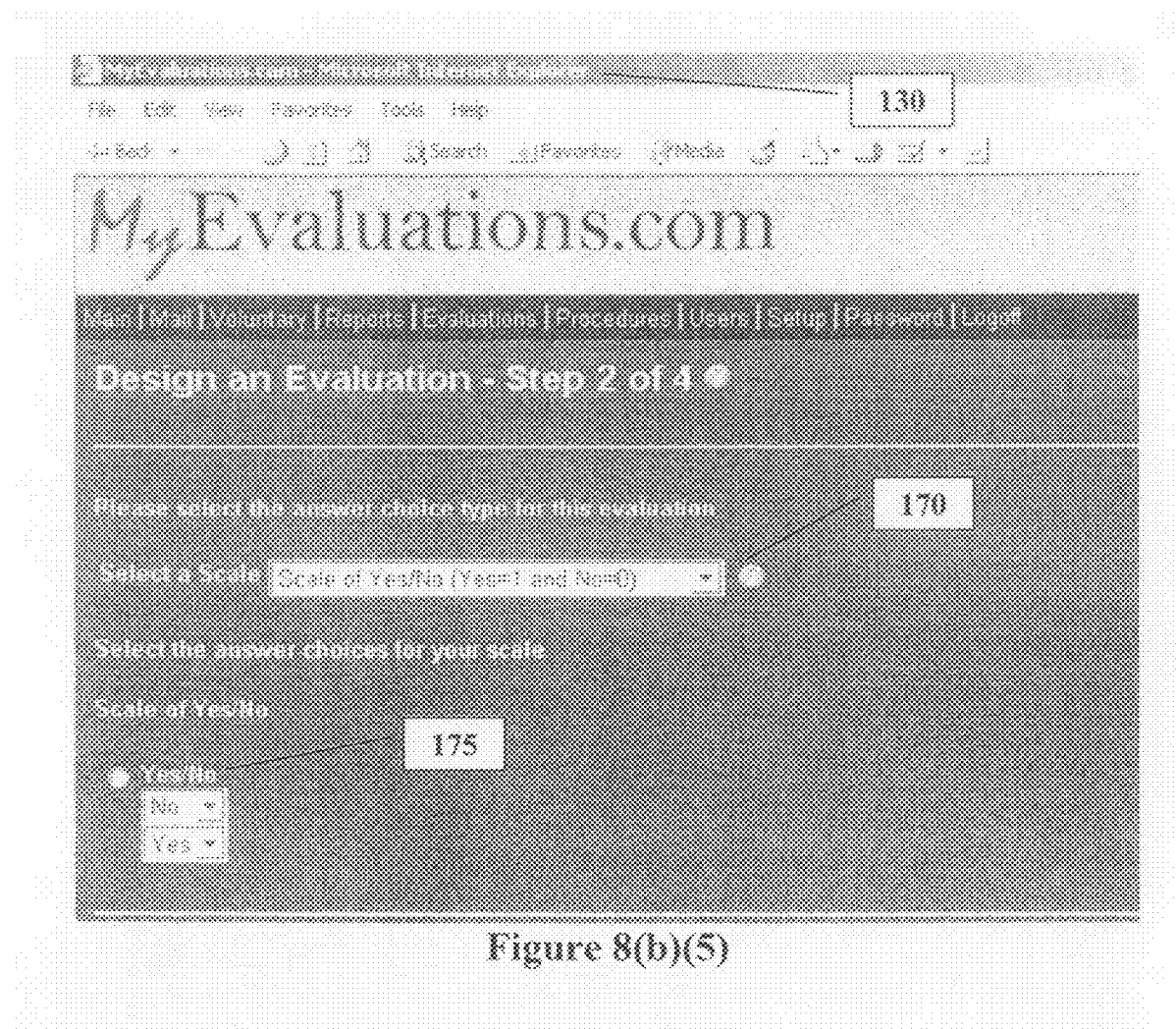
Figure 8(b)(5)

Summary of Group/Resident Evaluations
Standard Rotation Evaluation

Hope Medical Center - Dept. Of Medicine
*Report Date Range: 01-01-03 - 01-01-03*

Competency = Average score on competency for selected residents
Group = Average score of all PGYs represented (PGY-1)
Total = Average score of all PGYs

Clinical Skills - Category Summary (5.92, 65.5%)

| Question | JAdams | MAlbright | BAnthony | ACapone | Group | Total |
|---|---|---|---|---|---|---|
| History or physical examination often incomplete, superficial, illogical, unsound, insensitive to patient comfort, unreliable, inaccurate, or not problem focused. Misses obvious findings. Procedures performed without adequate knowledge or skills. Inept or careless. Frequently disregards need for adequate supervision, patient risk, anxiety and comfort. Inadequate patient informing and precedure documentation. | 6.40 71.1% | 6.80 65.7% | 6.60 72.2% | 4.67 51.8% | 5.92 65.8% | 6.34 69.3% |
| Patient history and physical examination is precise, logical, hypothesis driven, thorough, reliable, purposeful, efficient, accurate, directed toward the patient's problems, properly sequenced. Uses branching examination techniques when appropriate. Correctly detects subtle changes. Capitalizes a comprehensive patient data base. Procedures performed proficiently and carefully, minimizes risk and discomfort to patients. Properly informs patient and documents thoroughly. | | | | | | |

Interpersonal and Communication Skills - Category Summary (4.91, 54.6%)

| Question | JAdams | MAlbright | BAnthony | ACapone | Group | Total |
|---|---|---|---|---|---|---|
| Behaves uncaring or dismissive to therapeutic based relationships | | | | | | |

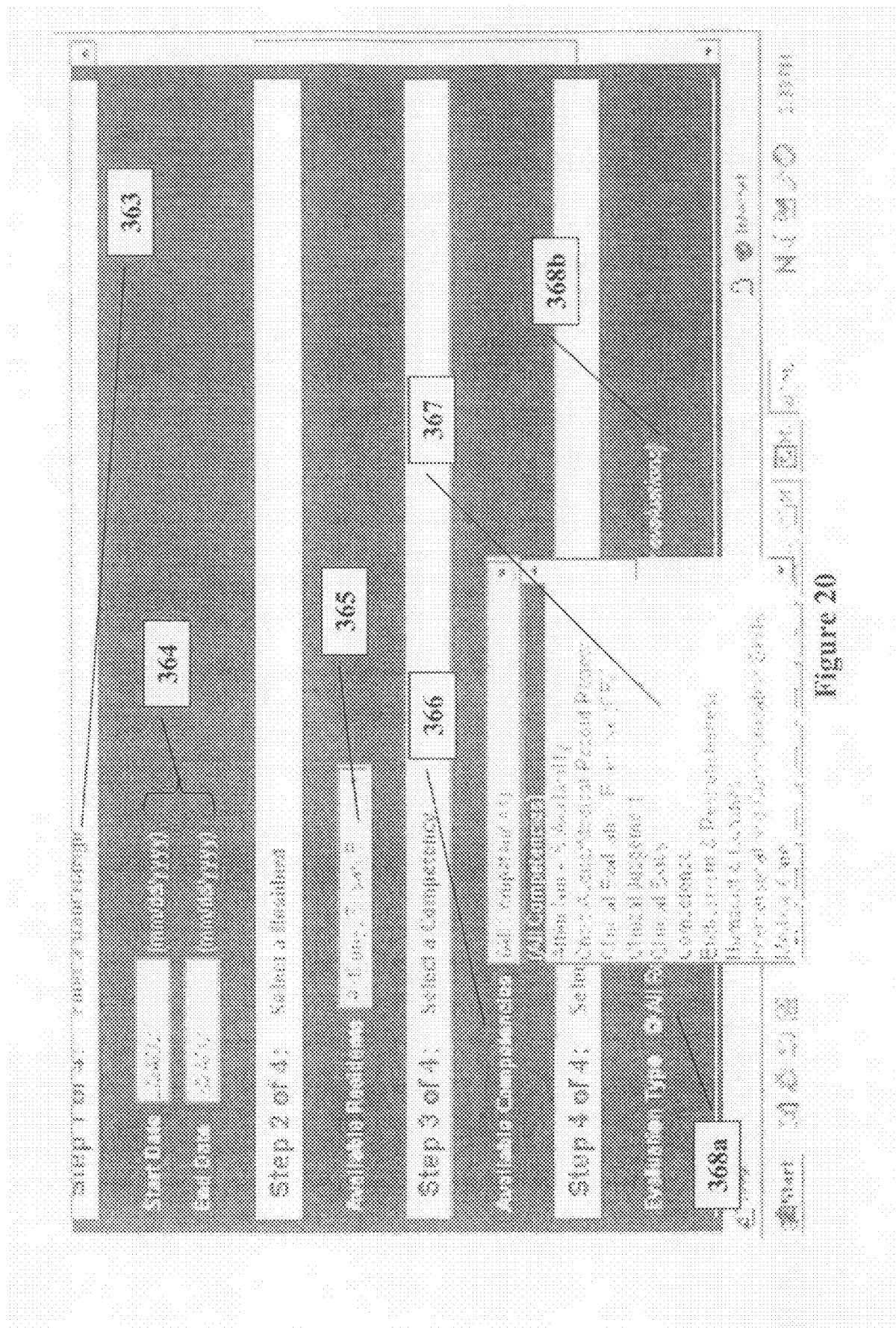

Overdue Resident Evaluations

Report Date/Time: 3/23/2002 3:44:45 PM

| Resident | Pager Number | Evaluation | Period | Individual | Status |
|---|---|---|---|---|---|
| Adams, John | 555-1212 | Bill's Sample Evaluation | 10/1/2001 to 12/31/2001 | Verrier, E | 82 Day(s) Overdue |
| Adams, John | 555-1212 | Bill's Sample Evaluation | 12/16/2001 to 1/12/2002 | Crawford, Cindy | 70 Day(s) Overdue |
| Adams, John | 555-1212 | Bill's Sample Evaluation | 12/16/2001 to 1/12/2002 | Johnson, Lyndon | 70 Day(s) Overdue |
| Adams, John | 555-1212 | Continuity Clinic Evaluation | 7/29/2001 to 8/25/2001 | Clinic, Clinic | 210 Day(s) Overdue |
| Adams, John | 555-1212 | Continuity Clinic Evaluation | 12/16/2001 to 12/15/2001 | Johnson, Lyndon | 97 Day(s) Overdue |
| Adams, John | 555-1212 | Evaluation Of Clinical Attending | 10/21/2001 to 11/17/2001 | Johnson, Lyndon | 126 Day(s) Overdue |
| Adams, John | 555-1212 | Evaluation Of Clinical Attending | 10/21/2001 to 11/17/2001 | Reagan, Ronald | 126 Day(s) Overdue |

Figure 21(a)

Class Rank
End-of-Rotation Resident Evaluation

Competency - (Medical Knowledge)
*Report Date Range: 01/01/01 - 01/01/03*

Print Report | Back to Menu — 391

Report Date/Time: 3/17/2002 2:26:16 AM

Medical Knowledge (All PGYs) - Category Summary (68.89%) — 392

| Rank | Resident | Medical Knowledge | Percentile | Humanistic Qualities | Medical Care | Professionalism |
|---|---|---|---|---|---|---|
| 1 | Liddy, Gordon | 88.89% | 100.00% | 77.78% | 72.22% | 77.78% |
| 2 | Adams, John | 77.78% | 80.00% | 83.33% | 86.30% | 63.30% |
| 3 | Kennedy, John | 68.44% | 60.00% | 94.44% | 75.00% | 97.22% |
| 4 | Davis, Angela | 66.67% | 40.00% | 55.56% | 66.67% | 86.67% |
| 5 | Smith, Robert | 58.94% | 20.00% | 66.11% | 61.11% | 65.26% |

SYSTEM AND METHOD FOR FACILITATING GENERATION AND PERFORMANCE OF ON-LINE EVALUATIONS

CROSS-REFERENCE TO RELATED APPLICATION

This application is a continuation application of U.S. Ser. No. 10/106,933 filed on Mar. 25, 2002, which is based on and claims the benefit of the filing of U.S. Provisional Patent Application No. 60/278,299 filed Mar. 23, 2001 entitled "SYSTEM AND METHOD FOR FACILITATING GENERATION AND PERFORMANCE OF ON-LINE EVALUATIONS", the contents and disclosure of which are fully incorporated herein by reference.

BACKGROUND OF THE INVENTION

1. Field of the Invention

The present invention generally relates to systems and methods for performing evaluations, and more specifically, to an on-line facilitator for building, customizing, distributing, and reporting web-based medical evaluations.

2. Discussion of the Prior Art

The Webster's English Dictionary defines evaluation as "to find the value or amount of or to judge the worth of".

Websites currently on the market simply allow users to login and complete existing evaluations. In other words, these websites are a data collection websites. Some examples include CollegeStats.com, RatingOnline.com and Teacher-Reviews.com.

For example: CollegeStats.com—anonymous online evaluation of teachers in any college or university. Teacher evaluations are then posted on the website for any other students to see. The site is "run by students, for students, and is completely free". RatingOnline.com—an online resource to find out "what the other students think of the professors at your college". The service allows students to find out whether the professor assigns and grades homework, number of quizzes and exams, and if the professor gives extra credit. StudentInfo.org—student-based website focusing on California colleges and universities, providing professor reviews to interested students. TeacherReview.com—student-run website collecting information from students about colleges across the globe, students complete evaluations to help other students select classes. Aceil.com—dedicated to the advancement of international academic exchange by facilitating the "evaluation of all international academic and professional credentials".

EducationEvaluation.com—provides online applications for various individuals to "clarify and verify credentials, degrees, and diplomas". Evaluations.com—online data collection of customized questions submitted in writing. Participants may include any person fitting the marketing requirements of a client company. Client companies submit the request in writing and Evaluations.com generates marketing questions based on those requirements. Primary business is to provide online marketing research. AgentFinders.com—site reports the performance Atlanta real estate agents. Service researches real estate market activity for each client request and provides data analysis in faxed or mailed reports.

There is one company on the market (Evaluations.com) that allows users to contact the company and design questions that are then implemented into an on-line evaluation. However, they do not support the ability to build evaluations online. Currently, there is no web-based evaluation system that allows users to build their own evaluations.

Further, many organizations that provide web-based evaluations allow registered users to be assigned to a specific evaluation or marketing questionnaire. However, these are tasks that are primarily completed internally by the organization or manually by a list. Alternatively, some web-based evaluation systems allow participants to be included based on the specific marketing requirements of a client company. None of the existing companies allow the administrative staff to make their own assignments.

Further, there are no organizations that allow administrative users of a web-based evaluation system to generate real-time online reports based on the data collected.

It is desirable to provide a comprehensive on-line facilitator that provides registered users all the tools necessary to build evaluation questions, individual evaluations, and to assign these evaluations to registered users within their organization.

It is further desirable to provide a comprehensive on-line web-based evaluation review system that enables collection of evaluation data and, once collected, enables registered users to access their account and review the results of these evaluations. More specifically, in the area of medical education, the facilitation of periodic scheduled evaluation between students and physicians for the enhancement of medical training and satisfaction of Board and regulatory agency requirements.

SUMMARY OF THE INVENTION

Referred to herein as MYEVALUATIONS.COM®, there is provided a web-based system that allows a user to literally design a complete evaluation system online, by providing a framework with pre-written and customized questions, and answer choices. In addition to providing on-line evaluations for customers, the MYEVALUATIONS.COM® web-based system provides other distinct functionality that sets it apart from all other web-based evaluation systems. These include: 1) the ability to custom build Evaluations$^{SM}$ completely online; 2) the ability to customize evaluations to an individual organization; 3) the ability to implement a comprehensive database of evaluation questions; 4) the ability to add custom questions; 5) the ability to assign Evaluations$^{SM}$, e.g., evaluations may be assigned to medical doctors, residents, nurses and fellows in order to provide 360 degree field of evaluations within the hospital environment; 6) the ability to assign evaluations to a group or to an individual; 7) the ability to make assignments according to an individual's name, sub-specialty, or post-graduate year; 8) the ability to assign evaluations by month, quarter, year, or a specific date or date range; 9) the ability to monitor pending evaluations and compliance; 10) the ability to automatically e-mail notification of assignments to reviewers; 11) the ability to automatically e-mail reminders of incomplete evaluations; and, 12) the ability for users to log on and complete ad-hoc evaluations.

Specifically, system functionality additionally includes the ability to review generated Evaluations$^{SM}$ including the ability to generate clear, concise, and comprehensive online reports from the data collected; and, the ability to track medical doctor, resident, nurse and fellow completion of evaluations. Thus, besides enabling building of evaluations online, a unique feature of MYEVALUATIONS.COM® is the ability to enable any administrative user to make assignments. For example, in the case of hospitals, the services provided by MYEVALUATIONS.COM® web-site enable the administrative staff to setup the users within a hospital. The second step is to design the online evaluations. The third step is to assign specific evaluations.

Assignments are made online and can be targeted to any registered member of the hospital. The assignments can be made by an individual's name, sub-specialty, or post-graduate year. These assignments can be made by month, by quarter, by year, or for a specific date. In addition, users can log on and complete ad-hoc evaluations. Individuals are then automatically notified by e-mail regarding pending and/or overdue evaluations. Therefore, the hospital has a streamline system that allows them to completely manage their internal evaluation system.

As a fourth step, MYEVALUATIONS.COM® services enable the generation of online reports based on the data collected. A unique feature of MYEVALUATIONS.COM is the ability to generate a real-time and online report based on the data collected via the online evaluations. The content of these reports is absolutely unique in design, by generating specific information on average performance and percentile ranking for individuals or a group, and cross-comparing the data between individuals or groups.

Advantageously, the present invention is targeted and designed for academic hospitals with users that include hospital administration, staff, medical doctors (i.e., Attendings), nurses, residents and fellows. Individual hospitals are able to register for services provided by the MYEVALUATION-.com® web-site by paying a monthly fee. Once a hospital is registered, the administrative staff can set up the staff, medical doctors, nurses, residents, medical students and fellows that make up the actual evaluation users. Once users have been set up, the administrative staff can design completely customizable evaluations that can then be assigned to the actual evaluation users. After assignments are made and users have answered the evaluation questions, the administrative staff can generate group-specific reports for internal review.

BRIEF DESCRIPTION OF THE DRAWINGS

The above and further advantages of the present invention may be better understood by referring to the following description in conjunction with the accompanying drawings, in which:

FIG. 3(a) illustrates an example Main menu comprising the default interface display 60 presented when a user logs on, and FIG. 3(b) illustrates an example Main menu comprising a default interface display 70 presented when an administrator user logs on;

FIG. 5(a) illustrates an exemplary Add User Profiles interface 85 and FIG. 5(b) illustrates an exemplary user profile data entry interface for a Resident user to enable the administrator to enter all relevant data pertaining to that new individual user;

FIG. 6 illustrates an Edit Hospital/Department Profile interface 100 for enabling the editing/updating of hospital/department profiles for medical profession evaluations;

FIG. 7 illustrates an example interface 110 which initiates presentation of a build evaluations Evaluations build option of FIGS. 8(a)-8(d).

FIGS. 8(a)-8(d) provide various interfaces for initiating processes to build/design and edit an evaluation;

FIG. 20 illustrates an example Summary of Resident's Core Competencies evaluation report interface 363 used for generating a Resident's Core Competencies evaluation summary report;

FIG. 21(a) illustrates an example the Overdue Evaluations report 372.

DETAILED DESCRIPTION OF THE PREFERRED EMBODIMENT

MYEVALUATIONS.COM® is a web-based service that provides registered users with all of the tools necessary to build evaluation questions, individual evaluations, and to assign these evaluations to registered users within different organizations, on-line. Once the data is collected, registered users can access their account and review the results of these evaluations. As will be described, the evaluations services in the preferred embodiment are targeted and designed for academic hospitals. The users include hospital administration, staff medical doctors, nurses, residents, medical students and fellows. Individual hospitals are able to register for the evaluations services by paying a monthly fee plus a one-time setup fee. Once a hospital is registered, the administrative staff can set up the staff, medical doctors, nurses, residents, medical students and fellows that make up the actual evaluation users. Once users have been set up, the administrative staff may design completely customizable evaluations that can then be assigned to the actual evaluation users. After assignments are made and users have answered the evaluation questions, the administrative staff may generate group-specific reports for internal review.

Figure 1:
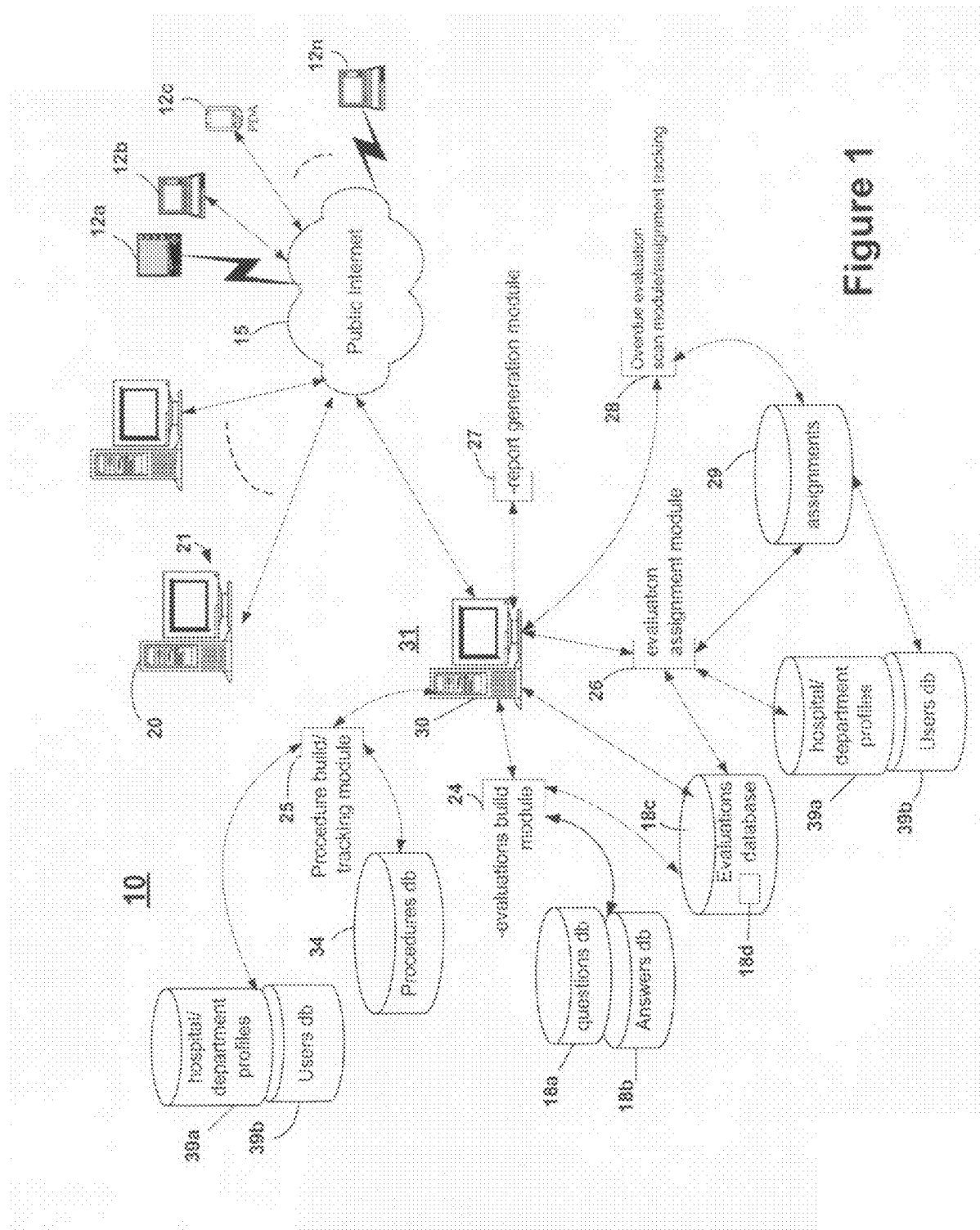
FIG. 1 is a diagram illustrating an Internet/Web-based communications system 10 established for enabling on-line evaluations build/assignment/management and reporting functionality and procedure build/tracking functionality according to the invention.

FIG. 1 is a diagram illustrating an Internet/Web-based communications system 10 established for enabling on-line evaluations build/assignment/management and reporting functionality according to the invention. As shown in FIG. 1, the invention comprises a web site 31, maintained and operated by MYEVALUATIONS.COM®, providing the secure on-line connection service over the Internet, that includes one or more web/database servers 30 comprising application and database software components for building and assigning evaluations online and reporting evaluation data. Registered users 12a, . . . , 12n of the web site are enabled to access the web site 31 remotely via wired or wireless connections to the Web/Internet 15. Wired communications between the web site 31 and the registered users are via the public Internet in accordance with standard TCP/IP protocols and optionally, over a secure communications link, e.g., secure sockets layer, BlueTooth or similar protocol. It is understood that parties 12a, . . . , 12n may access the Web/Internet via a personal computer/computing device, personal digital assistant, or like device implementing web-browser functionality, e.g., Netscape® or Internet Explorer®, or other browsing technology that may be compatible.

The MYEVALUATIONS.COM® web-site includes one or more web-servers 30 executing a collection of web-based applications implementing, for example, Active Server Page (ASP), JavaScript, HTML, VB Script with a SQL Server database. This preferably operates on a centralized server 30 and database with 128-bit security. Provided at a web-site server 30 are various Internet Information Services (IIS) which are mechanisms enabling files on a computer to be read by remote computers and particularly, used to house, secure and present a web site to either the Internet or an intranet (private network); and Component Services (COM) which function as a repository of custom Dynamic Link Libraries (dll's) that allow custom applications to perform actions in data sources foreign to the application, e.g., enabling a web page to query data on a database.

As shown in FIG. 1, a centralized database may be partitioned into several databases including a hospital/department profiles database 39a for storing respective profiles of the registered clients, e.g., hospitals and their various departments represented by a computer workstation at a hospital 21, and a users profiles database 39b associated with the hospital/department database for storing information for the various registered users (e.g., evaluators/evaluatees 12a, . . . , 12n) or administrator 20. The system 10 further includes a questions and answers database 18a, 18b, respectively, for storing questions and various answer choices to be used in the evaluations generated; an evaluations database 15c for storing the built evaluations for on-line use; an assignments database 29 for storing assignment information pertaining to the evaluators (assignees) of the on-line evaluations; and, a procedures database 34 for storing built procedures required to be performed by residents and medical students, for example, and used for tracking purposes as will be described in greater detail herein. As will be described in greater detail herein, the web-server 30 preferably executes a variety of application specific programs, including, but not limited to: an evaluations build software module 24 providing functionality for building evaluations to be assigned and stored in the evaluations database 18c; an evaluation assignment software module 26 providing functionality for assigning evaluations; an overdue evaluation scan module 28 providing functionality for tracking status of pending assigned evaluations; a report generator module providing functionality for generating a variety of reports; and a procedure build/tracking module 25 providing functionality for generating procedures and tracking the performance of procedures in satisfaction of Board and/or regulatory agency requirements, in the manner as will be explained in greater detail.

Login

Figure 2:
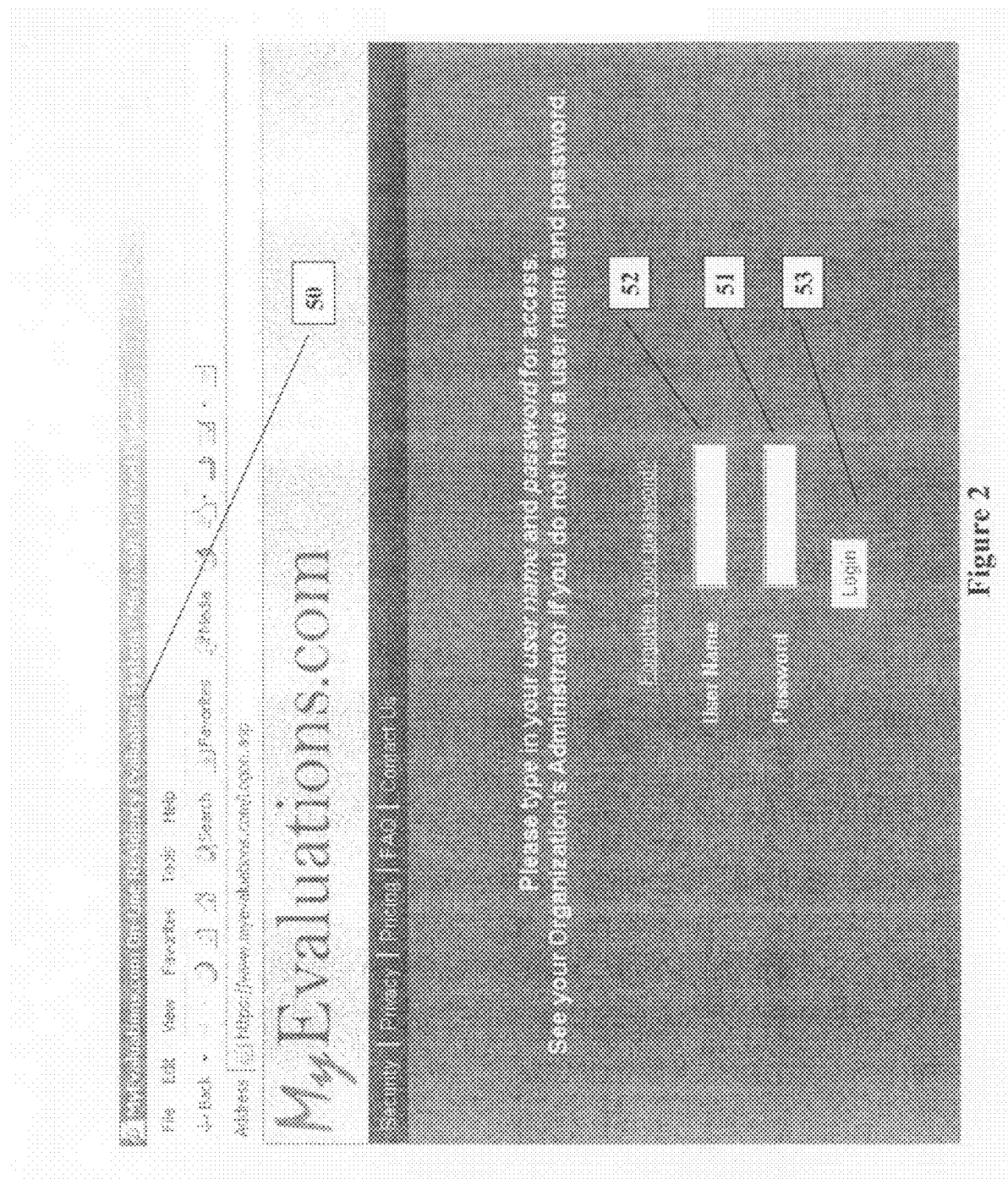
FIG. 2 illustrates an example MYEVALUATIONS.COM® log-in web page 50.

FIG. 2 illustrates an example MYEVALUATIONS.COM® log-in web-based communication (e.g., web-page 50) including a username field 51 and password field 53. Users may access the system using a pre-assigned username and password. If a registered user has forgotten their password or user name, user may retrieve this information via e-mail using a well-known forgotten user password function 52. The username may be automatically generated based on the user's first name and last name. When a user is added to the users database 39b (FIG. 1), the system will use the first initial from the first name and combine it with the last name in order to generate a complete username (e.g., John Adams will be JAdams). The application may then scan the database to assure that the username is unique. If the selected username already exists in the database, then a number (starting with 1 up to ∞) will be added to the end of the username (e.g., JAdams). The username can be optionally case sensitive; otherwise by default it will not be case sensitive. The password field 53 may require a minimum of four characters. The characters can be a combination of letters, numbers, and non-restricted symbols. The first time a user logs into MYEVALUATIONS.COM® he(s)he will be prompted to change their user to a new confidential password. The password can be optionally case sensitive; otherwise by default it will not be case sensitive.

User Access

By entering their unique username and password each user will have access to their evaluations and records. There are two general user access levels: an Administrator level which includes all individuals needing access to administrative features such as Manage User Profiles, Design Evaluations, and Reports (e.g., FIG. 3(*b*)); and, a User level which includes all individuals needing system access for completing evaluations and personal reports (e.g., FIG. 3(*a*)).

Each general user who logs on will have access to the following Main Menu options as shown in the example downloaded web-based communication 60 of FIG. 3(*a*) providing functionality for a particular registered user (e.g., hospital department 61) of the system 10. More particularly, from the main (Default) screen 60, the user may select the following options: a Voluntary option 62 providing user access to voluntary or Ad-hoc evaluations; a Procedures option 64 providing users access to on-line procedure submission and tracking; a Reports option 65 providing access to personal reports; a Password option 63 providing user access to change personal profile including password; and a Logoff option 66 enabling users to log-off user from the web-site.

It should be understood that each user registered as a system administrator or user/administrator (of a hospital department 61) who logs on the system will have access to the following Main Menu options as shown in the example downloaded web-based communication 70 of FIG. 3(*b*) providing additional functionality including: the Main (Default) screen option 70 as seen when a user logs on; a Mail option 72 which provides access to user's e-mail for sending individual or group e-mails; a Reports option 65 providing user access to personal reports; an Evaluations option 75 enabling the administrator system access to design, assign and manage department evaluations; the Procedures option 64 providing the administrator with access to additional on-line procedure tracking and management functionality; the Users option 76 providing access to manage user profiles; a Setup option 78 providing access to modify the department's profile and academic calendar; the Password option 63 providing access to change personal profile including user's password; and, the Logoff option 66. For users having a combined User/Administrator profile, they will have access to the Main, Mail, Voluntary, Reports, Evaluations, Procedures, Users, Setup, Password, and Logoff options.

Figure 3A:
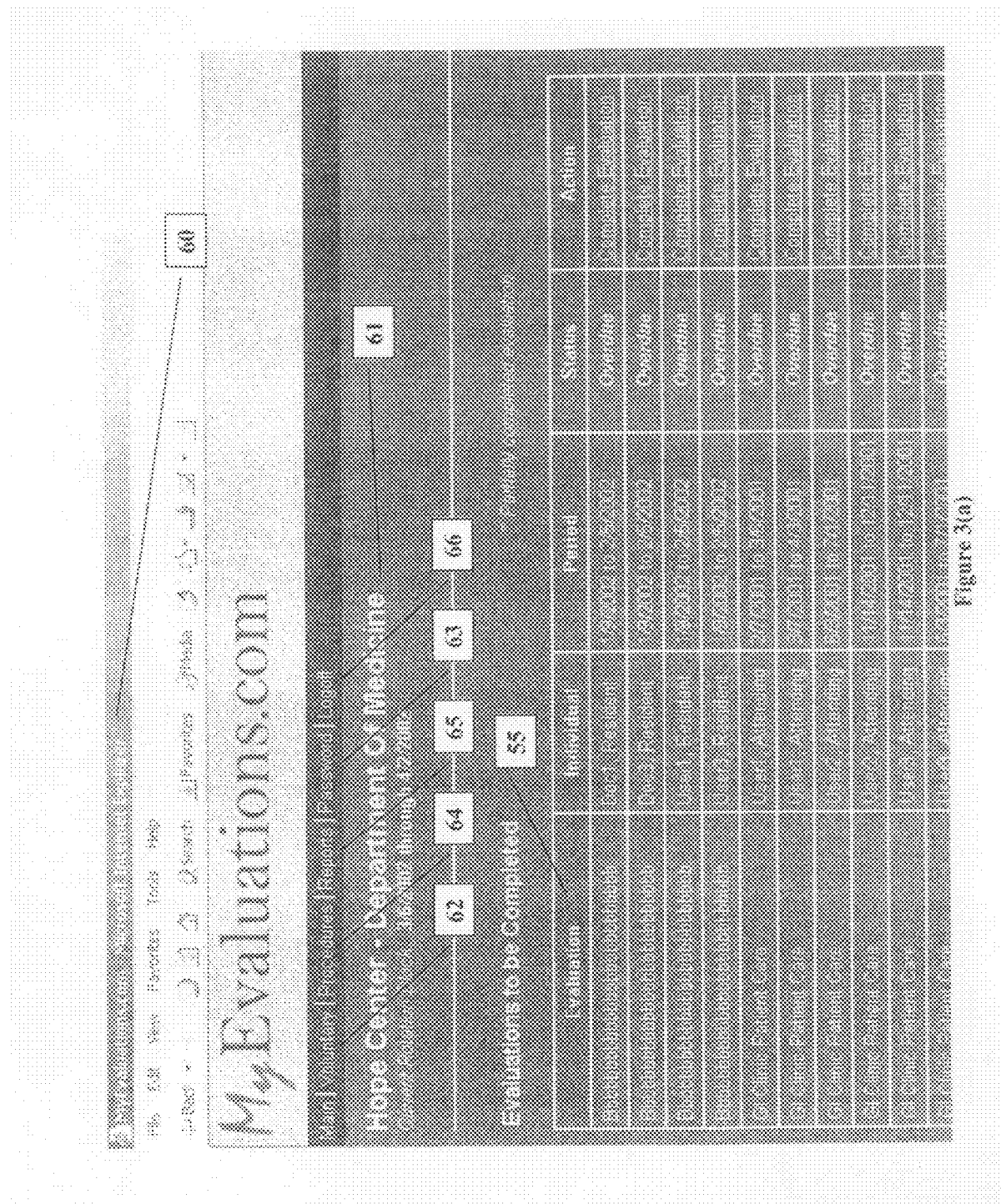
Figure 3B:
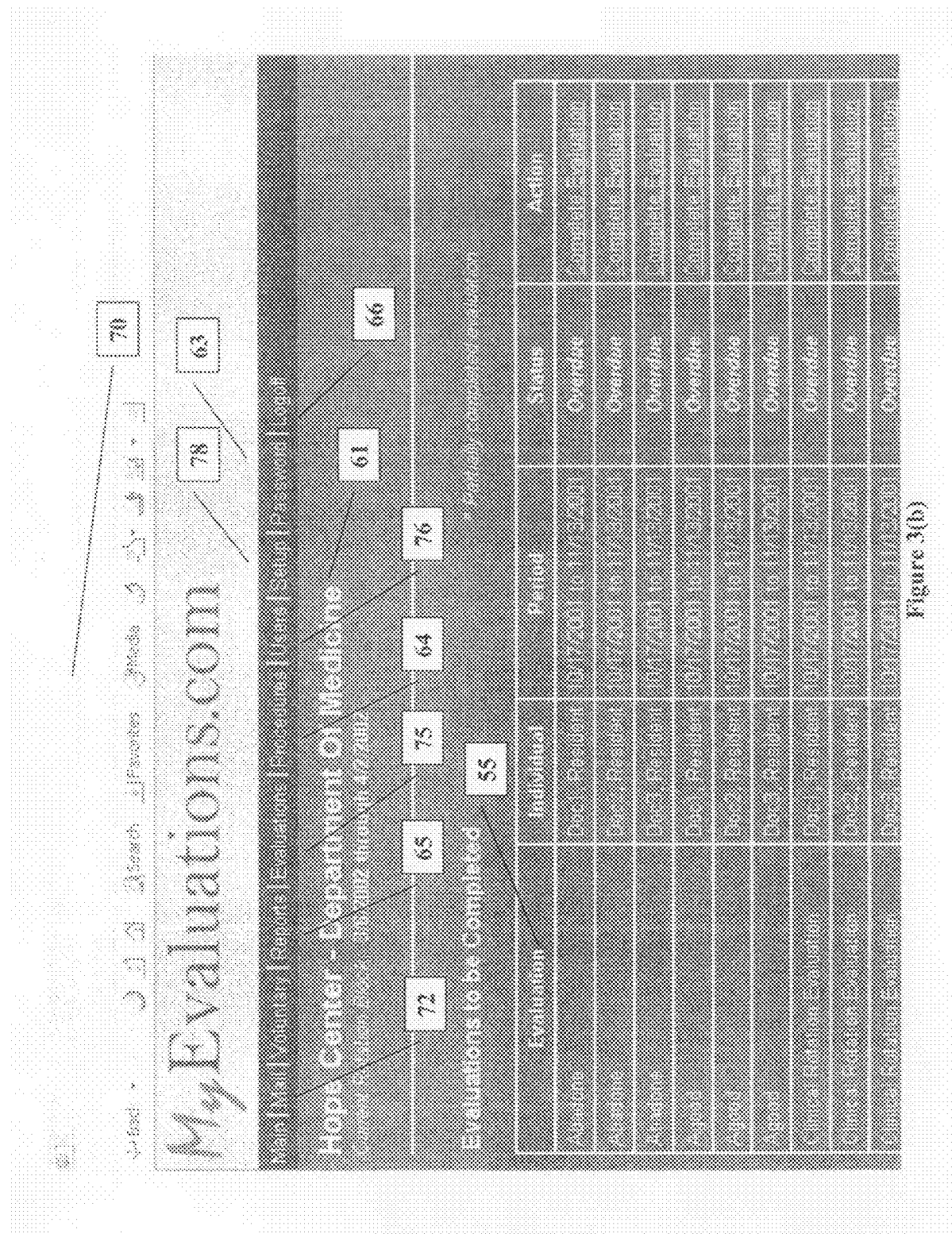
Figure 4:
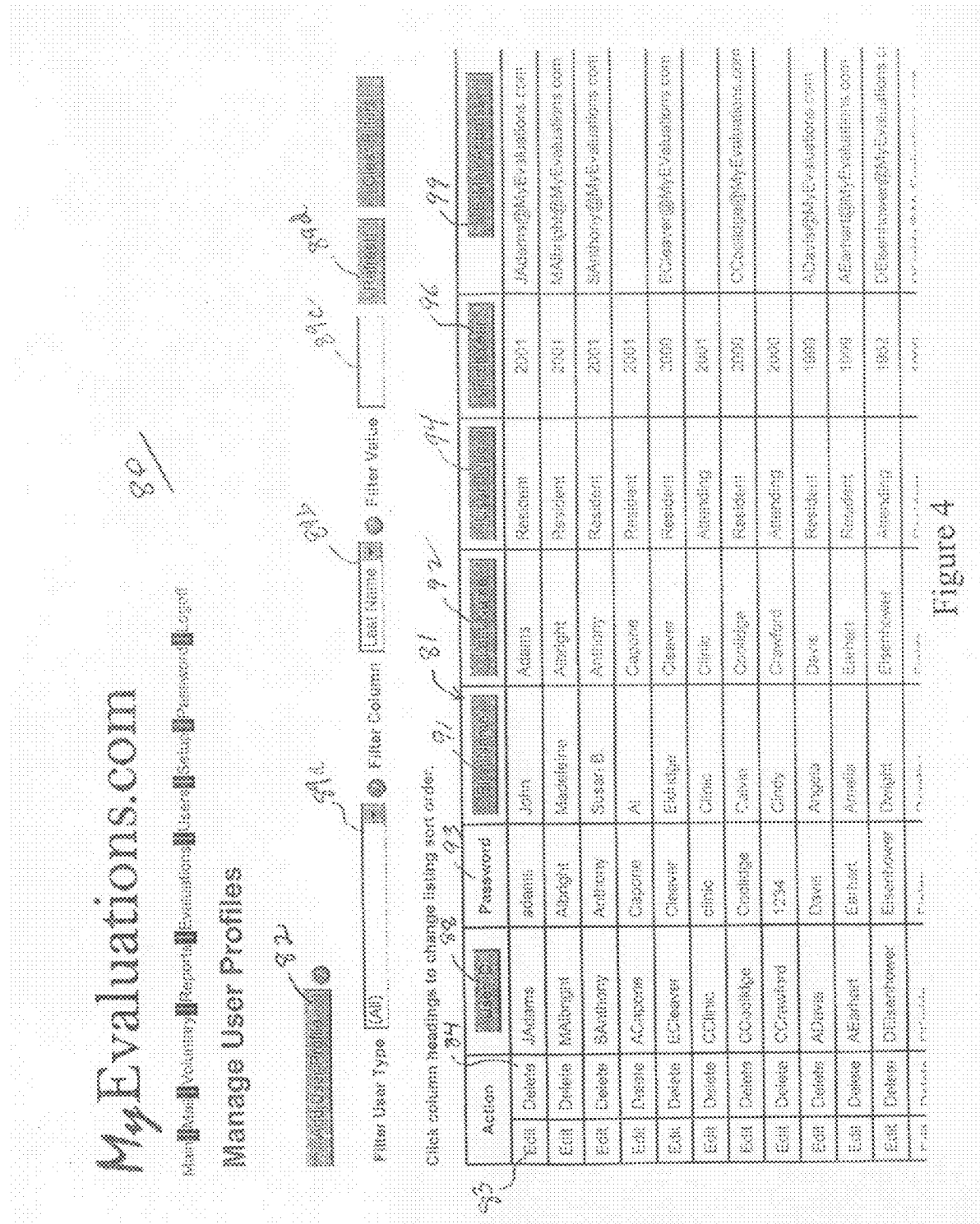
FIG. 4 illustrates an example screen 80 at the Administrator Access Level for enabling the management of user profiles, management of evaluations, management of hospital/department profiles, report generations, et al.
Figure 5A:
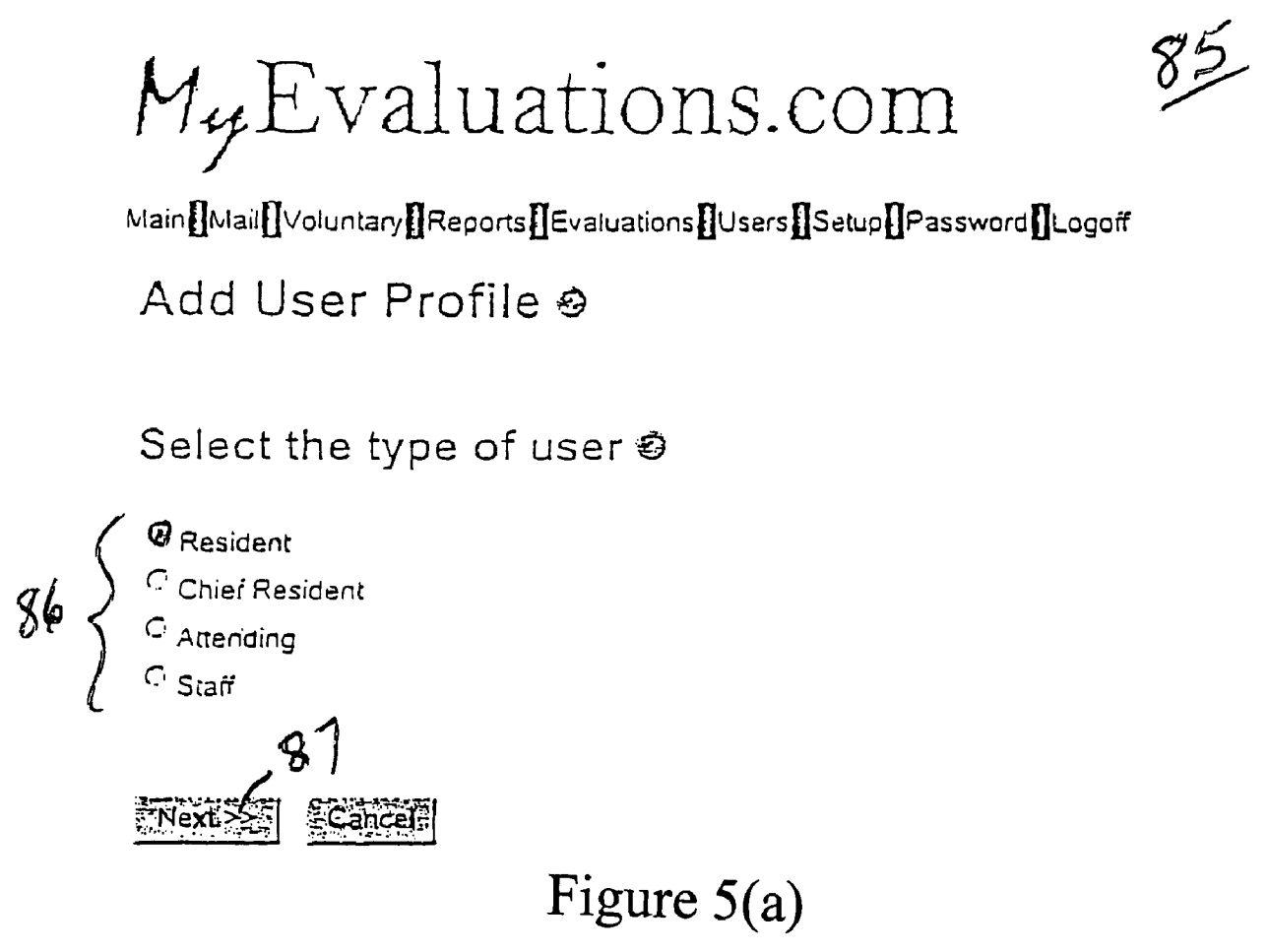

From the main menu interface 70 of FIG. 3(*b*), an administrator may add new users by selecting the Users option 76 which initiates presentation of a Manage User Profiles interface 80 such as shown in FIG. 4. It is from this interface that enables Administrator access to enable the management of user profiles, management of evaluations, management of hospital/department profiles, report generations, etc. From this screen, links are provided that enable functionality for system administrators who add user/hospital department profiles and manage base evaluation questions. As shown in FIG. 4, the Manage User Profiles interface 80 includes an Add User Profile button 82 which, when selected, generates for download to the administrator an Add User Profiles interface 85 such as shown in FIG. 5(*a*). The downloaded Add User Profiles interface 85 provides functionality for selecting the type of user (e.g., Resident, Chief Resident, Attending, Fellow, Nurse, Medical Student or Staff) by selecting an appropriate radio button 86; and, pressing a "Next" button 87 to advance to the next page, or "Cancel" to stop adding a new user. In response to pressing the "Next" button 87, a new web-based interface is communicated such as the example Add Resident User Profile interface 90 shown in FIG. 5(*b*) to enable the administrator to enter all relevant data pertaining to that new individual user in entry fields for entering(s)electing new user information including: the user's first name 91; the user's last name 92; the user's password 93; that user's access level 94 where the default value is "User" and should be used for all individuals needing access for completing evaluations; or, alternately, the access level is "Administrator" and should be used for all individuals needing access to administrative features such as Manage User Profiles, Design Evaluations, Procedures and Reports, etc; a Year First Started value 96 which is used to calculate a Post-Graduate Year ("PGY") and/or total number of years employed; optionally entering that user's pager number 97 which data may eventually be printed on an "Overdue Evaluations" report, and, on the user list page, as will be explained in greater detail herein; optionally entering that user's telephone number 98; that user's e-mail address 99 which data is used to send automatic notifications of pending and overdue evaluations. This is also used as the e-mail address for forwarding a forgotten password; and, that user's Default E-mail Address (not shown) which is an option that is only available under the Chief Resident user type and is used for all users who do not have an e-mail address on file. It should be understood that the Username is automatically generated based on the user's first initial and last name. If tie user name is already in use, then a number (starting from 1) will be placed at the end of the username.

Further with respect to managing user profiles, the downloaded web-based communication such as the example web-page illustrated in FIG. 4, displays the names of all current users. That is, FIG. 4 illustrates an example user profile management screen 80 for enabling the management (sorts and orders) of users. As shown in FIG. 4, all of the current users are displayed in a formatted table 81; the table including a heading row. Selecting the heading row will cause the entire table to sort based on the contents in the selected column. The table will include the following headings: 1) Edit 83: This function will permit the editing of individual user profiles. Selecting this function launches the user edit page similar to the add user profile page; 2) Delete 84: This function will permit the deletion of the individual user profile. It is important to note that this action will only cause deletion of the profile and not the associated evaluation data. Selecting this function additionally launches a confirmation communication (e.g. web-page) to confirm deletion by pressing "OK" or to "Cancel" deletion of the selected user profile; 3) User ID 88: The data from Username will be displayed in this column and is automatically generated based on the user's first initial and last name. If the user name is already in use, then a number (starting from 1) will be placed at the end of the username; 4) Password 93: the password of a registered user; 5) First Name 91: The first name of a registered user; 6) Last Name 92: The last name of a registered user; 7) User Type 94: causes display of data from User Type, including Resident, Chief Resident, Attending, Fellow, Nurse, Medical Student or Staff; 8) a First Year 96: display data from Year First Started which represents the year the individual first started working at the selected Department; 9) E-mail Address 99: The e-mail of the registered user; and, the pager of the registered user (not shown).

The Manage User Profiles function 80 of FIG. 4 may be sorted and manipulated in many ways. As outlined above, each heading column may be used to sort the table 81. In addition the top of the table will include the following functions: 1) Filter User Type 89a providing means to sort users by user type. Selecting a category from this list will display only individuals that are within the specified category. To display all individuals select the (All) option from the drop-down menu and then select: a Resident/Chief Resident; Attending; Fellow; Nurse; Medical Student; Staff, for example; and, 2) Filter Column and Value 89b, 89c providing means to sort users by user information by enabling selection an option from the Filter Column. Selecting a category from this list will display only individuals that are within the specified category. To display all individuals, an administrator may select the 'Refresh' button 89d from the screen 80. The options include: Last Name, Firstname Name, User ID, (first initial and last name), and, First Year (year first started). Next, the user may type a Filter Value 89c to find a user(s) based on specific criteria. This field is used in combination with the "Filter Column" option. (e.g., Select "Filter Column" option "First Name" and type the first few letters of a person's last name and press Refresh.) and the query results will be displayed in the table 81.

From the main menu interface 70 of FIG. 3(b), an administrator may setup a department profile by selecting the Setup option 78 which initiates presentation of a Edit Hospital/Department Profile interface 100 such as shown in FIG. 6. From this interface, an administrator may setup the department profile by entering information including: a hospital name 102, a program type 104, and address/contact information 105. Further entries include selection of the first day of the academic year in month day 107 which is used to set the commencement date of the 12 or 13 month calendar year, and the maximum number of evaluation exemptions 109 which are assigned to users in some circumstances to provide users with an option not to complete an assigned evaluation. It is understood that each time an evaluation exemption is exercised by a user, that user's exemption number total is decremented automatically.

In order to streamline the assignment functions, an automated calendar function is implemented. Particularly, the administrator for the department may select two options from the Setup Menu in order to determine their academic schedule and rotation blocks: 1) Number of Rotation Block (RB) per academic year which is either 12 or 13 block. That is, based on a 12-RB schedule the system will automatically calculate the start and end of each RB to correspond to the start and last day of each calendar month. The starting month of the 12-RB year will be based on the First Day of the Academic Year 107, or, based on a 13-RB schedule the system will automatically calculate the start and end of each RB based on a 28-day cycle independent of the calendar month. The starting day of the 13-RB year will be based on the First Day of the Academic Year 107; 2) a First Day of the Academic Year. The Department will select the month and date of the first day of the current academic year. This will represent the first working day for either the 12 or 13-RB schedule. From a Program Year Calendar option 106, an on-line calendar representing the months of the current academic year is presented to the user (not shown). By specifying the required data in the Calendar Function 107, the entire academic year's schedule can be seen at a glance. The start of each Rotation Block is highlighted in yellow and represents either a monthly or 28-day interval from the start of the academic date, depending upon whether the 12-RB or 13-RB year is implemented.

In the preferred embodiment, the setup provides an Auto Notification Function in order to notify users of overdue and incomplete evaluations, such as the tables 55 provided in the default main menu screens 60,70 of FIGS. 3(a) and 3(b), respectively. This notification function will automatically notify users of overdue evaluations and the department has the option 108 to turnoff this function from the Setup Menu 100. The Auto Notification Function 108 particularly will periodically (e.g., daily) initiate automatic scanning of the assignments database 29 (FIG. 1) for all pending and overdue evaluations and automatically send an e-mail reminder to each respective user. In an example embodiment, the notifications are sent for every seven days they are past due. For example, if an assignment was due Jan. 1, 2001 and remains pending, the system will send an e-mail notification on Jan. 8, 2001, Jan. 15, 2001, and Jan. 22, 2001 and so forth.

Figure 21B:
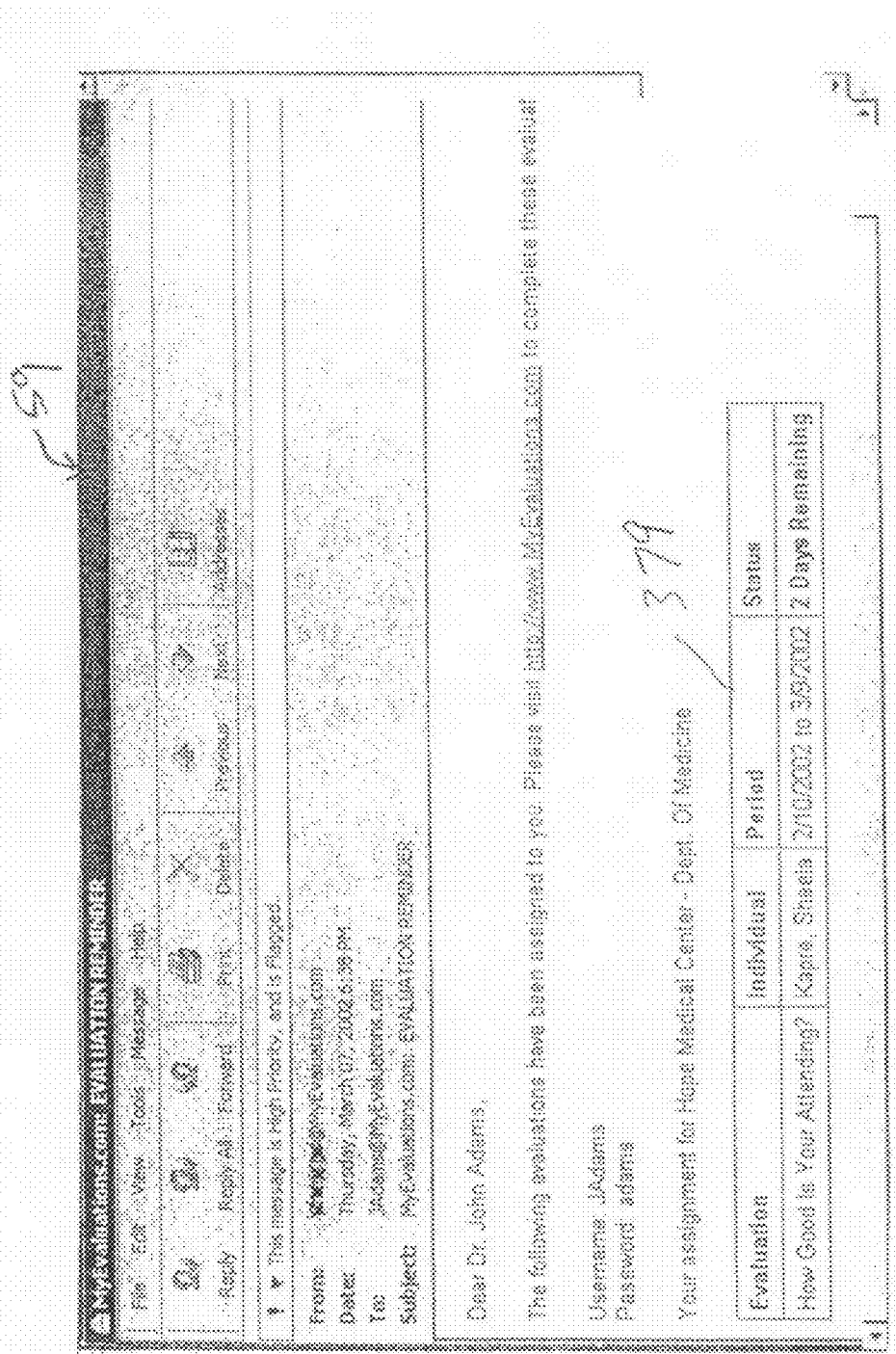
FIG. 21(b) illustrates an example e-mail communication 59 sent to an evaluator providing the evaluation assignments due/overdue.

Thus, it should be understood that Evaluators know they have evaluations due in one of two ways: 1) by logging on to MYEVALUATIONS.COM® which automatically displays their evaluation assignments in an "Evaluations to be Complete" table 55 as illustrated in the Main menu screens 60, 70 provided in the example user main menu screen of FIGS. 3(a), 3(b); or, 2) as will be described, they receive an e-mail with assignments due/overdue such as shown in the example e-mail notification 59 provided in FIG. 21(b).

Design/Build Evaluation

From the main menu interface 70 of FIG. 3(b), a user/administrator may build an evaluation by selecting the Evaluations option 75 which initiates presentation of a build evaluations interface 110 such as shown in the example interface of FIG. 7. From this interface 110, the user is provided with selection options to design an evaluation 112 that is customizable to individual organization; edit an evaluation 114; edit/manage the database of on-line evaluations 118 including the ability to implement a comprehensive database of pre-written evaluation questions, ability to add custom questions, ability to choose answer choices, etc; and the ability to assign evaluations 116.

Figure 8A:
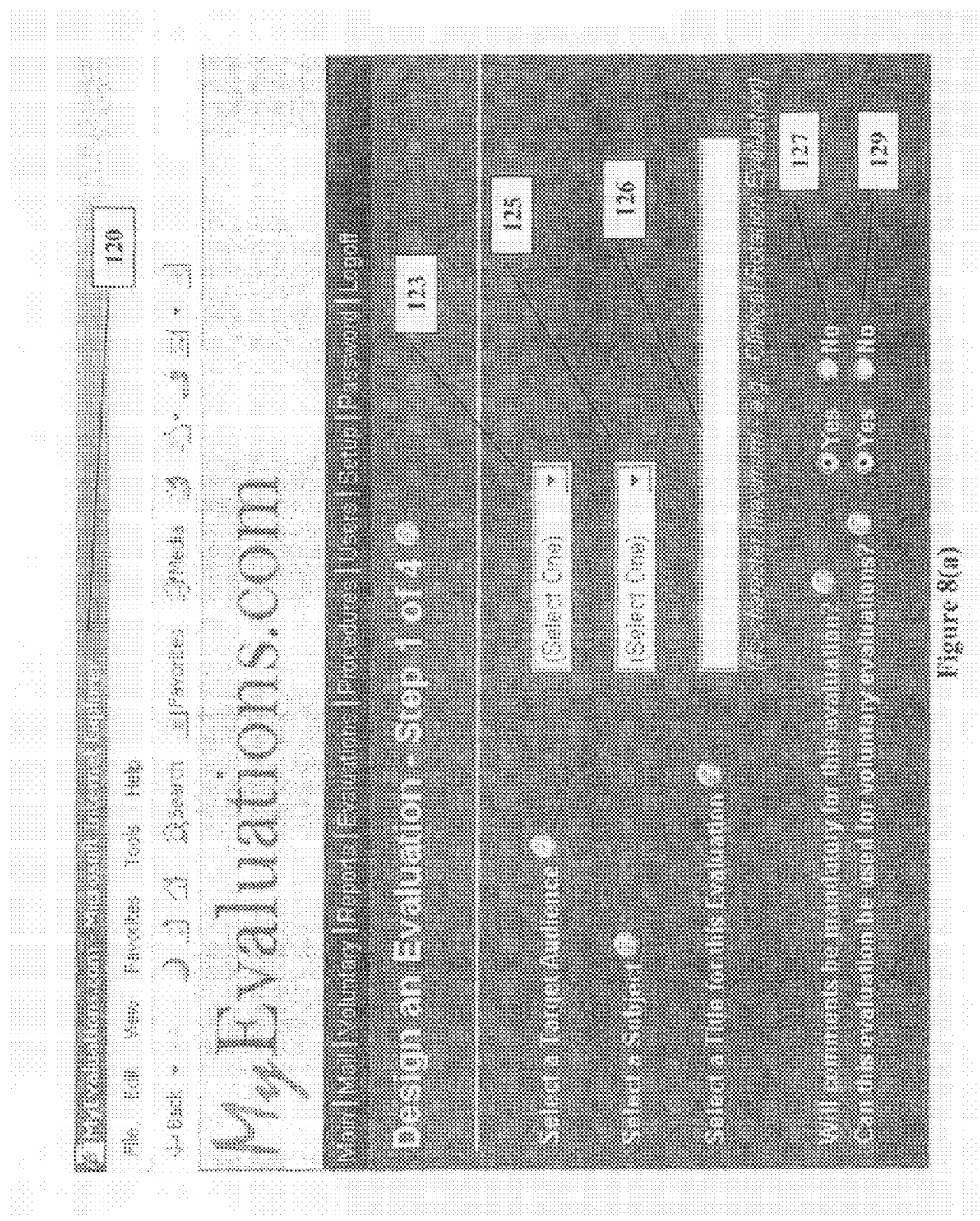

The selection of the design an evaluation 112 option initiates the generation of a web-based interface 120 such as shown in FIG. 8(a) that provides the first of a four (4) step process for building an on-line evaluation. The fully automated feature guide the user step-by-step for designing a customized on-line evaluation.

With respect to the example evaluations build interface 120 of FIG. 8(a), which implements the evaluations build module 24 of FIG. 1, process step are implemented for selecting the target audience 123; selecting the subject audience 125; specifying an evaluation title 126; specifying the requirements for comments 127; and, specifying whether the evaluation may be used as a voluntary evaluation, i.e., evaluation availability 129. The process continues by selecting a 'Next' button to advance to the next step, or 'Cancel' to exit and return to the Evaluations menu 110.

With respect to step 1, the step of selecting an audience is to specify who will be the evaluator and may include, for example: residents, medical students, fellows, nurses or attendings. If a resident is an evaluator, he(s)he will answer questions about the evaluatee, who may be medical students, fellows, nurses or attendings, or all. The user/administrator selects the Resident target audience from the drop down menu to design an evaluation targeted to the resident audience. If the medical student is an evaluator, he(s)he will answer questions about the evaluatee, who may be residents, fellows, nurses or attendings, or all. Select the Resident target audience from the drop down menu to design an evaluation targeted to the resident audience. If a fellow is an evaluator, he(s)he will answer questions about the evaluatee, who may be resident, medical students, nurses or attendings, or all. The user/administrator selects the Resident target audience from the drop down menu to design an evaluation targeted to the resident audience; If a nurse is an evaluator, he(s)he will answer questions about the evaluatee, who may be residents, medical students, fellows or attendings, or all. The user/administrator selects the Resident target audience from the drop down menu to design an evaluation targeted to the resident audience; If an attending is an evaluator, he(s)he will answer questions about the evaluatee, who may be residents, medical students, fellows, or nurses, or all. The user/administrator selects the Resident target audience from the drop down menu to design an evaluation targeted to the resident audience. The other option in this step is to select a unique title 126 for the evaluation that is being designed, e.g. "End-of-Rotation Evaluation" or "Resident Monthly Evaluation." Preferably, a generic title is used in order to use the same evaluation year-to-year so that data may then be used for trending and comparison reports. For example, unique titles may be used in order to differentiate evaluations that may be assigned in series. For example: "2001-2002 Monthly Resident Evaluation." Additionally, it is preferred that a unique title for evaluations and questions that change from period-to-period be used.

With respect to specification of whether comments are required 127, this is to inform whether the evaluator is required to write comments in order to complete an evaluation. Each evaluation will have a comment box for the evaluator to write comments and the option to make comments mandatory is YES (default) or NO (optional). If Yes is specified, the evaluator will be required to enter comments when completing an evaluation. If the evaluator forgets to enter comments, they will be automatically prompted to write comments. If No is specified, the evaluator will not be required to enter comments. A comment box will be provided for optional comments.

With respect to whether the evaluation being designed may be used for voluntary evaluations 129, the designer may choose to make evaluations available for voluntary submission. When a resident or attending logs onto MYEVALUATIONS.COM® he(s)he is presented with a list of assigned evaluations. In addition to assigning specific evaluations to residents and attendings (mandatory evaluations), evaluators have the option to complete voluntary evaluations. This is a valuable tool for evaluating specific individuals that were not assigned to an evaluator For example, a Resident rotating through Infectious Diseases is assigned a mandatory end-of-rotation evaluation on each of his three ID attendings (mandatory evaluations). During the course of the month she spends a great deal of time rounding with the Chief of Pharmacy and now wants to evaluate him. Since there are no mandatory evaluation assigned to her to complete on the Chief of Pharmacy, she may choose to complete a voluntary evaluation. By choosing to complete a voluntary evaluation, the evaluator may select the Evaluation and Evaluator. Only evaluations that are marked as voluntary-YES (default) will be made available to evaluators completing voluntary evaluations. The administrator can change the status of an evaluation from Voluntary to Non-Voluntary at anytime (see section Edit Evaluations). If YES is selected, then the evaluation is to be included as part of the list of evaluations available to evaluators wanting to complete voluntary evaluations; if No, the evaluation will not be included as part of the list of evaluations available to evaluators wanting to complete voluntary evaluations. However the evaluation will be available for mandatory evaluations, when making assignments, as will be explained in greater detail herein.

As mentioned, for each evaluation created there is associated a set of questions and answer choice responses as shown in FIG. 1 databases 18a,b. The second step of designing an evaluation involves the step of selecting the answer choice types, which comprise a scale in one preferred embodiment, and selecting a respective category as illustrated in the example received web-based communications 130 of FIGS. 8(b)(1)-8(b)(5). From each of these displays, selecting 'Next' will advance to the next (third) design step, and 'Back' to return to step one, or 'Cancel' to exit and return to the Evaluations menu.

As shown in FIGS. 8(b)(1)-8(b)(5), with respect to selection of answer choice response types, interface 130 provides a drop-down menu from which a user may select the answer scale granularity. There are five major answer scales that may be selected from this menu including: a Scale 134 of 0-5 (0=lowest and 5=highest) as shown in FIG. 8(b)(1); a Scale 140 of 0-10 (0=lowest and 10=highest) as shown in FIG. 8(b)(2); a Scale 150 of 0-9 (0=lowest and 9=highest) as shown in FIG. 8(b)(3); a Scale 160 of A-F (F=lowest and A+=highest) as shown in FIG. 8(b)(4); and, a Scale of Yes/No (Yes=9 and No=1) as shown in FIG. 8(b)(5). A user may choose the respective category by pressing the button next to the category name.

With respect to selection of the Scale 134 of 0-5 in FIG. 8(b)(1), there are six answer choice categories under this scale. These represent the actual answer choices an evaluator will see when completing an evaluation. A user will only have one answer choice type per evaluation. The user/administrator chooses the desired category by pressing the button next to the category name. Categories in the 0-5 scale include: a Numbers Only category 135, i.e., numbers without descriptors; a Partial Category 136, i.e., numbers with descriptions for numbers 1, 3 and 5; a Traditional Answer Category 131, i.e., numbers with traditional descriptors; a Conservative Category 136, i.e., numbers with conservative descriptors; an Answer Category 139, i.e., numbers with conformity descriptors; and, a Casual Category 132, i.e., numbers with casual descriptors.

With respect to selection of the Scale 140 of 0-10 in FIG. 8(b)(2), there are three answer choice categories under this scale that are the actual answer choices an evaluator will see when completing an evaluation. A user can only have one answer choice type per evaluation. The user/administrator chooses the desired category by pressing the button next to the category name. Categories in the 0-10 scale include: the Numbers Only category (without descriptors) 142; a Partial Category 144, e.g., having numbers with descriptions for numbers 1, 5 and 10; and a Traditional Answer Category 146, e.g., numbers with traditional descriptions for numbers 1, 5 and 10.

With respect to selection of the Scale 150 of 0-9 in FIG. 8(b)(3), there are eight answer choice categories under this scale, including the 9-point Sliding Scale answer choices for the two-part questions (as used by the American Board of Internal Medicine (ABIM)). Preferably, there are nine answer choice categories under this scale, including the 9-point Sliding Scale answer choices for the 2, 3, and 4-parted questions (as used by the ABIM). These are the actual answer choices an evaluator will see when completing an evaluation. A user will only have one answer choice type per evaluation by choosing the desired category by pressing the button next to the category name. The principal advantage of the nine-point scale over shorter scales are the additional levels of discrimination it provides. Thus, scales that include more rating steps tend to produce more reliable ratings. When using the 9-point rating scale, a rating of 4 is defined as "marginal" and should convey a message that remediation is necessary. A clearly satisfactory resident should receive a rating of "5". Categories in the 0-9 scale 150 include: a Numbers Only 151, i.e., numbers without descriptors; a Partial Category Standard 154, i.e., numbers with descriptions for numbers 1, 4, 5 and 7; a Partial Category Modified 157, i.e., numbers with descriptions for numbers 1, 5 and 9; a Partial Category Shifted 152, i.e., numbers with descriptions for numbers 2, 5 and 8; a Partial-Complete Categories 155, i.e., numbers with descriptions for numbers 2, 4, 5, 6 and 8; a Complete Categories 158, i.e.: numbers with descriptions for all numbers; Categories Only 153, i.e., descriptions only without numbers; a Rating Categories 156, i.e., descriptions with ratings so that 5 conveys "Expected level of performance" rather than "Satisfactory"; and, Sliding Scale 159, i.e., numbers with descriptions for numbers 2, 4, 5 and 8. Select the Sliding Scale answer category in order to design a two-tiered evaluation (as used on the ABIM Resident Evaluations). This answer choice is only available when designing an evaluation for the Attending audience.

With respect to selection of A-F scale 160 in FIG. 8(b)(4), there are three answer choice categories under this scale that are the actual answer choices an evaluator will see when completing an evaluation. Categories in the A-F scale 160 include: a Letters Only category 162, e.g., numbers with letters, a Partial Categories 164 with numbers and letters with descriptions for numbers, e.g., 2/D, 5/B and 9/A+; and, Complete Categories 166, e.g., numbers and letters with traditional descriptions for all numbers The remaining Yes/No scale 170 in FIG. 8(b)(5) includes a Yes/No category 175, for example.

Figure 8C:
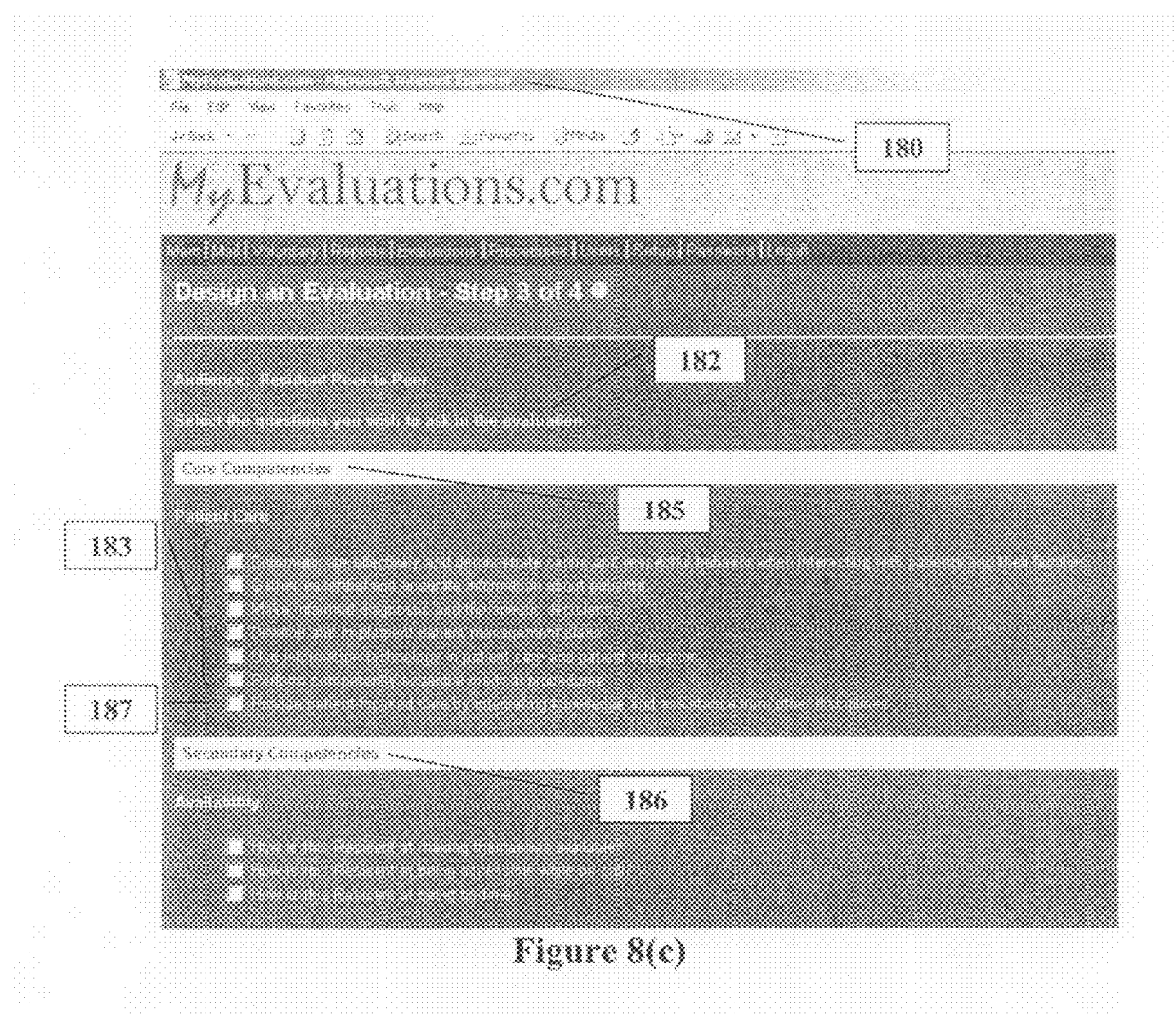

The third step of designing an evaluation involves the step of selecting the questions to include in the evaluation for storage in questions database 18(a) in FIG. 1. This step is illustrated in the example web-based communication 180 of FIG. 8(c). As shown in FIG. 8(c), a user may preferably scroll through a list of questions 182 and mark each question to include in the evaluation with a check mark in box 187; then select 'Next' to advance to the next step, or 'Back' to return to Step two, or 'Cancel' to exit and return to the Evaluations menu. Questions are categorized into competencies, which are sorted alphabetically. More particularly the user will be presented with a unique set of questions, depending on the audience being targeted. Questions are specific to the selected audience. A user may additionally write his/her own questions or select the default questions already stored in the database. For example, when designing evaluations for the Resident audience (residents evaluating residents (peer-to-peer audience)) the user may be presented with a general list of competencies. Each competency will have its own set of questions 183. When designing evaluations for the Attending audience (attendings evaluating residents) the user may be presented with two sets of competencies: a set of Core Competencies 185 with six unique sub-categories of competencies; and, a set of Secondary Competencies 186 with multiple sub-categories of competencies. To use two-tiered questions (as used in standard ABIM resident evaluations) the user first selects the "0-9 Sliding Scale" listed in FIG. 8(b)(3). Two-tiered questions are designed with a negative statement on the left and a positive statement on the right. All these questions use a 9-point sliding scale as defined herein.

The fourth step of designing an evaluation involves the step of viewing and confirming the evaluation as it will appear when published (i.e., available to residents and attendings) and, is the last step before completing the customized evaluation. The user will then by presented with a 'Finish' option (not shown) to confirm the evaluation, or a 'Back' option to return to Step 3, or 'Cancel' to exit and return to the Evaluations menu.

Even though selecting 'Finish' ends the evaluations design stage, it is understood that changes may still be made to the evaluation. Once the 'Finish' option is selected, the custom evaluation is placed into a storage Evaluation Library 18d in evaluations database 15c (as shown in FIG. 1). All stored evaluations may be subsequently accessed by the user by selecting the 'Edit Evaluations' menu option as will be described in greater detail herein. It is noted that a 'published' evaluation cannot be edited, however it can deleted and/or retired from circulation. In order to make an evaluation available to residents and attendings, the user must "Publish" the evaluation. To publish an evaluation, the user enters the 'Edit Evaluations' menu as will be explained with respect to the interface 190 shown in FIG. 8(d). From this interface, the user may select the 'Publish' option associated with the desired evaluation. The user will then be prompted with a confirmation screen (not shown) in order to confirm readiness to publish the evaluation.

Edit Evaluation

Returning to the Evaluations Build interface 110 of FIG. 7, the user may select an option 114 to edit evaluations. In response to selecting option 114, the user is presented with a downloaded web-based interface 190 for viewing, editing or deleting an existing evaluation 199.

Figure 8D:
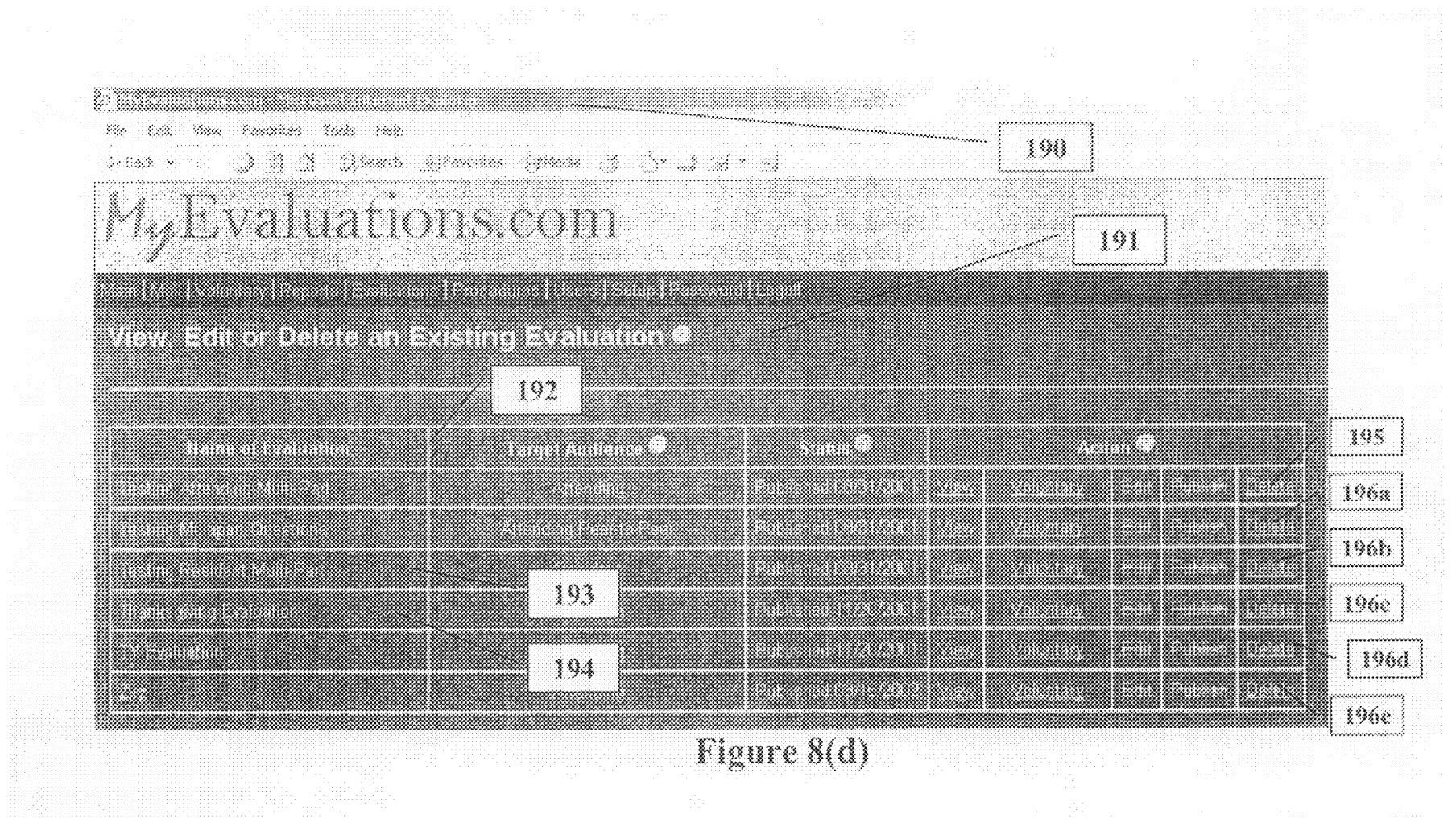

Particularly, in view of FIG. 8(d), there is presented the contents of the exiting library of evaluations enabling the user/administrator to view, edit, delete, and publish existing evaluations. A user may also change the status of a voluntary evaluation to non-voluntary. The Edit Evaluations option is presented as a table 191 that includes a listing of the existing library of evaluations for the client to view, edit, delete, and publish. The headings of table 191 include the Name of the Evaluation 192, i.e., the name of the evaluation as it was typed by the administrative user in the first evaluation design step. The name of an evaluation can be Edited until the evaluation is published. Once an evaluation is published the name cannot be changed; the Target Audience 193, i.e., referring to the evaluator or the person completing the evaluation; the Status 194 indicating a particular evaluation as being "Published" and the respective date the evaluation was published, or a status of "Not Published". As mentioned, an evaluation must be published in order to make it available for general use. Once the evaluation has been published, this link appears as and the evaluation can no longer be edited. A user may still delete, view, or change voluntary status of a published evaluation; and, various Actions 195 such as view 196a, edit 196c, delete 196e, publish 196d, and, voluntary/non-voluntary 196b, each action's availability 196b being dependent upon the status of the evaluation. The 'View' link 196a to the right of the desired evaluation is provided to enable display or print of a template of how the evaluation will appear to the audience. The Edit link enables editing of an existing evaluation, e.g., by modifying the elements of the evaluation before it has been published. Once the evaluation has been published, this link is no longer available and appears as 196c. The deletion of an exiting evaluation is performed by selecting the 'Delete' action 196e to the right of the selected evaluation. Once an evaluation is deleted, it can no longer be used for future evaluation assignments. The data from a deleted evaluation is preserved and can always be retrieved in a Report as will be hereinafter described in greater detail. Selection of the publish link 196*d* permanently publishes the evaluation for general use. Once the evaluation has been published, this link appears as and the evaluation can no longer be edited. One may still delete, view, or change voluntary status of a published evaluation. The Voluntary/Non-voluntary link 196*b* is a toggle option allowing a user to select the display of the evaluation to residents/attendings in order to complete a voluntary evaluation. The 'Non-voluntary' option will only display the evaluation when it is assigned to residents/attendings, for example.

Assign Evaluation

Figure 9A:
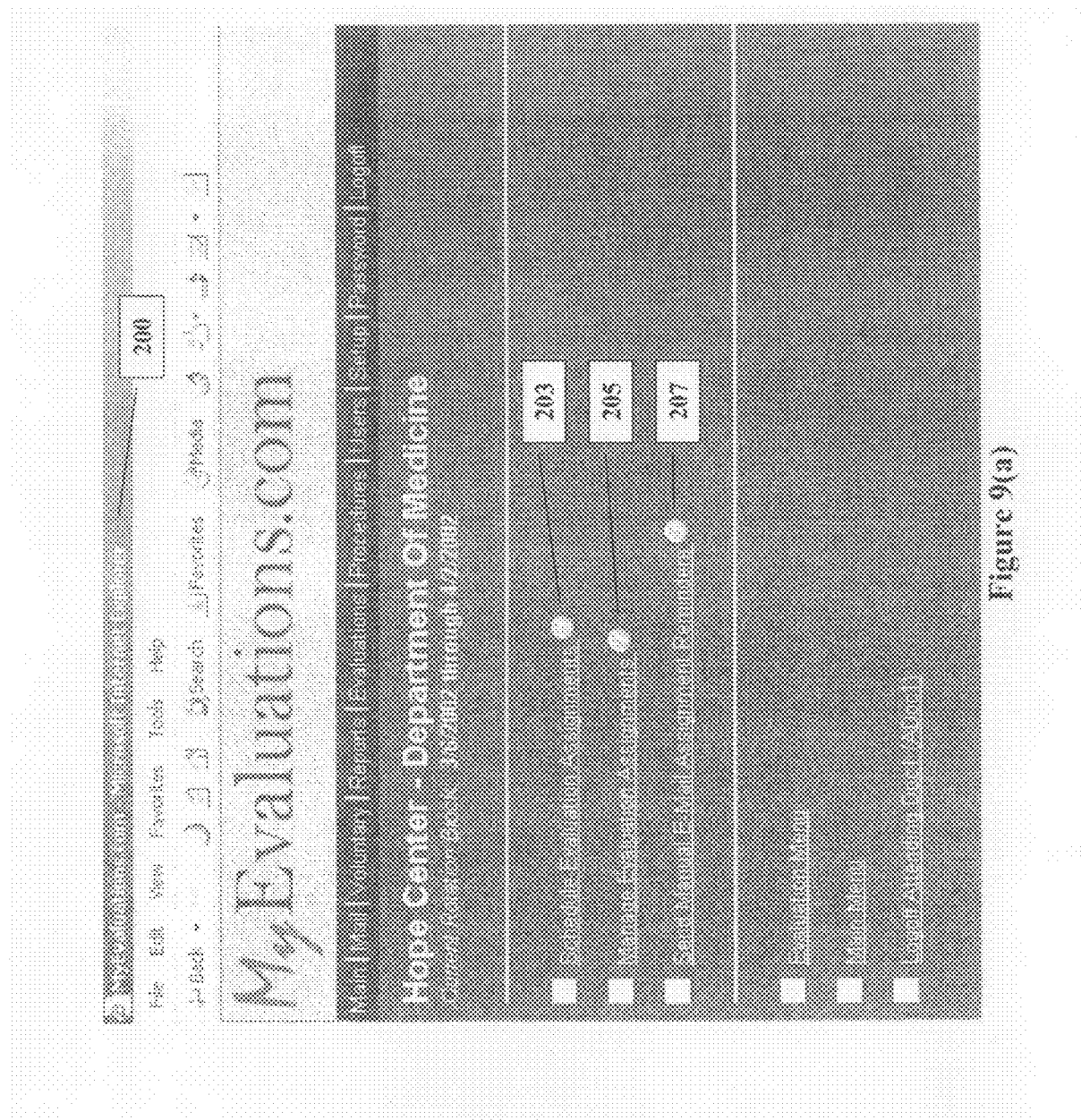
FIG. 9(a) illustrates an example Evaluation Assignments menu interface 200 and FIG. 9(b) illustrates example types of assignments available via the system.
Figure 9B:
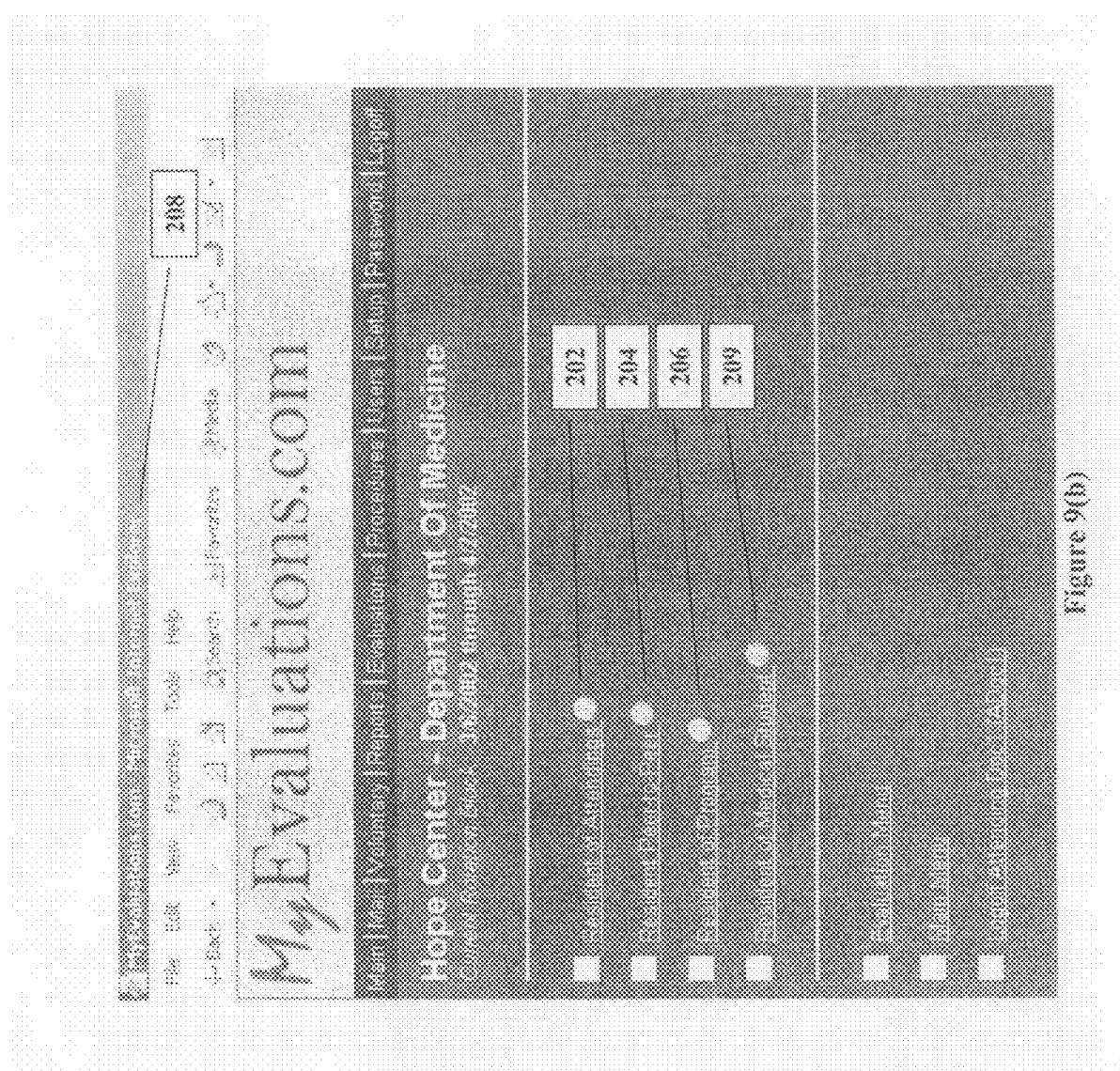

Returning to FIG. 7, from the build evaluations interface 110 the user may select an option 116 to assign evaluations completely on-line. In response to selecting option 116, the user is presented with a downloaded web-based interface 200 such as shown in FIG. 9(*a*) providing evaluation assignment mode functionality 203 for scheduling the assignment of an evaluation to residents or attendings, for example. Preferably, in response to selection of the schedule evaluation assignments functionality 203, an interface 208 is presented such as shown in FIG. 9(*b*) which illustrates the types of assignment evaluations to residents including: residents of attendings 202, peer-to-peer 204, e.g., resident of resident or attending of attending; residents of program 206; and, residents of medical students 209. Referring back to FIG. 9(*a*), the assignment scheduling process 203 enables assignment of evaluations to medical doctors, residents, nurses and fellows is preferably accomplished in a manner to provide 360 degree field of evaluations within the hospital environment, e.g., manually assigning evaluations to a group or to an individual, e.g., according to an individual's name, sub-specialty, or post-graduate year; assigning evaluations by a cycle, e.g., month, quarter, year, or a specific date or date range; monitoring pending evaluations and compliance; providing automatic e-mail notification of assignments; providing automatic e-mail reminders 207, e.g., of incomplete evaluations; and ability to provide users log on ability to complete an ad-hoc evaluation.

Figure 10:
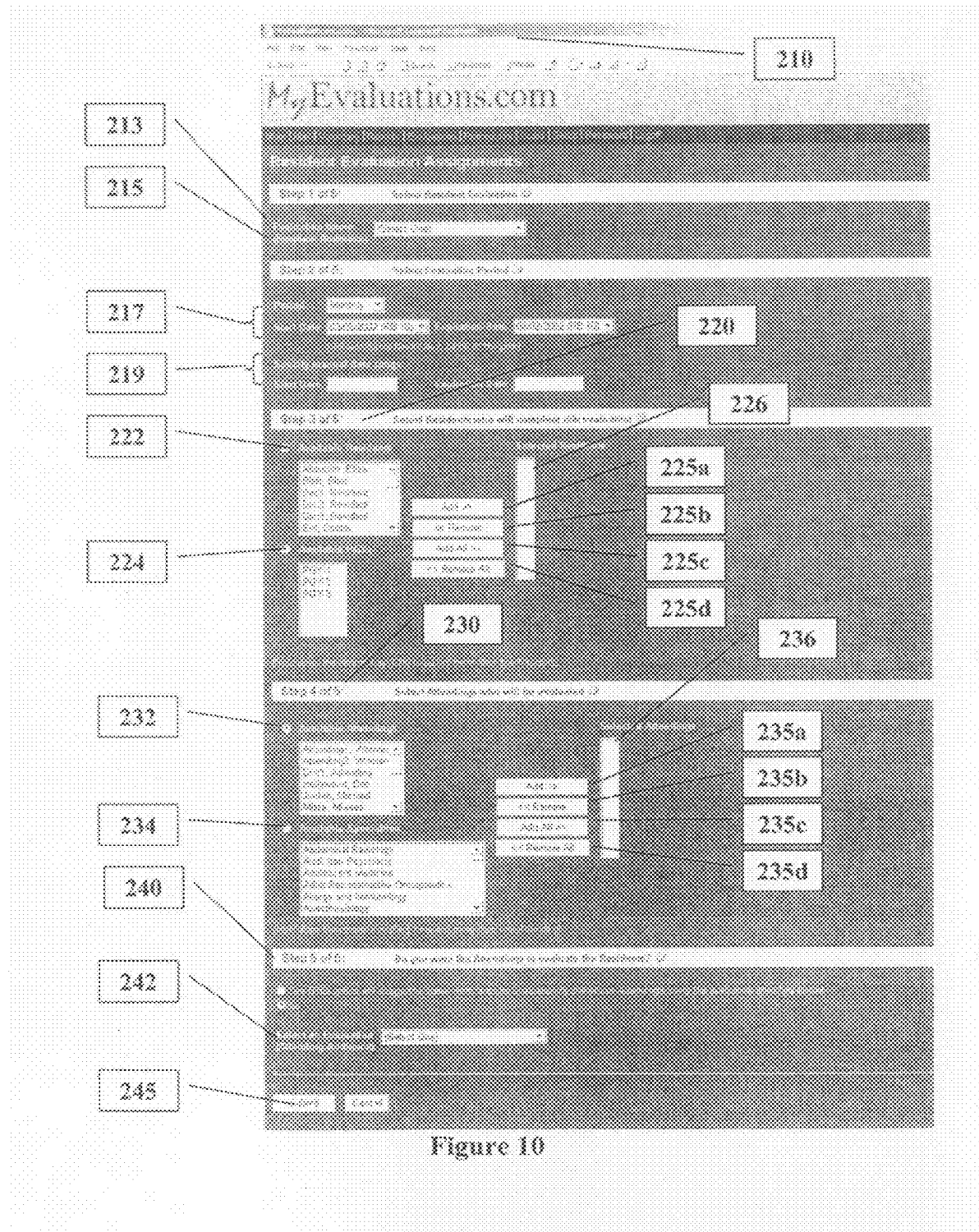
FIG. 10 illustrates an example Evaluation Assignment interface 210 downloaded to users for assigning an evaluation to residents, for example, who will be evaluating attending(s), and vice versa.

In an example implementation, in response to selection of the scheduling evaluation assignment option 203, a user may select the audience, e.g., a resident or attending. With respect to selection of Resident Assignments, the user's browser receives a web-based communication comprising an interface 210 as shown in FIG. 10 for effecting assignments of evaluations to residents. Likewise, selection of the Attending Assignments option will initiate a web-based download of an interface (not shown) for effecting assignment of evaluations to attendings. From the example interface 210 depicted in FIG. 10, functions are executed for specifying the assignment of an evaluation to Residents, for example, who will be evaluating attending(s).

In a first step, as shown in the interface of FIG. 10, a user first selects the category of evaluations 213, i.e., selecting the type of evaluation that will be assigned to the evaluator. This will be one of four major categories of evaluations as will be described: 1) 360° Evaluations; 2) Peer-to-Peer Evaluations; 3) Non-Peer; and 4) Program.

The 360° Evaluations type basically permits the assignment of evaluations to all individuals involved in the global delivery of patient care and medical education. This will include the Resident, Attending, Fellow, Nurse, and Medical Student. In addition, this module will facilitate the assignment of Self-Evaluations for cross-comparison to peers, supervisors, and subordinates. Initially, the administrator must select the "Focus Audience" to determine the person(s) that is being evaluated by all other in the 360° circle. After the Focus Audience is selected, there is a multi-step process for assigning an 360° evaluation. An example provided herein with respect to FIG. 10 focuses on the Resident as the Focus Audience.

Specifically, in the first step 213, the Evaluation Period and Rotation Name is selected via drop down menu 215. Then, in a second step, the user selects the date range to assign evaluations, e.g., either by selecting a range of dates based on the program's rotation blocks (RB) 217, or, may manually specify a start and end date in entry fields 219. In addition, the user may enter in an entry field, the name of rotation under consideration. In a third step 220, the user may select Residents who will be the Focus Audience, i.e., who complete the evaluation. Preferably, the residents may be selected by name or by post-graduate year (PGY). The selected individuals will be the focus of all assigned evaluations.

Specifically, in view of FIG. 10, the "Available Residents" list 222 includes the names all residents currently available through MYEVALUATIONS.COM for the particular hospital/department. Names may be added or deleted from by returning to the "Main Menu" and selecting the option "Manage User Profiles" as described herein. It should be noted that Residents who are included in the "Manage User Profiles" list, but who have completed their PGY term, will not appear in this list. Further, an "Available PGYs" list 224 is displayed to include all post-graduate years (PGYs) available to the Department (e.g. Internal Medicine will have PGY-1 through PGY-3). This option thus enables the selection of a group of residents from the desired PGY. To select this option, the user selects the radio button next to "Available PGYs" and select as many PGYs as needed. As further shown in FIG. 10, Add 225*a*, remove 225*b*, Add All 225*c* and Remove All 225*d* selection blocks are provided to enable the respective moving of the selected name(s) or PGYs from the Available box to the "Selected Residents" box 226, the move of the selection(s) from the "Selected Residents" box to the Available box, the addition of all the names or PGYs from the Available box to the "Selected Residents" box, or the deletion of all the names from the Available box to the "Selected Residents" box.

In a fourth step 230, the Attending(s) who is/are subject of the evaluation are selected by name or by specialty. Thus, an "Available Attendings" list 232 may be displayed which provides the names all attendings currently available through MYEVALUATIONS.COM. Addition or deletion of names from this list may be performed via the "Manage User Profiles" option of the "Main Menu" (FIG. 4). This option may be used to select a group of attendings according to name. A further "Available Specialties" list 234 is also presented which provides the names all specialties currently available to the department. This option may be used to select a group of attendings from the desired Specialty by marking a radio button next to "Available Specialties" and selecting as many specialties as needed. As in the selection of Available Residents, Add 235*a*, remove 235*b*, Add All 235*c* and Remove All 235*d* function blocks are provided to enable the respective selection or removal of the selected Attending(s)/specialties name(s) to the "Selected Attendings" box 236.

In a fifth step 240, the option is provided for enabling an evaluation to be assigned in the other direction, e.g., attendings to evaluate residents. This may be accomplished in the manner specified in accordance with the functions provided in steps 3 and 4. However, in this instance, attendings who will be the evaluators are selected, and residents to be evaluated, are selected. The particular evaluation may be selected via the drop down menu 242 in FIG. 10.

It is understood that Nurses may complete this evaluation and may be selected by name or by specialty. The selected individuals will complete evaluations on resident/s specified in the second step of FIG. 10. An "Available Nurses" list (not shown) may be displayed which provides the names all the nurses currently available through MYEVALUATIONS.COM with addition/deletion of names provided via the "Manage User Profiles" option from the main menu. Additionally, the same features of step three for Attendings may be applied to select the Fellow/s by name or by specialty. The selected individuals will complete evaluations on resident/s specified in the second step. Similarly, the same features of step three for Attendings may be applied to select the Medical students who will complete this evaluation on resident/s specified in step two, for example.

The Peer-to-Peer category focuses on assigning evaluations from the target audience to others in the same target audience group, for example, residents evaluating other residents. This comprises a 5-step process for assigning an evaluation to an individual or group of resident(s). A first step comprises selecting the evaluation to be used by the resident (s) to evaluate other resident(s). In a second step, the date range to assign evaluations is selected, as step 2 of FIG. 10. That is, a range of dates based on the program's rotation blocks (RB) may be selected, or manual start and end dates may be specified. In a third step the resident(s) who will be assigned the evaluation are selected by name or by postgraduate year (PGY). The selected individuals is taken from the "Available Residents" list which has the names all residents currently available through MYEVALUATIONS.COM. It is understood that Residents who are included in the "Manage User Profiles" list, but who have completed their PGY term, may not appear in this list. An "Available PGYs" list is provided to include all post-graduate years (PGYs) available to the Department (e.g. Internal Medicine will have PGY-1 through PGY-3) and selection of a group of residents from the desired PGY may be alternately performed. In a fourth step, the Resident(s) to be evaluated are selected by name or by post-graduate year (PGY). The selected individuals will be evaluated by the resident(s) specified in the third step.

The Non-Peer category focuses on including any target audience evaluating another (different) target audience. For example, Residents evaluating Attendings. This also may comprise a 5-step process for assigning an evaluation to an individual or group of resident(s). A first step involves Selecting a Resident Evaluation to be used by the resident(s) to evaluate the attending(s). A step two involves selecting an evaluation period, e.g., a date range to assign evaluations which may comprise a range of dates based on the program's rotation blocks (RB), or specify manual start and end dates. A third step involves selecting those Residents, for example, who will complete this evaluation, e.g., selected according to name or by post-graduate year (PGY). The selected individuals will be assigned the evaluation and may be selected from the "Available Residents" list or the "Available PGYs" list The next step involves selecting those attending(s) who are to be evaluated, e.g., either by name or by specialty. The selected individuals will be evaluated by the resident(s) specified in Step three either through the "Available Attendings" list or the "Available Specialties" list as described herein. An optional timesaving step for assigning the above Resident(s) for evaluation by the above Attending(s) using a specified evaluation may additionally be performed, if selected, or otherwise, only the Resident(s) will be evaluating Attending(s).

The Program category focuses on the assignment of the target audience to evaluations unrelated to another target audience, e.g., residents evaluating the cafeteria. Thus, in a first step, the evaluation to be used by the resident(s) to evaluate the Program is selected. Then, the date range to assign evaluations based on the program's rotation blocks (RB), or manual start and end dates is specified. Thirdly, the Residents who will complete this evaluation are selected in the manner as described herein (e.g., by name or by postgraduate year (PGY)).

In sum, from the exemplary interface 210 of FIG. 10, once the category has been selected and the various steps followed, the administrator may then press Submit 245 in order to schedule and assignment. By pressing the Submit button located at the bottom of each submission page (FIG. 10), the system instantly and automatically send an e-mail notification of a new assignment to each person selected in the target audience field.

Figure 11:
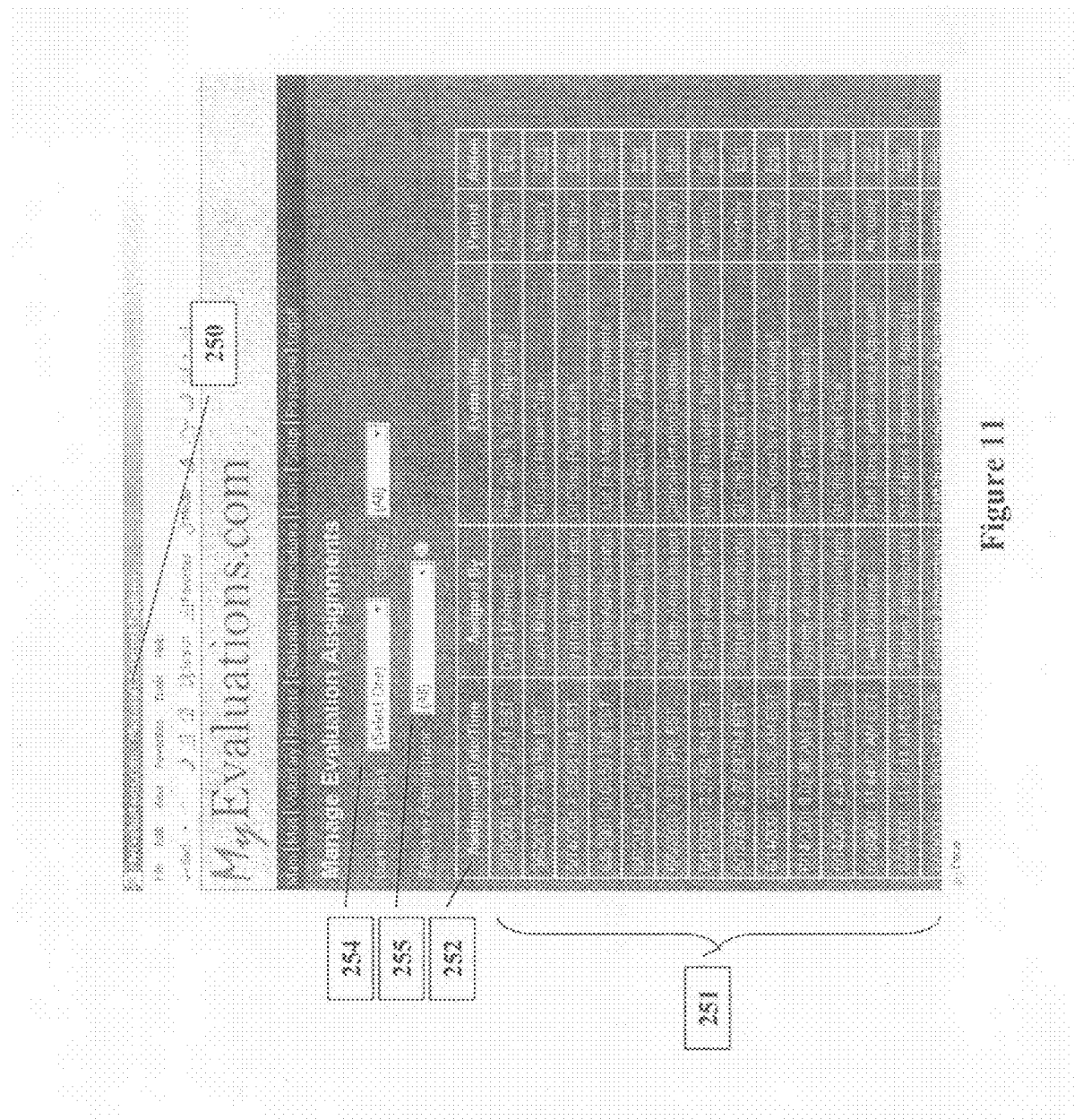
FIG. 11 illustrates an example Manage Evaluation Assignments interface 250 for enabling the management of previously assigned evaluations.

Referring back to FIG. 9(*a*), in a further example implementation, selection of the Manage Evaluation Assignments option 205 from the Evaluation Assignments menu 200 provided in FIG. 9(*a*) will result in the web-based download of an interface 250 shown in FIG. 11 for enabling the Management of previously assigned evaluations. Specifically, as shown in FIG. 11, functionality is provided from this screen, to enable users to sort through the list of assignments and delete previous assignments, or, to enable users to delete an individual or a group of assignments. As shown in FIG. 11, an evaluation assignment may be selected by the name of assignee, date assigned, or by the name of the person having made the assignment. The administrator is presented with a table of assignments 251 listing all evaluation assignments 252 sorted from top to bottom by order of submission date. A user/administrator may select a name from a "Look-up by Name" option 254 in order to find the name of a current user and display all evaluations assigned to and pending on the selected person. Otherwise, the "Select an Administrator" option 255 may be used in order to find all evaluations assigned by a specific administrator. In all instances the administrator is given the option to Edit or Delete a specific assignment from the table. Deleting an assignment will completely remove it from the database of assignments pending.

Figure 12:
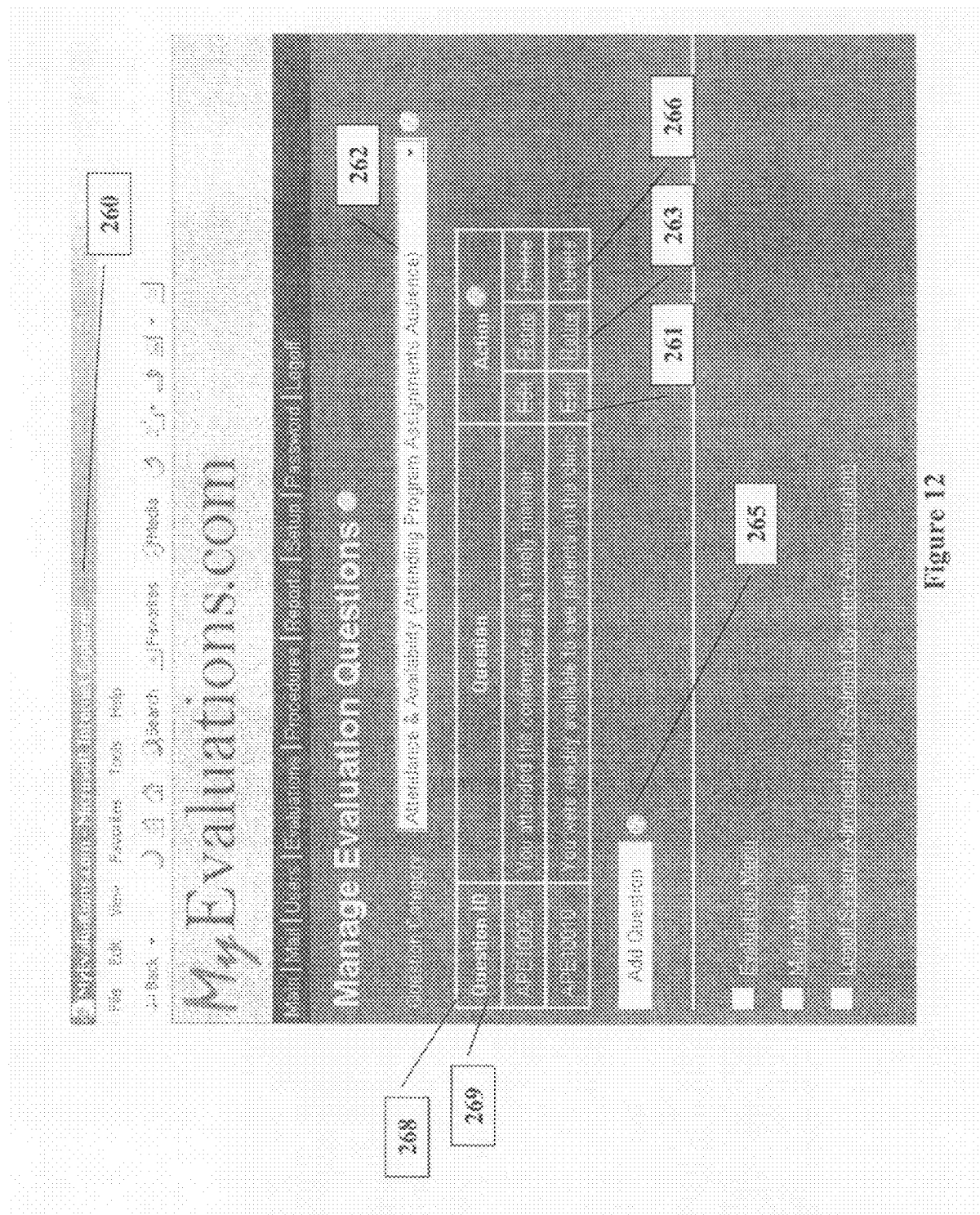
FIG. 12 illustrates an example Manage Evaluations Questions interface 260 for enabling the maintenance and addition of questions pertaining to competencies that may be selected to comprise an evaluation.
Figure 13:
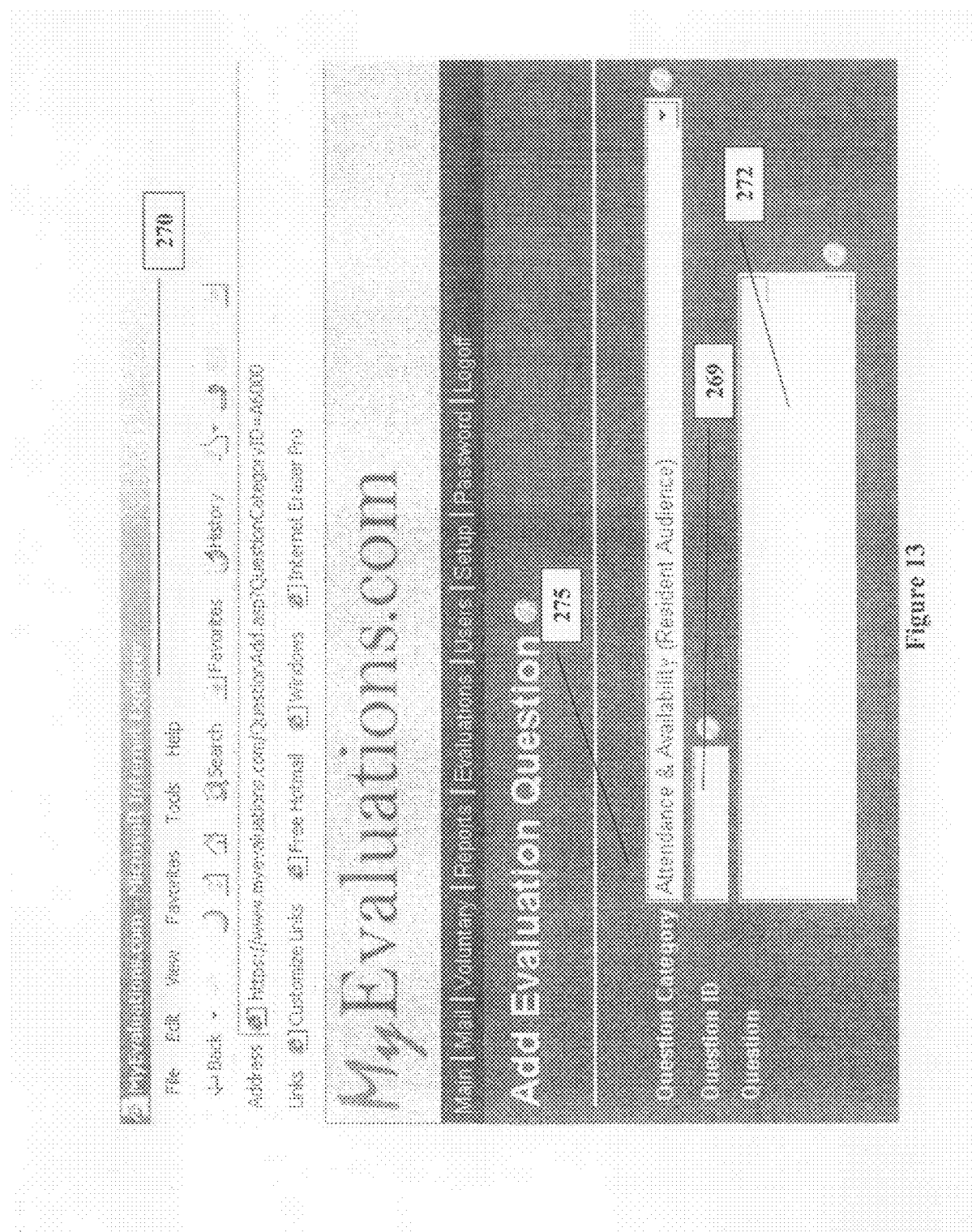
FIG. 13 illustrates a web-based interface display 270 providing functionality for adding an evaluation question to the evaluation questions database 18a of FIG. 1.

Returning to the Evaluations Build interface 100 of FIG. 7, the user may select an option 118 to manage the questions database 18*a* of FIG. 1 which initiates the downloading of a Manage Evaluations Questions interface 260 as shown in FIG. 12. Specifically, FIG. 12 illustrates the mechanism for Adding 261, Deleting 263 or retiring 266 questions to and from the library of on-line evaluation questions. Questions are identified by question Ids 269 in a table 268 and categorized by competencies for each target audience and category in the medical profession. For instance, as shown in FIG. 12, the user will first select a category from the pull-down menu 262 of questions categories, i.e. competencies. The competencies include, but are not limited to: Core Competencies including those relating to Patient Care; Medical Knowledge; Interpersonal and Communication Skills; Professionalism; Practice-Based Learning And Improvement; and, Systems-Based Practice; and, secondary Competencies including those relating to: Availability; Clinical Judgment; Clinical Skills; Enthusiasm and Responsiveness; Humanistic Qualities; Medical Care; Moral and Ethical Behavior; Personality; Responsibility; and, Teaching Skills. It should be understood that the question types may be directed to any of the target audiences including Residents, Attendings, Medical Students, Fellows, and Nurses covering any of the evaluation categories, e.g., Peer-to-Peer, Non-Peer, Program, etc. In the preferred embodiment, each new department/client is setup with a default set of evaluation questions for their question database. As further shown in FIG. 12, the user may select the Add Question option 265 which initiates download of a web-based display an example display 270 which is shown in FIG. 13 including entry fields for enabling the addition of one or more questions 272 and associated question IDs 269 pertaining to a selected question category 275, i.e., core or secondary competency.

Report Generation

Figure 14:
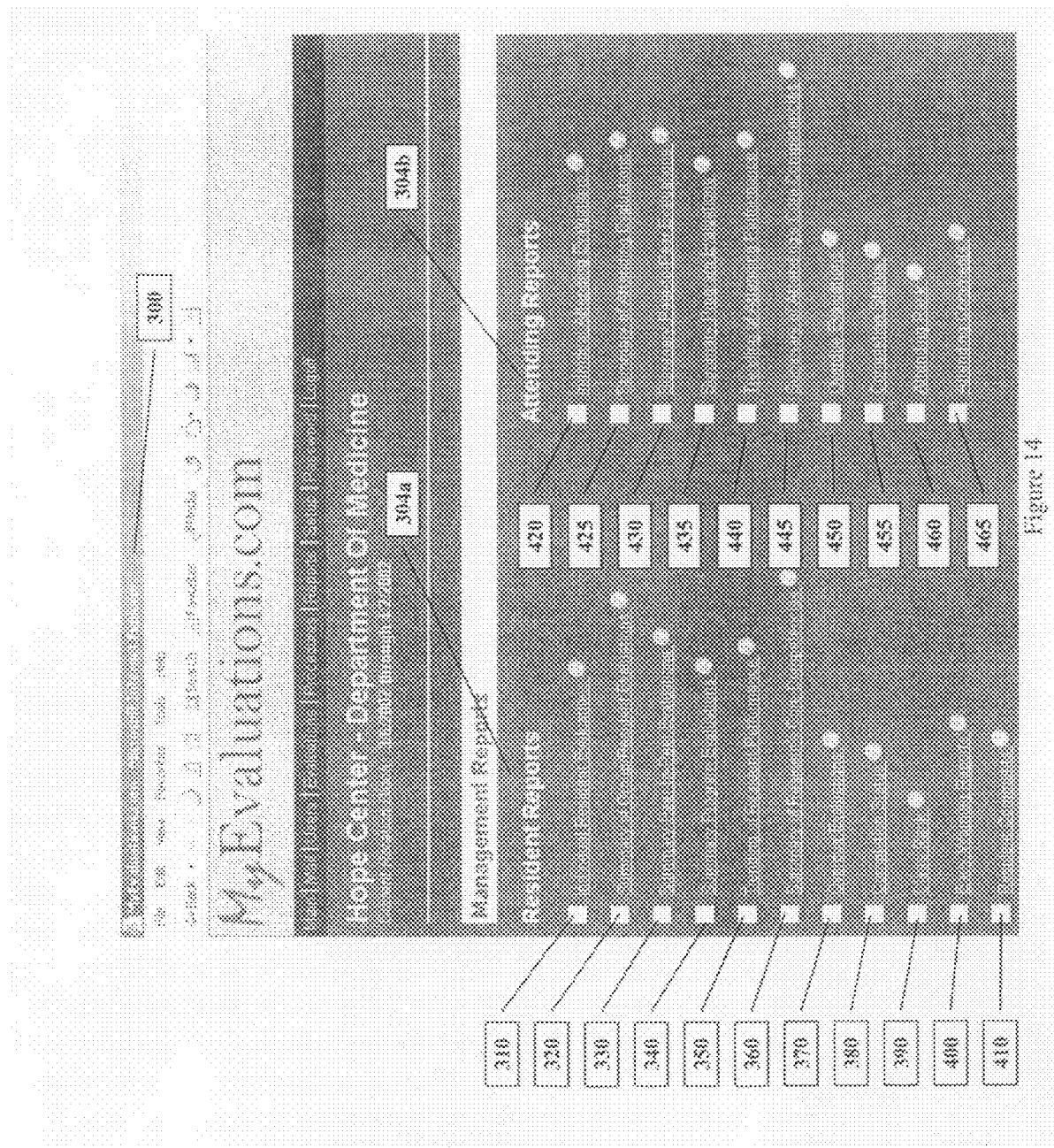
FIG. 14 illustrates an example Reports Selection interface 300 for initiating real-time, on-line generation of various management reports.

From the main menu interface 60,70 of FIGS. 3(a) and 3(b), a user/administrator may initiate the complete on-line/web-based generation of a report based on the data collected via the online evaluations by selecting the Reports option 65 which initiates presentation of a Reports Selection interface 300 such as shown in FIG. 14. As part of this functionality, implemented by the reports generation module 27 of FIG. 1, a user may generate clear, concise, and comprehensive on-line reports from the data collected and, additionally, facilitate tracking of medical doctor, resident, nurse and fellow completion of evaluations. In collecting data from evaluations, the on-line reporting feature is an important and indispensable feature. Each group evaluated will have a unique set of evaluation reports.

From the interface 300 of FIG. 14 there are provided report lists 304a, 304b for residents and attendings, respectively. All reports for Residents, Medical Students, Fellows and Nurses will have the same format. In describing each report, the appropriate group is substituted in each description. Some of the reports that may be generated on-line for residents include: 1) Individual Resident Evaluations 310; 2) Summary of Group/Resident Evaluations 320; 3) Summary Peer-to-Peer Evaluations 330; 4) Summary Program Evaluations 340; 5) Trending of Resident Performance 350; 6) Summary of Resident's Core Competencies 360; 7) Overdue Evaluations 370; 8) Completion Status 380; 9) Class Rank 390; and 10) Early Warning Reports 400 and Resident Comments 410.

Figure 15A:
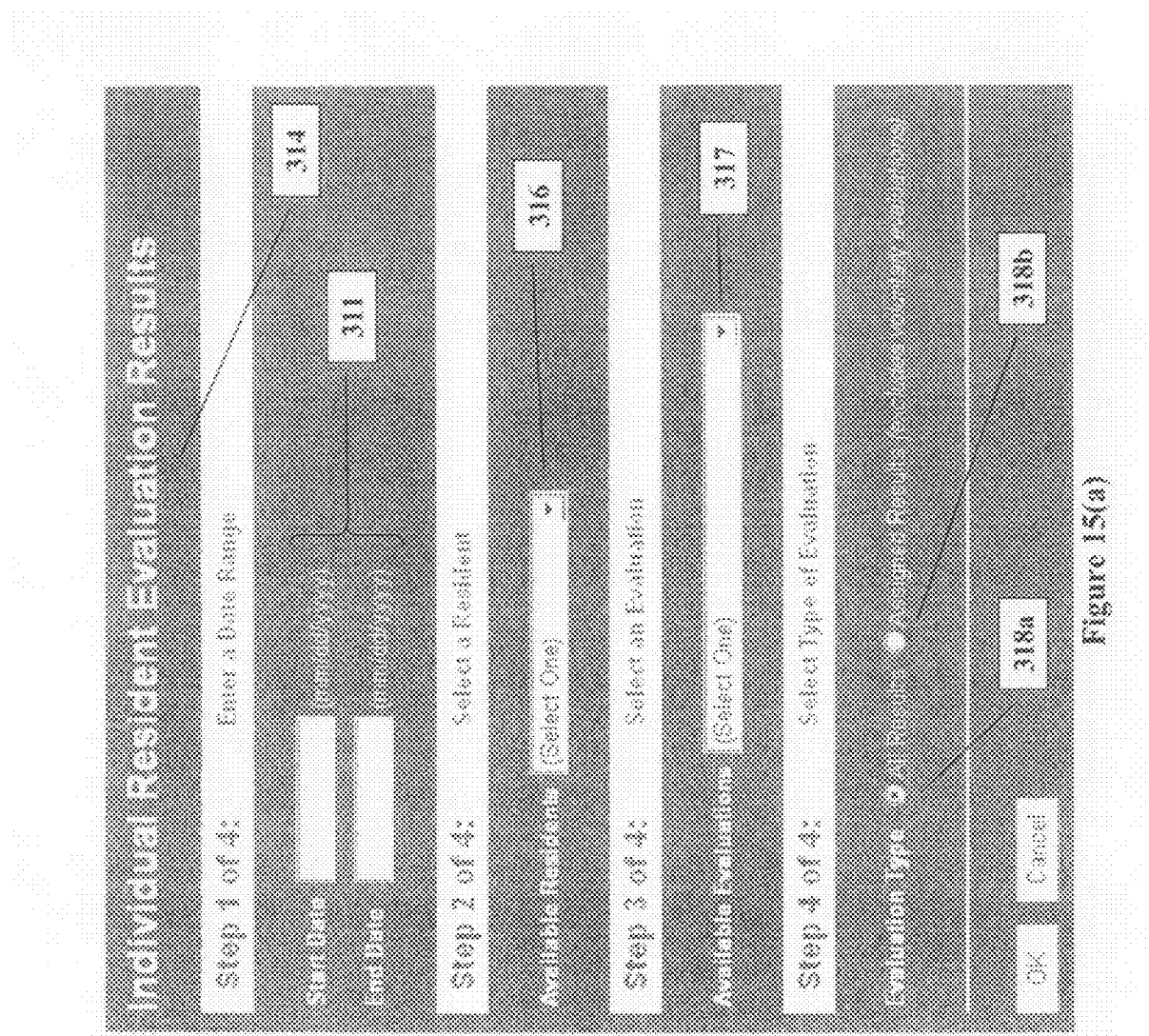
FIG. 15(a) illustrates an example Individual Resident Evaluations report interface 314 providing functionality for on-line generation of an Individual Resident Evaluations report 312 an example of which is depicted in FIG. 15(b)
Figure 15B:
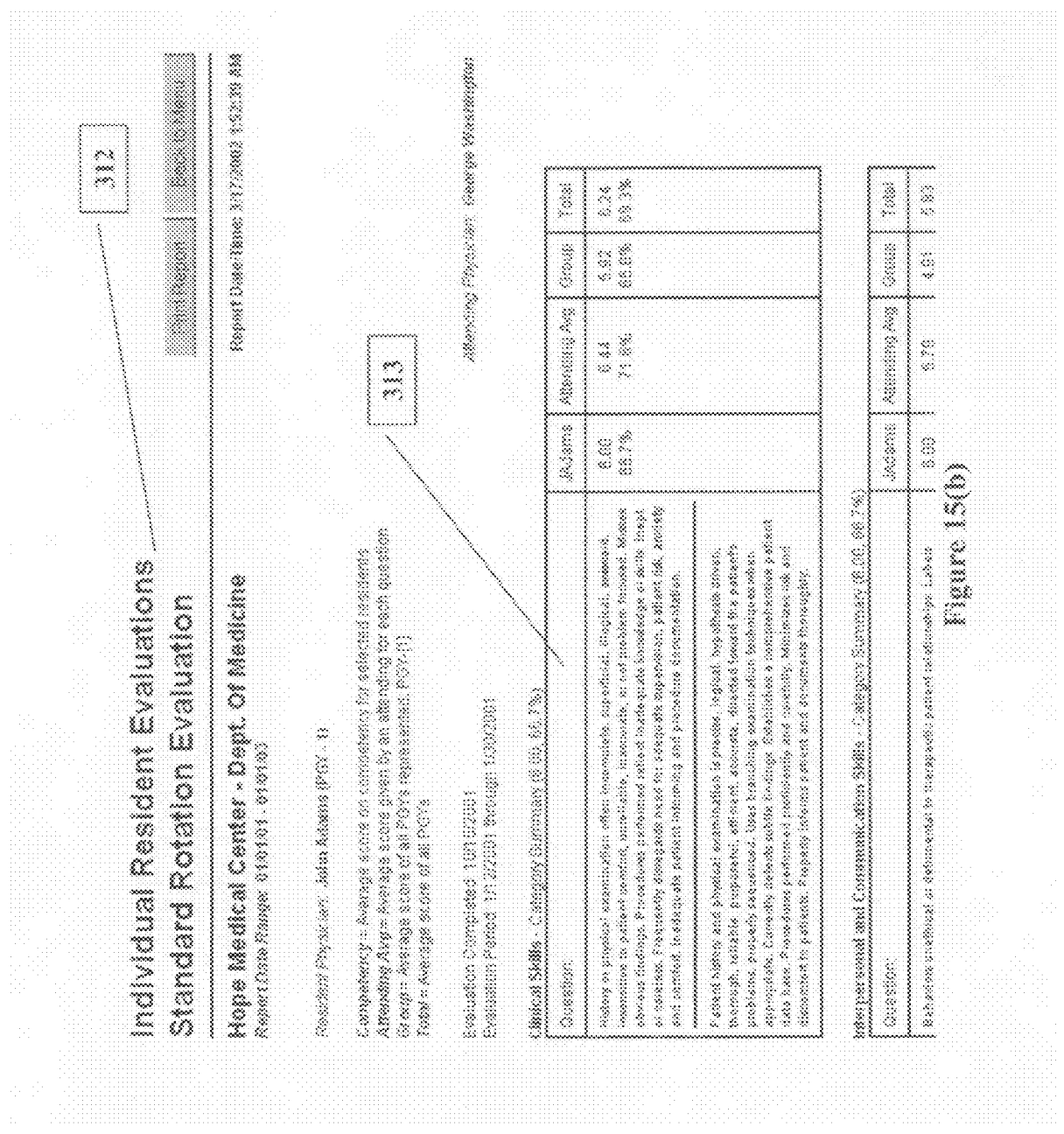

When selected, the Individual Resident Evaluations report 310 initiates functionality for generating a detailed report on an individual's evaluation performance. An example Individual Resident Evaluations report 312 is shown in FIG. 15(b) wherein each evaluation is listed separately, including a table 313 providing the questions, scores and comments. Each score is compared to the person's peers in the same group (Group score, e.g., PGY or Specialty) and also to all (Total score). When attendings are the evaluator there will be an additional column listing the Attending's average score for the specific and the selected date range. The last page of the report may include a statistical analysis summarizing the "n" value, mean, median, variance, high and low (not shown). To provide this functionality, a web-based communication such as the Individual Resident Evaluations report interface 314 shown in FIG. 15(a) is provided. As shown in FIG. 15(a), for generating this report, there are four selection criteria including: 1) entry fields 311 for the entry of a start and end date range; 2) pull-down menu 316 for the selection of a Resident, e.g., by choosing a name from the list of all residents; 3) pull-down menu 317 for the selection of an Evaluation, e.g., by choosing one evaluation from the list of all evaluations; and 4) selecting the type of Evaluation including a radio button option 318a, for selecting "All Results" (default) to include all the reported data for the selected resident including results from evaluations completed voluntarily and those assigned by the Program, for example; and a radio button option 318b for selecting an "Assigned Results" to include only data from assigned evaluations. This option excludes results from evaluations completed voluntarily.

Figure 16A:
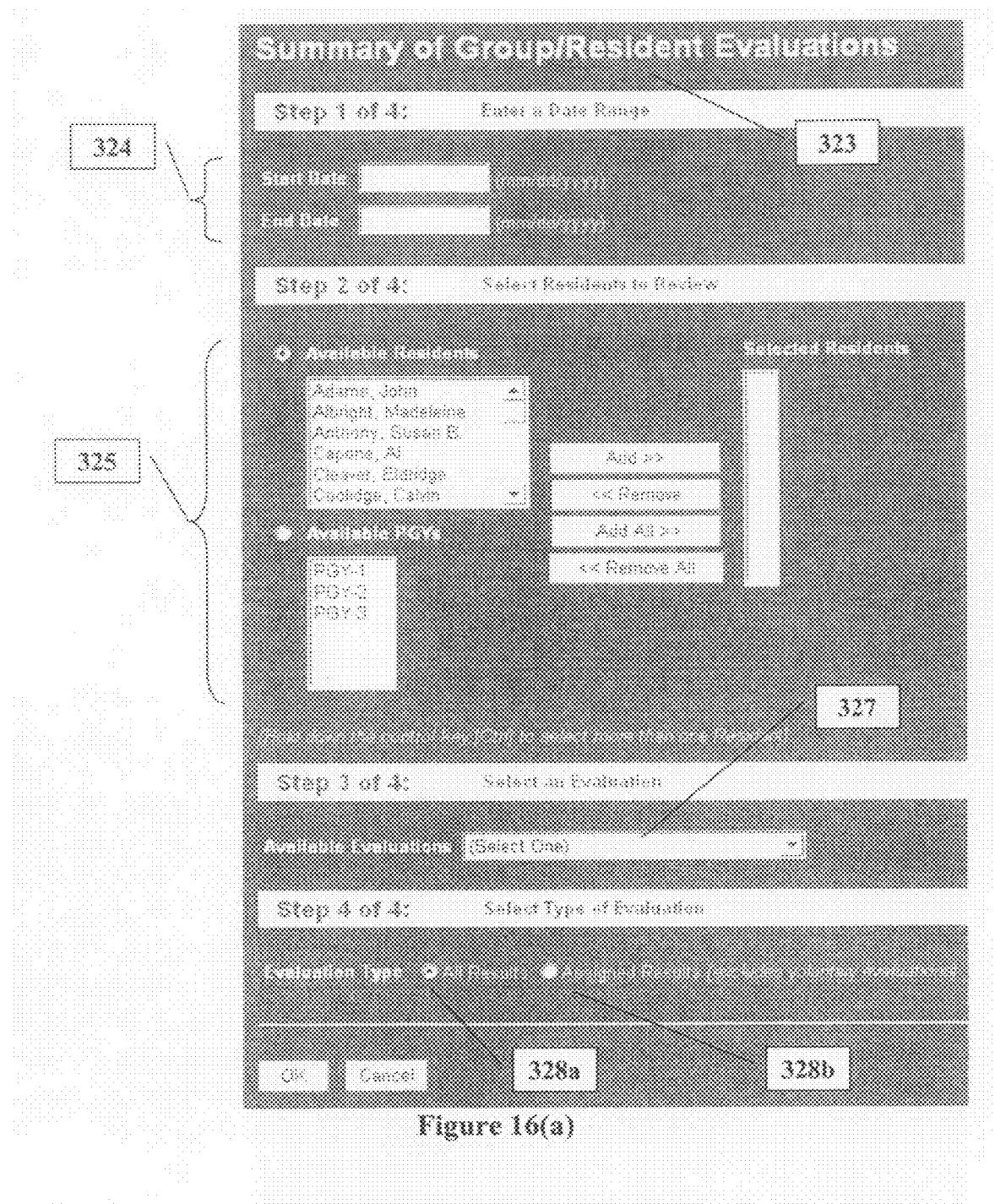
FIG. 16(a) illustrates an example Summary of Group/Resident Evaluations report interface 323 providing functionality for on-line generation of a Summary of Group/Resident Evaluations report 321 an example of which is depicted in FIG. 16(b)

When selected from FIG. 14, the Summary of Group/Resident Evaluations report 320 initiates functionality for generating a detailed summary attending evaluation report on an individual or group of selected residents. An example Summary of Group/Resident Evaluations report 321 is shown in FIG. 16(b) wherein each evaluation is listed separately, including a table 322 which includes summary data on each selected resident, in reference to each evaluation question. The results are compared to the residents' peers in the same PGY (Group score) and to all residents (Total score) including a last page (not shown) which includes the statistical analysis, summarizing the n value, mean, median, variance, high and low values. To provide this functionality, a web-based communication such as the Summary of Group/Resident Evaluations report interface 323 shown in FIG. 16(a) is provided. As shown in FIG. 16(a), for generating this report, there are four selection criteria including: 1) entry fields 234 enabling the entry of a start and end date range; 2) a mechanism 325 for selecting residents to review including Add, Add All, Remove, Remove All functionality for choosing residents as described herein, particularly by selection of a name, for example, from the list of Available Residents or selecting residents based on PGY level, by pointing and clicking on a desired name(s) or PGYs and then selecting "Add>>" button to select the name(s); or, selecting all residents names from the list of Available Residents by clicking the "Add All>>" to select all the names. Further functionality for removing some or all of the selected residents names is provided; 3) a pull-down menu 327 for enabling the selection of an Evaluation, e.g., by choosing one evaluation from the list of all evaluations; and 4) selecting the type of Evaluation including a radio button option 328a, for selecting "All Results" (default) to include all the reported data for the selected resident including results from evaluations completed voluntarily and those assigned by the Program, for example; and a radio button option 328b for selecting an "Assigned Results" to include on data from assigned evaluations. This option excludes results from evaluations completed voluntarily.

Figure 17A:
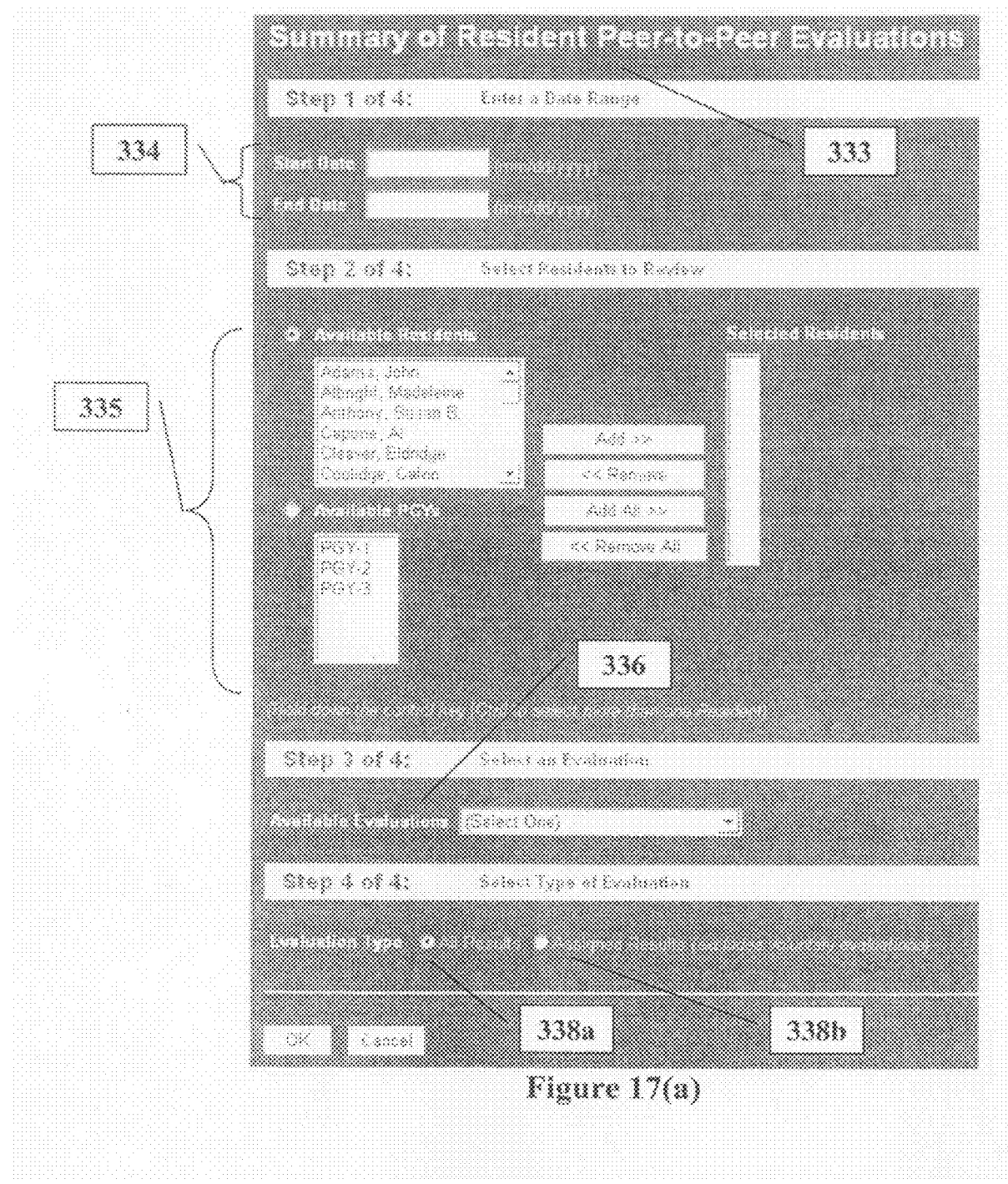
FIG. 17(a) illustrates an example Summary Peer-to-Peer Evaluations report interface 333 providing functionality for on-line generation of a Summary Peer-to-Peer Evaluations report 331 an example of which is depicted in FIG. 17(b)
Figure 17B:
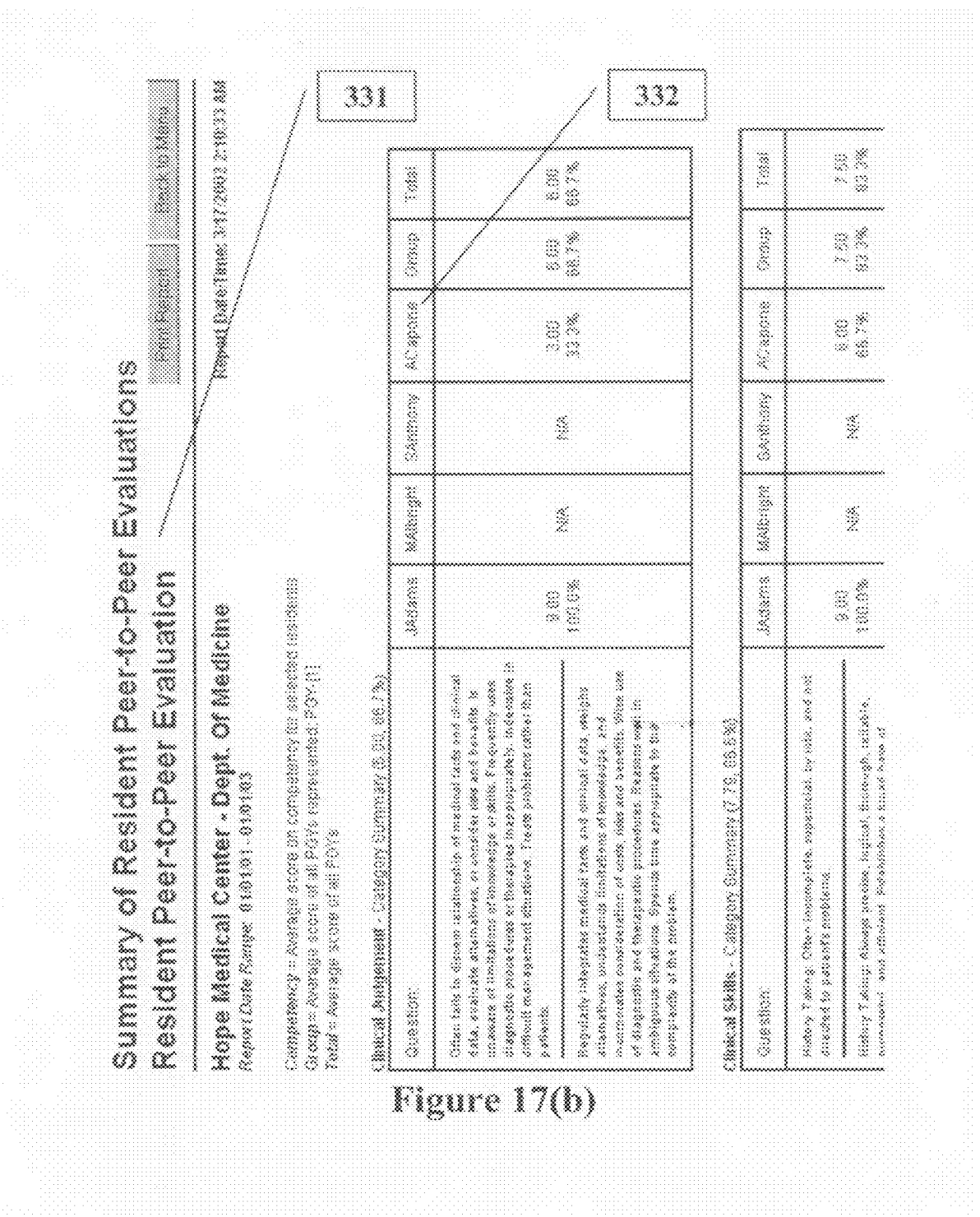

When selected from FIG. 14, the Summary Peer-to-Peer Evaluations report 330 initiates functionality for generating a detailed summary attending evaluation report on an individual or selected residents (e.g., by PGY). An example Summary Peer-to-Peer Evaluations report 331 is shown in FIG. 17b) which includes summary data 332 on each selected resident in reference to one or more evaluation questions. The results are compared to the residents' peers in the same PGY (Group score) and to all residents (Total score). Also included is a summary of anonymous comments written by peers on the selected residents. Comments are reported anonymously without reference to author, date, time or rotation. The last page of the report includes a statistical analysis summarizing the "n" value, mean, median, variance, high and low values. To provide this functionality, a web-based communication such as the Summary Peer-to-Peer Evaluations report interface 333 shown in FIG. 17(a) is provided. As shown in FIG. 17(a), for generating this report, there are four selection criteria including: 1) entry fields 334 enabling the entry of a start and end date range; 2) a mechanism 335 for selecting residents to review including Add, Add All, Remove, Remove All functionality for choosing residents as described herein, particularly by selection of a name, for example, from the list of Available Residents or selecting residents based on PGY level, by pointing and clicking on a desired name(s) or PGYs and then selecting "Add>>" button to select the name(s); or, selecting all residents names from the list of Available Residents by clicking the "Add All>>" to select all the names. Further functionality for removing some or all of the selected residents names is provided; 3) a pull-down menu 336 for enabling the selection of an Evaluation, e.g., by choosing one evaluation from the list of all evaluations; and 4) selecting the type of Evaluation including a radio button option 338a, for selecting "All Results" (default) to include all the reported data for the selected resident including results from evaluations completed voluntarily and those assigned by the Program, for example; and a radio button option 338b for selecting an "Assigned Results" to include on data from assigned evaluations. This option excludes results from evaluations completed voluntarily.

Figure 18A:
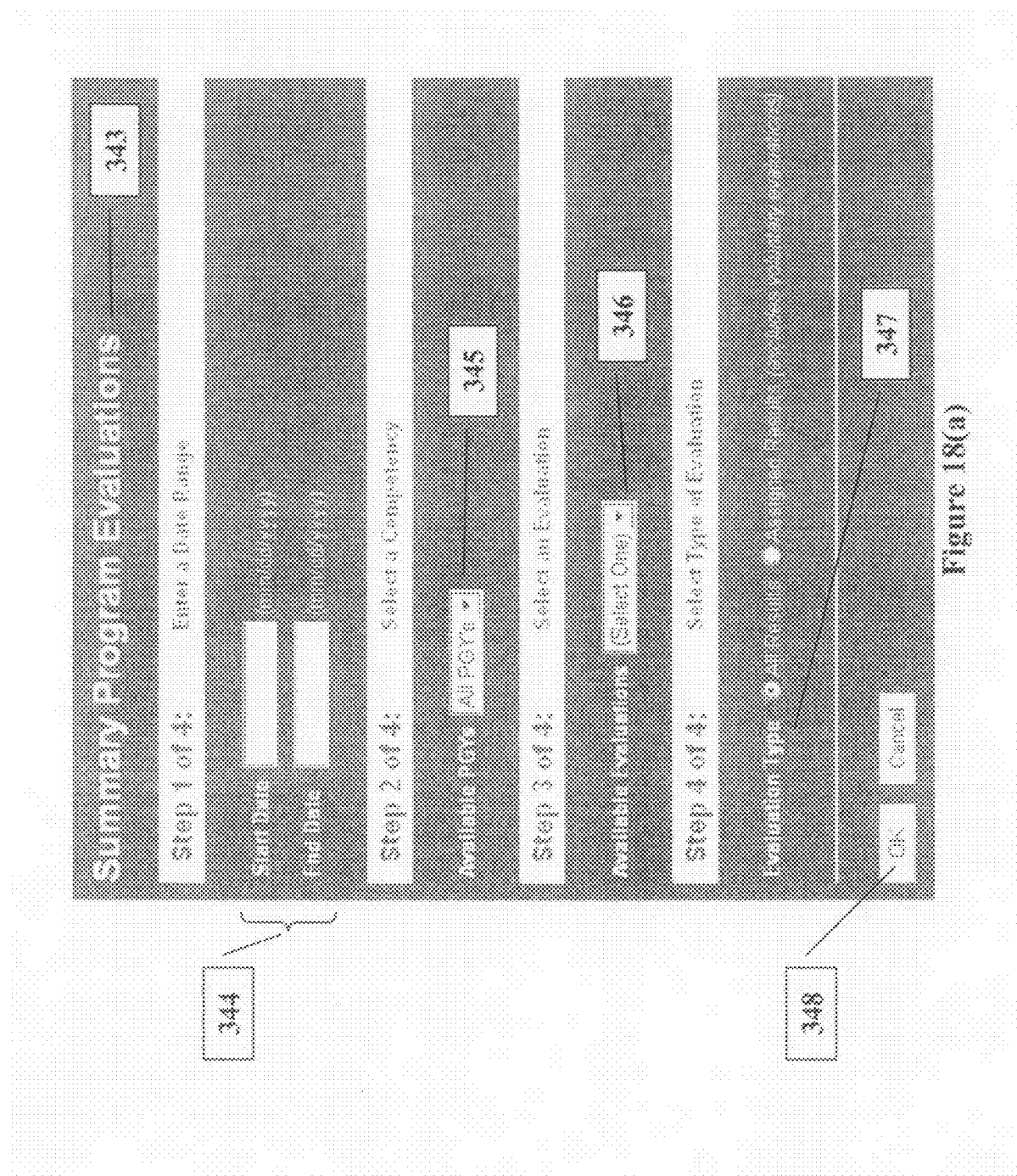
FIG. 18(a) illustrates an example Summary Program Evaluations report interface 343 providing functionality for on-line generation of a Summary Program Evaluations report 341 an example of which is depicted in FIG. 18(b)
Figure 18B:
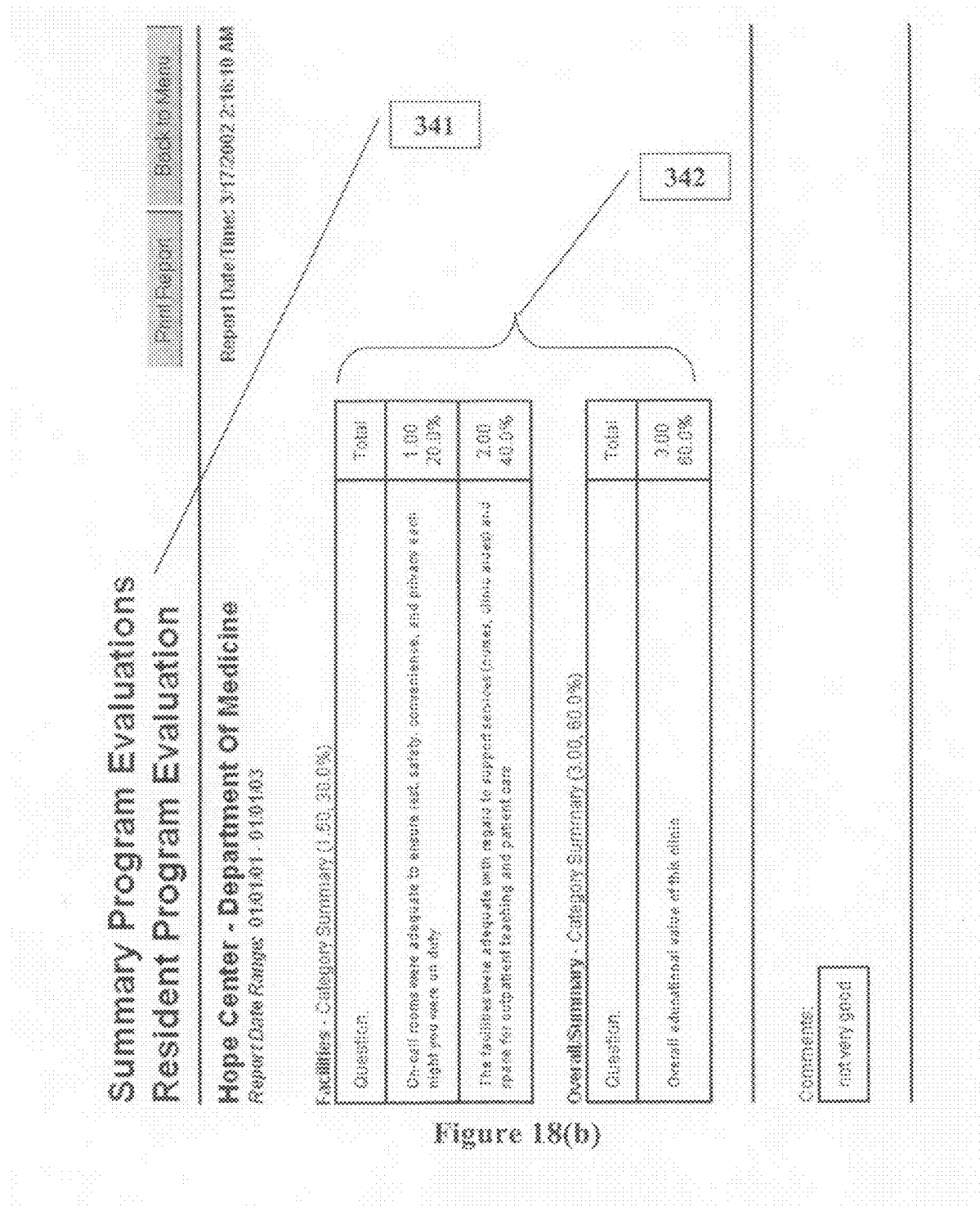

When selected from FIG. 14, the Summary Program Evaluations report 340 initiates functionality for generating a detailed Summary Program evaluation report from the perspective of selected residents (e.g., by PGY). An example Summary Program evaluation report 341 is shown in FIG. 18(*b*) which includes summary data 342 on selected PGY(s), in reference to each evaluation question. Also included is a summary of anonymous comments written by each resident. To provide this functionality, a web-based communication such as the Summary Program evaluation report interface 343 shown in FIG. 18(*a*) is provided. As shown in FIG. 18(*a*), for generating this report, there are four selection criteria including: 1) entry fields 344 enabling the entry of a start and end date range; 2) a mechanism 345 for selecting a PGY by choosing "All PGYs" to include all residents; otherwise, choosing a specific PGY in order to restrict the search to one group (PGY); 3) a pull-down menu 346 for enabling the selection of an Evaluation, e.g., by choosing one evaluation from the list of all evaluations; and 4) selecting the type of Evaluation including a radio button option 347, for selecting "All Results" (default) to include all the reported data for the selected resident including results from evaluations completed voluntarily and those assigned by the Program, for example; and a radio button option 348 for selecting an "Assigned Results" to include on data from assigned evaluations. This option excludes results from evaluations completed voluntarily.

Figure 19A:
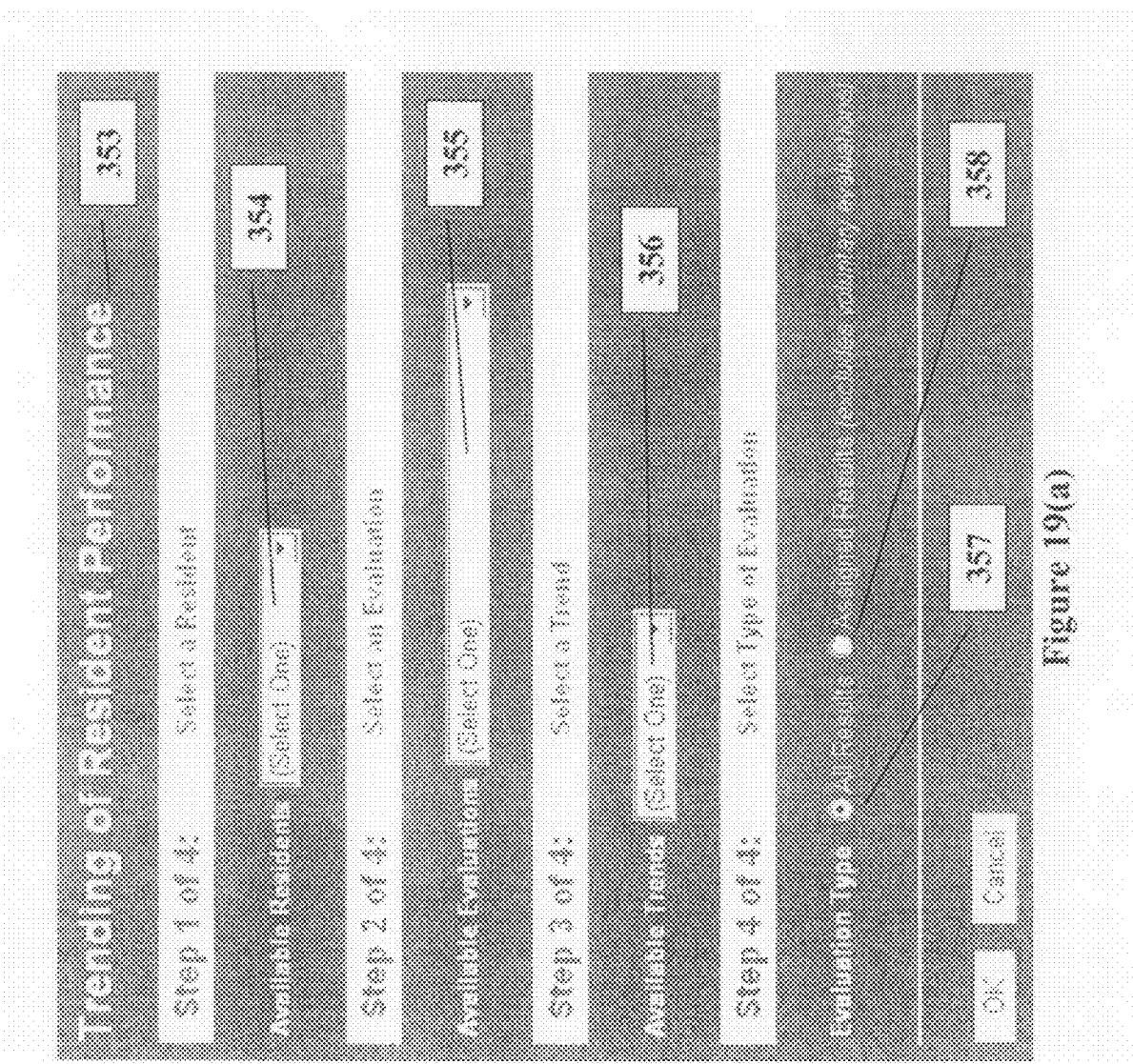
FIG. 19(a) illustrates an example Trending of Resident Performance report interface 353 providing functionality for on-line generation of a Trending of Resident Performance report 351 an example of which is depicted in FIG. 19(b)
Figure 19B:
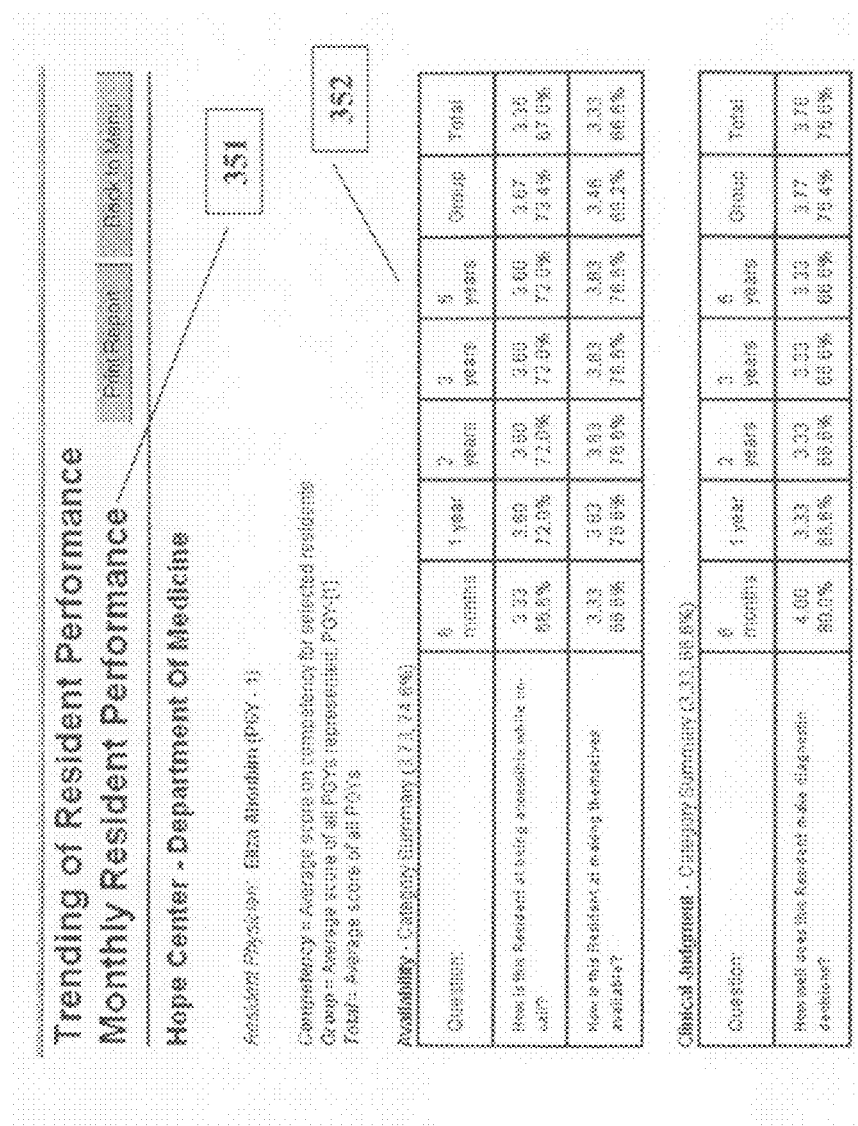

When selected from FIG. 14, the Trending of Resident Performance report 350 initiates functionality for generating a detailed trending report on an individual resident's performance over the course of time (e.g., 6 months to 5 years). Trending is limited to a single resident and a single evaluation. An example Trending of Resident Performance report 351 is shown in FIG. 19(*b*) which charts an individual resident's performance 352 over the course of time. To provide this functionality, a web-based communication such as the Trending of Resident Performance evaluation report interface 353 shown in FIG. 19(*a*) is provided. As shown in FIG. 19(*a*), for generating this report, there are four selection criteria including: 1) a pull-down menu 354 for enabling the selection of a Resident chosen from a list of all residents; 2) a pull-down menu 355 for enabling the selection of a Evaluation chosen from a list of all evaluations; 3) a pull-down menu 356 for enabling the selection of a trend chosen from time periods such as 6-month, or 1-year up to 5-years; and 4) selecting the type of Evaluation including the radio button options 357, 358 such as described herein with respect to FIG. 17(*a*).

When selected from FIG. 14, the Summary of Resident's Core Competencies report 360 initiates functionality for generating a detailed summary report of an individual residents performance in Core and Secondary competencies. To provide this report, a web-based communication such as the Summary of Resident's Core Competencies evaluation report interface 363 shown in FIG. 20 is provided. As shown in FIG. 20, for generating this report, there are four selection criteria including: 1) entry fields 364 enabling the entry of a start and end date range; 2) a pull-down menu 365 for enabling the selection of a Resident chosen from a list of all residents; 3) a pull-down menu 366 for enabling the selection of a Competency from a drop-down list 367 of competencies. This may include selection of "All Competencies" to generate data on all competencies reported on the selected resident including the percent performance in each competency followed by data comparisons to the Group (other residents in the same PGY) and the Total (all residents in the Program), or selection of an individual competency to generate detailed data on the selected competency, including a comparison to the Group and Total; and, 4) selecting the type of Evaluation including a radio button option 368a, for selecting "All Results" (default) to include all the reported data for the selected resident including results from evaluations completed voluntarily and those assigned by the Program, for example; and a radio button option 368b for selecting an "Assigned Results" to include on data from assigned evaluations. This option excludes results from evaluations completed voluntarily.

When selected from FIG. 14, the Overdue Evaluations report 370 initiates functionality for generating a detailed report of all evaluations overdue. In the preferred embodiment, as shown in FIG. 21(*a*), this report 372 is automatically generated and has no selection criteria. Particularly, the overdue evaluations reports provides an alphabetical list of each resident 373, their pager number 374, the names 375 and period 376 of each overdue evaluation 377, and the total number of days overdue 378. This report is specifically utilized to enable contact of each resident directly (e.g., by pager) in order to encourage the completion of overdue evaluations. FIG. 21*b*) illustrates an example e-mail communication 59 sent to an evaluator assigned an evaluation 379 currently due or overdue, depending upon its status. This status determination and automatic e-mail generation may be periodically performed in accordance with the executing overdue evaluation scan module 28 in FIG. 1.

Figure 22A:
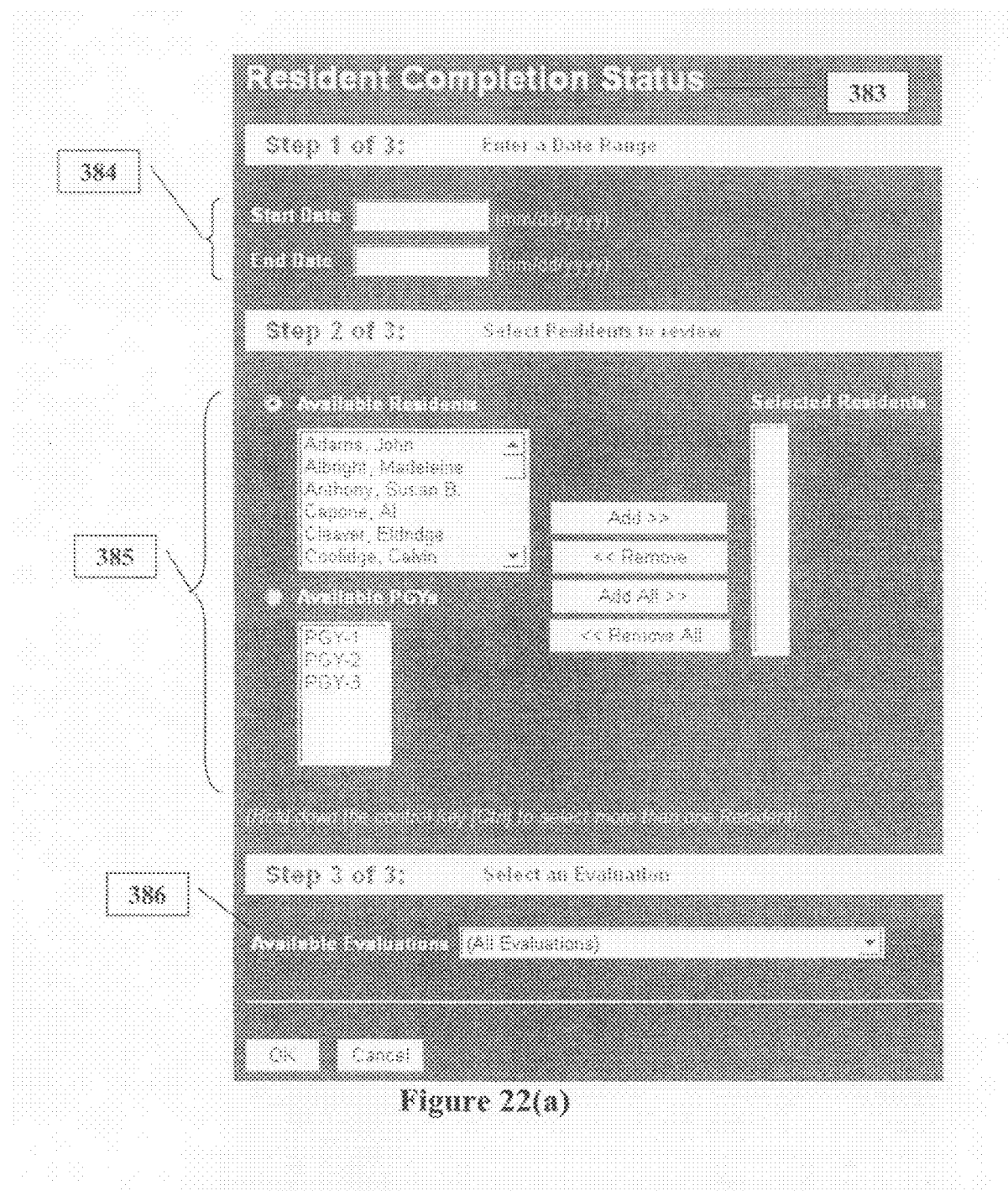
FIG. 22(a) illustrates an example Resident Completion Status report interface 383 providing functionality for on-line generation of a Resident Completion Status report 381 an example of which is depicted in FIG. 22(b)
Figure 22B:
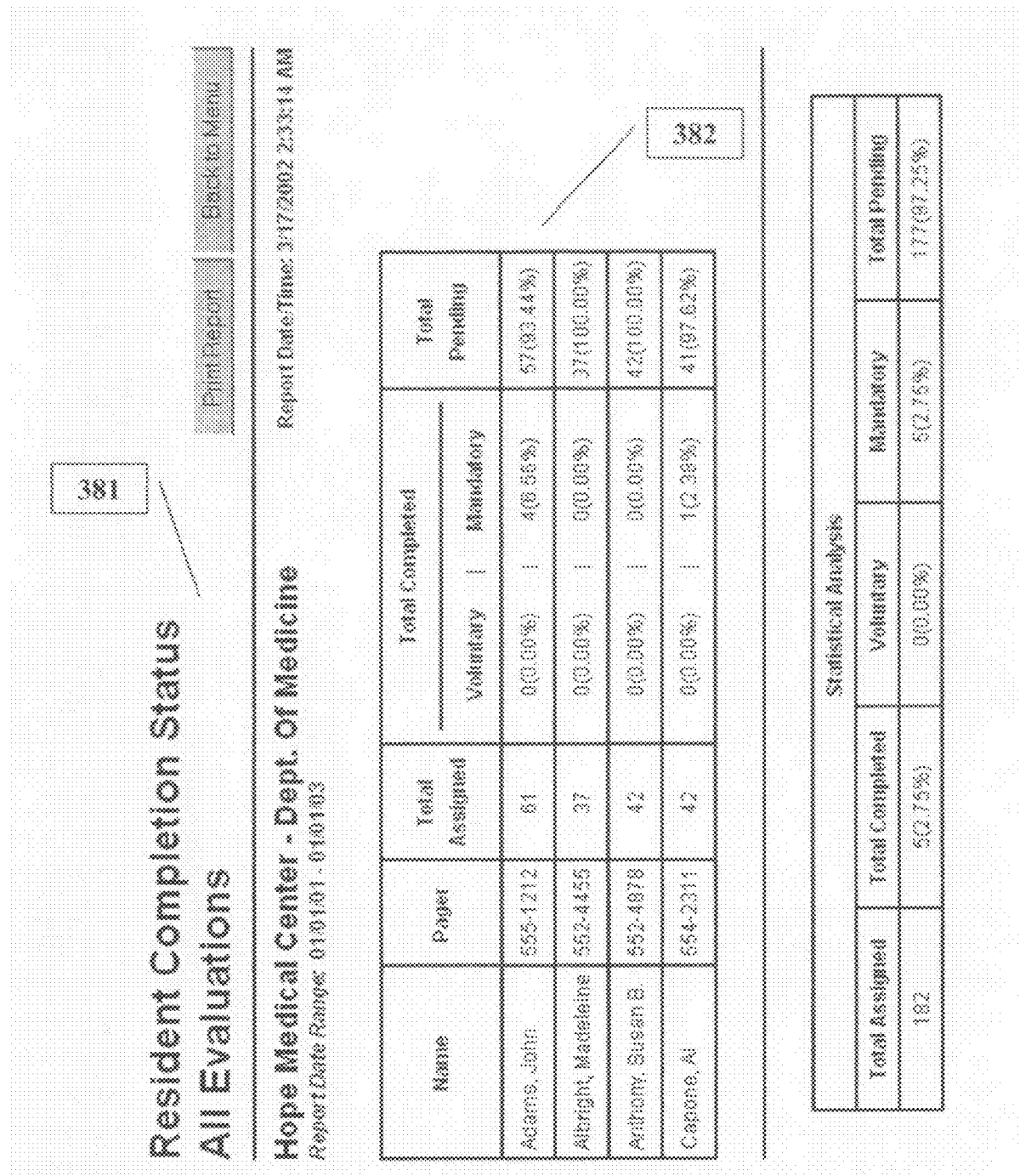
Figure 23A:
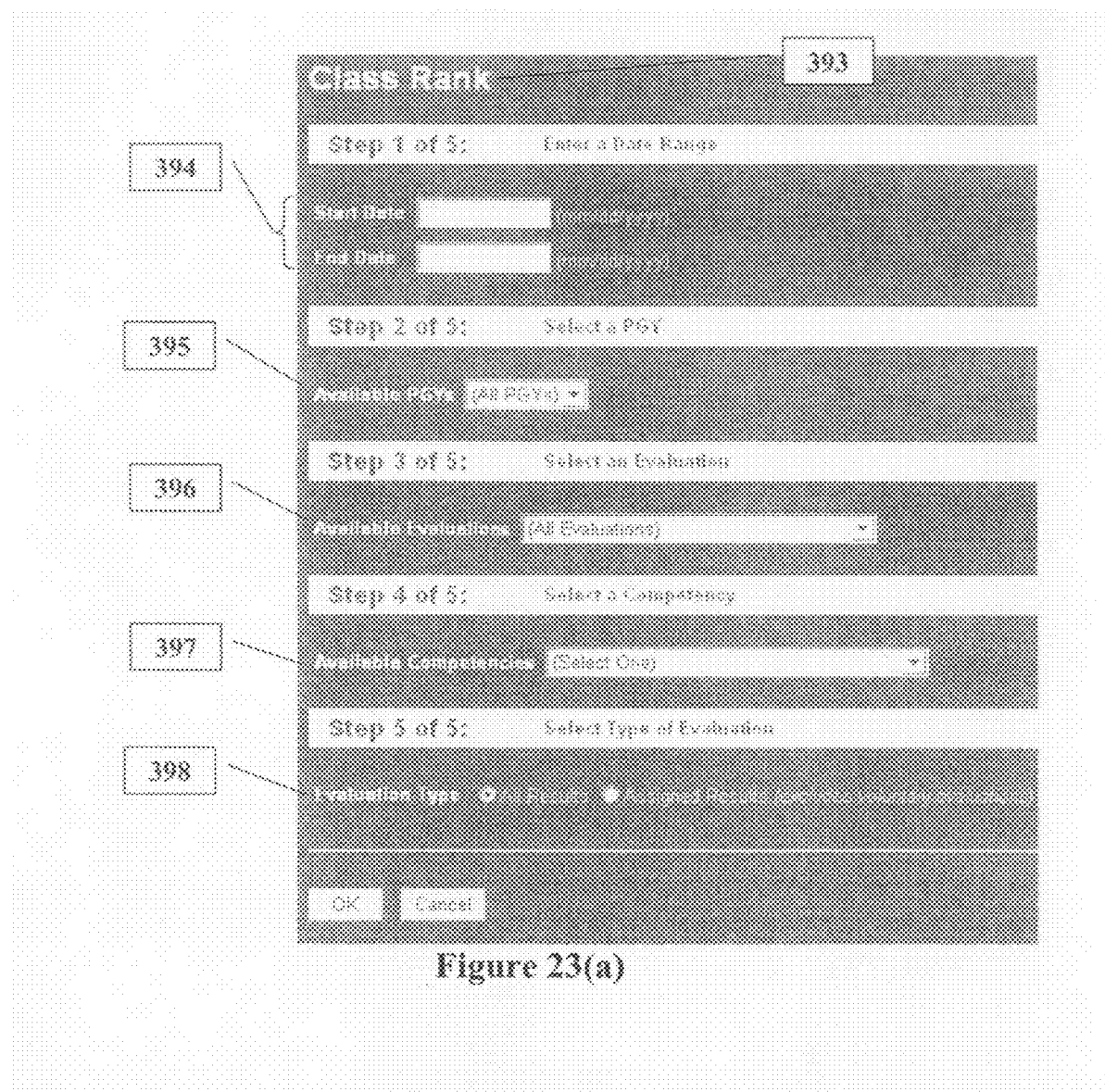
FIG. 23(a) illustrates an example Class Rank report interface 393 providing functionality for on-line generation of a Class Rank report 391 an example of which is depicted in FIG. 23(b)

When selected from FIG. 14, the Completion Status report 380 initiates functionality for generating a detailed summary report 381, such as shown in FIG. 22(*b*), providing data 382 indicating the total number of evaluations assigned, completed and pending for each resident, and for enabling a review of the Completion Status of an individual resident or all residents in the program To provide this functionality, a web-based communication such as the Completion Status report interface 383 shown in FIG. 22(*a*) is provided. As shown in FIG. 22(*a*), for generating this report, there are four selection criteria including: 1) entry fields 384 enabling the entry of a start and end date range; 2) a mechanism 385 for selecting residents to review including Add, Add All, Remove, Remove All functionality for choosing residents as described herein, particularly by selection of a name, for example, from the list of Available Residents or selecting residents based on PGY level, by pointing and clicking on a desired name(s) or PGYs and then selecting "Add>>" button to select the name(s); or, selecting all residents names from the list of Available Residents by clicking the "Add All>>" to select all the names. Further functionality for removing some or all of the selected residents names is provided; and, 3) a pull-down menu 386 for enabling the selection of an Evaluation, e.g., by choosing one evaluation from the list of all evaluations When selected from FIG. 14, the Class Rank report 390 initiates functionality for generating a detailed summary report 391, such as shown in FIG. 23(*b*), providing data 392 pertaining to the ranking of residents by percent performance in a selected competency. Further options for enabling the choice to review ranking of a single competency across "All Evaluations", or to review a cross-comparative report of multiple competencies within a single evaluation, is provided. A cross-comparative report is a ranking of residents by a single competency within a single evaluation. This ranking is further enhanced by comparing data from other competencies, and listing it next to the ranking data. This facilitates the cross-comparison of performance in one competency with respect to other competencies (within the same evaluation). To provide this functionality, a web-based communication such as the Class Rank report interface 393 shown in FIG. 23(a) is provided. As shown in FIG. 23(a), for generating this report, there are four selection criteria including: 1) entry fields 394 enabling the entry of a start and end date range; 2) a mechanism 395 for selecting available PGYs by enabling choice of a specific PGY in order to include all residents from a given class; 3) a pull-down menu 396 for enabling the selection of an Evaluation, e.g., by choosing an individual evaluation from the list of all evaluations, or choosing "All Evaluations". This option to enables review of ranking across all evaluation types, or review a cross-comparative report within a single evaluation. That is, to generate a cross-comparative report, the user must choose a specific evaluation in this step so that data will be automatically updated in the next step 4) to include competencies related to the specific evaluation; 4) a pull-down menu 397 for enabling the selection of a competency. Preferably, the competencies listed in this pull-down menu 397 will depend on the evaluation selection type from the previous step. That is, as maintained in the system databases (FIG. 1), competencies are associated with a particular evaluation type/audience. For example, when "All Evaluations" is selected in the prior step 3), the user is presented with a list of competencies included in the chosen evaluation. When a specific evaluation is selected in the prior step 3) the user is presented with a list of competencies included in the chosen evaluation. A single competency is chosen for ranking residents. In the report, the first ranking column lists the chosen competency, followed by the percent performance in each subsequent competency (included in the chosen evaluation). Finally, in step 5), the type of Evaluation is selected from among the "All Results" (default) or "Assigned Results" options 398 as described herein.

Figure 24A:
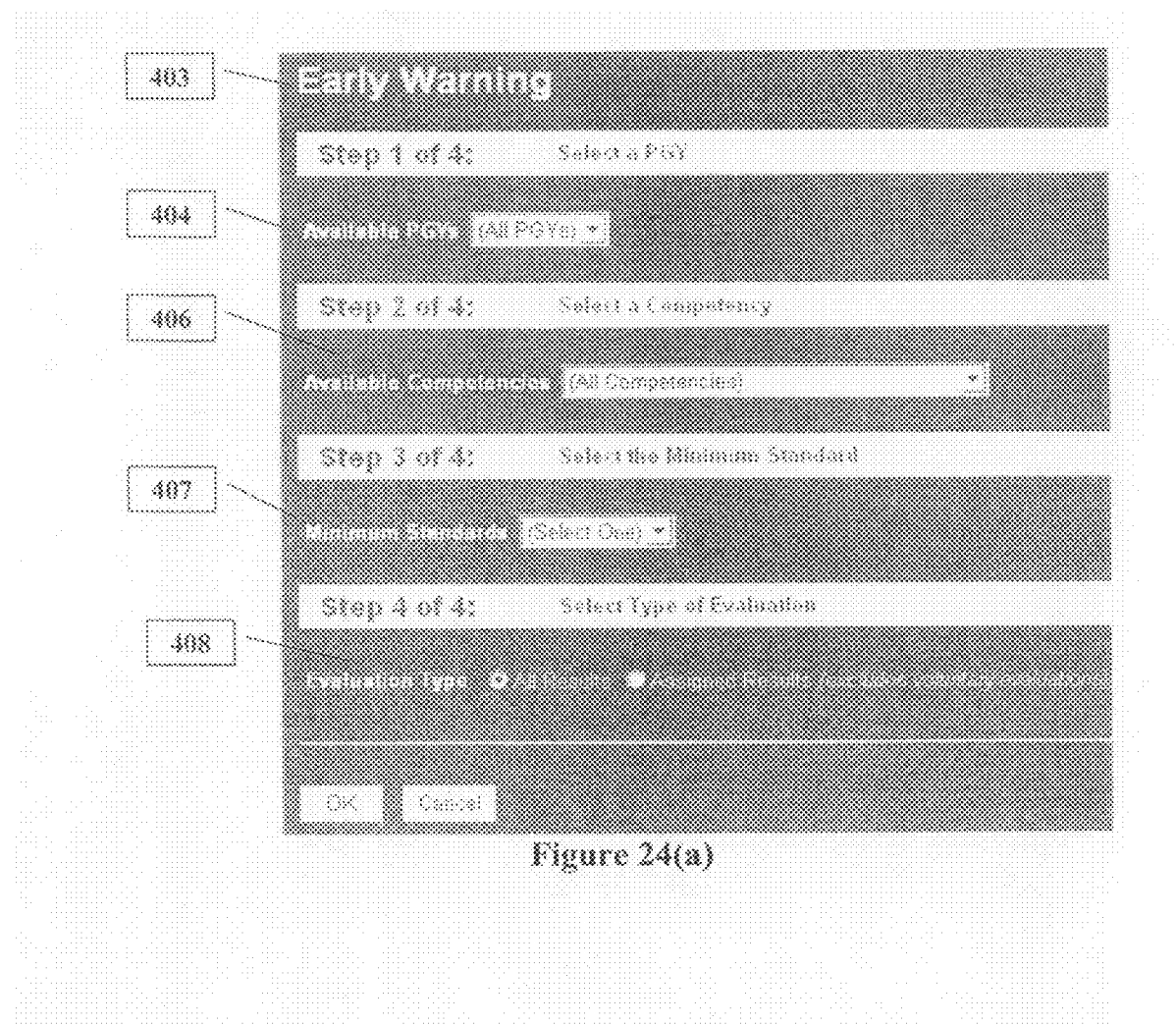
FIG. 24(a) illustrates an example Early Warning report interface 403 providing functionality for on-line generation of an Early Warning report 401 an example of which is depicted in FIG. 24(b)
Figure 24B:
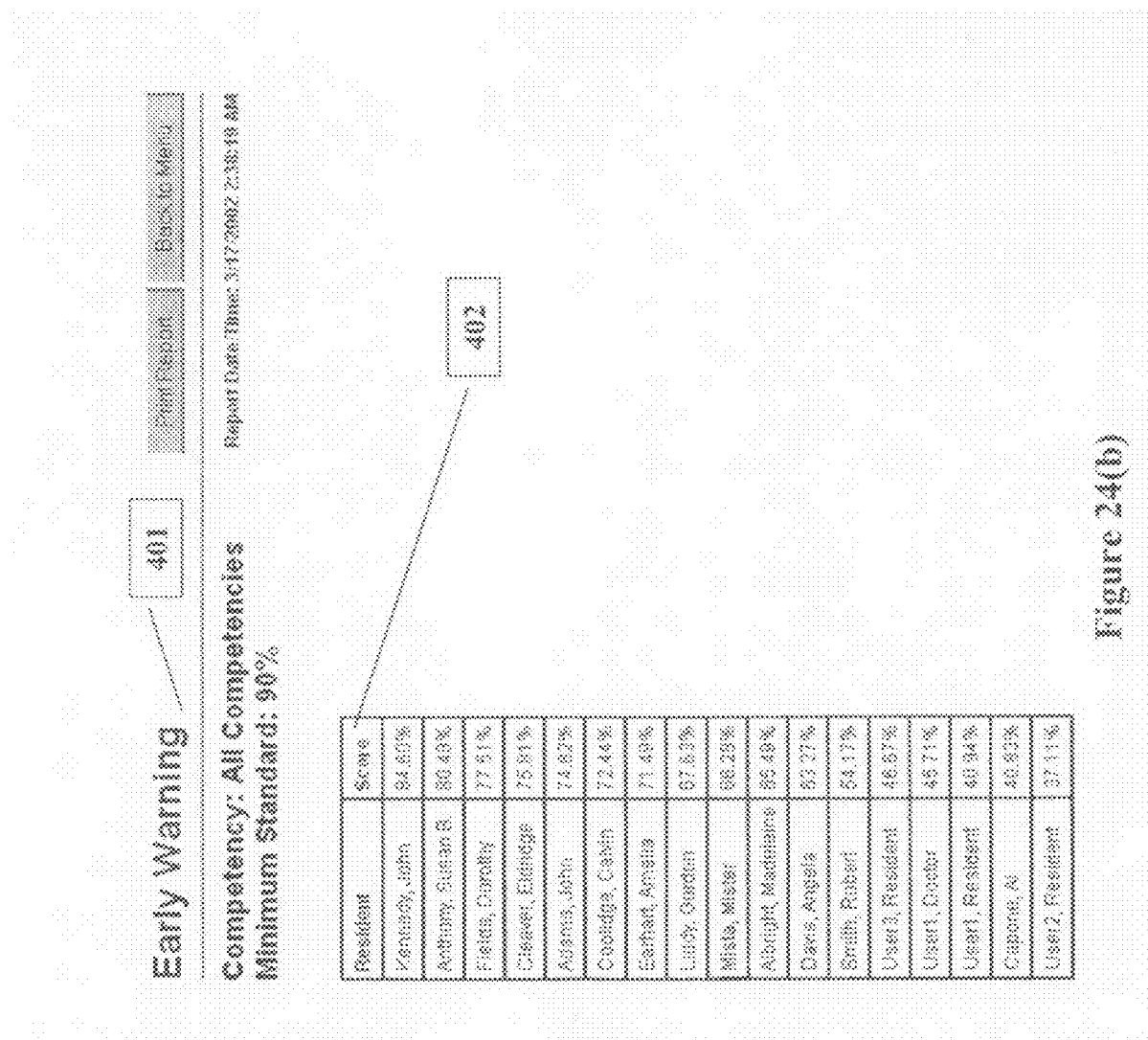

When selected from FIG. 14, the Early Warning report 400 initiates functionality for generating a detailed summary report 401, as shown in FIG. 24(b), of all residents' performance (e.g., score 402) with respect to a minimum standard. For example, performance may be measured across all evaluations and may include "All Competencies" or a single competency. This report may be advantageously used to quickly uncover residents who may be performing below a minimum standard, and may need interventional support. To provide this functionality, a web-based communication such as the Early Warning report interface 403 shown in FIG. 24(a) is provided. As shown in FIG. 24(a), for generating this report, there are four selection criteria including: 1) entry fields 404 enabling the selection of a specific PGY in order to restrict the search to one group or, "All PGYs" in order to include all residents; 2) a pull-down menu 406 for enabling the selection of a competency for basing a minimum performance standard. Preferably, there are two options: an "All Competencies" option for generating data on all competencies reported on the selected resident with the results reported in a summary format; or, a specific competency selected from all available competencies, wherein the results are cumulative and only in reference to the selected evaluation; 3) a pull-down menu 407 for selecting a Minimum Standard for evaluating the residents' performance. The minimum standard is a percent value. Any resident performing less than the minimum will be included in the Early Warning Report; and, 4) the selection options 408 for the type of Evaluation including the "All Results" (default) option or "Assigned Results" option as described herein.

Figure 25A:
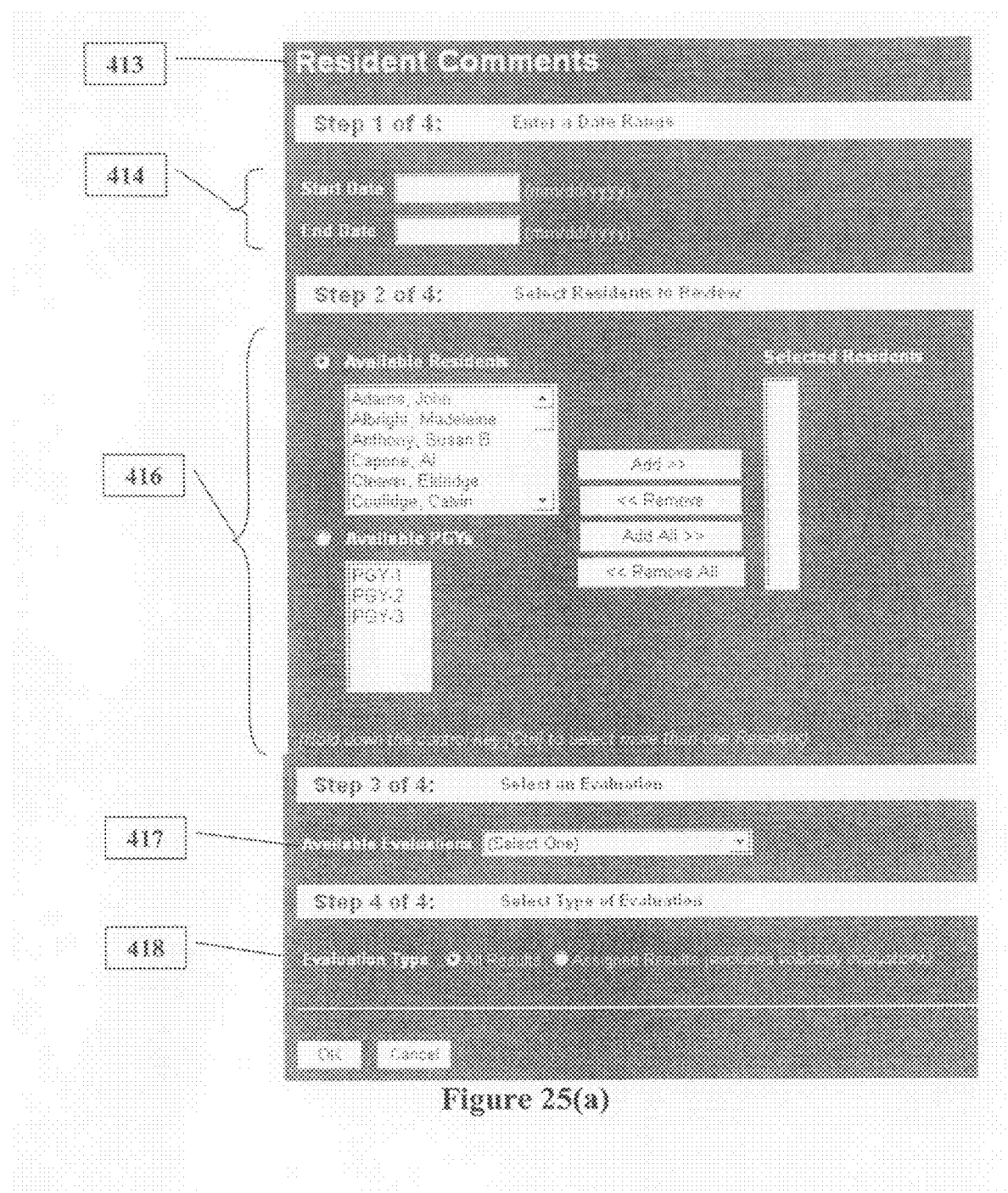
FIG. 25(a) illustrates an example Resident Comments report interface 413 providing functionality for on-line generation of a Resident Comments report 411 an example of which is depicted in FIG. 25(b)
Figure 25B:
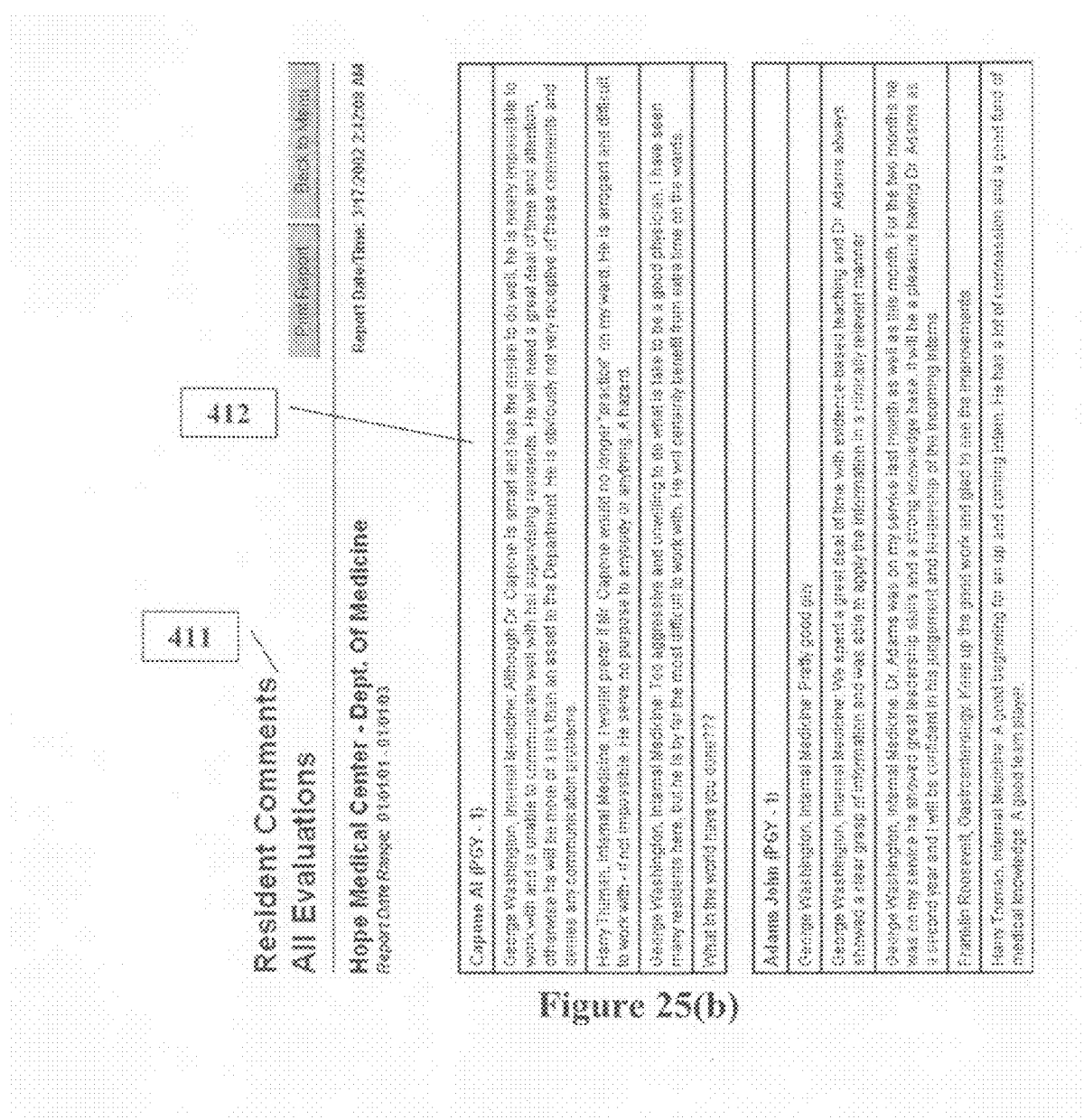

When selected from FIG. 14, the Resident Comments report 410 initiates functionality for generating a detailed summary report 411, as shown in FIG. 25(b), of comments 412 written by attending physicians on selected residents, for example. Preferably, each attending comment includes the name and specialty of the authoring attending physician. To provide this functionality, a web-based communication such as the Resident Comments report interface 413 shown in FIG. 25(a) is provided, As shown in FIG. 25(a), for generating this report, there are four selection criteria including: 1) entry fields 414 enabling the selection of a start and end date range; 2) a mechanism 416 for selecting residents to review including Add, Add All, Remove, Remove All functionality for choosing residents as described herein, particularly by selection of a name, for example, from the list of Available Residents or selecting residents based on PGY level by pointing and clicking on a desired name(s) or PGYs; 3) the pull-down menu 417 for selecting an evaluation, e.g., by choosing either the "All Evaluations" or an individual evaluation. This option is used to review the comments written on a specific evaluation, or on all evaluations; and 4) button options 418 enabling the selection of the type of Evaluation from among the "All Results" (default) option or "Assigned Results" option as described herein.

It should be understood that the report generation module 27 (FIG. 1) provided herein additionally is used to generate the following Attending Evaluation reports selectable from the menu list 304b of FIG. 14 including: Individual Attending Evaluations 420; Summary of Attending Evaluations 425; Summary Peer-to-Peer Evaluations 430; Summary Program Evaluations 435; Trending of Attending Performance 440, Summary of Attending's Core Competencies 445; Overdue Evaluations 450; Completion Status 455; Class Rank 460; and, Attending Comments 465. It is understood that these Attending reports are generated in a manner largely identical to the manner in which their counterpart Resident Evaluation reports are generated.

Procedure Tracking

Figure 26:
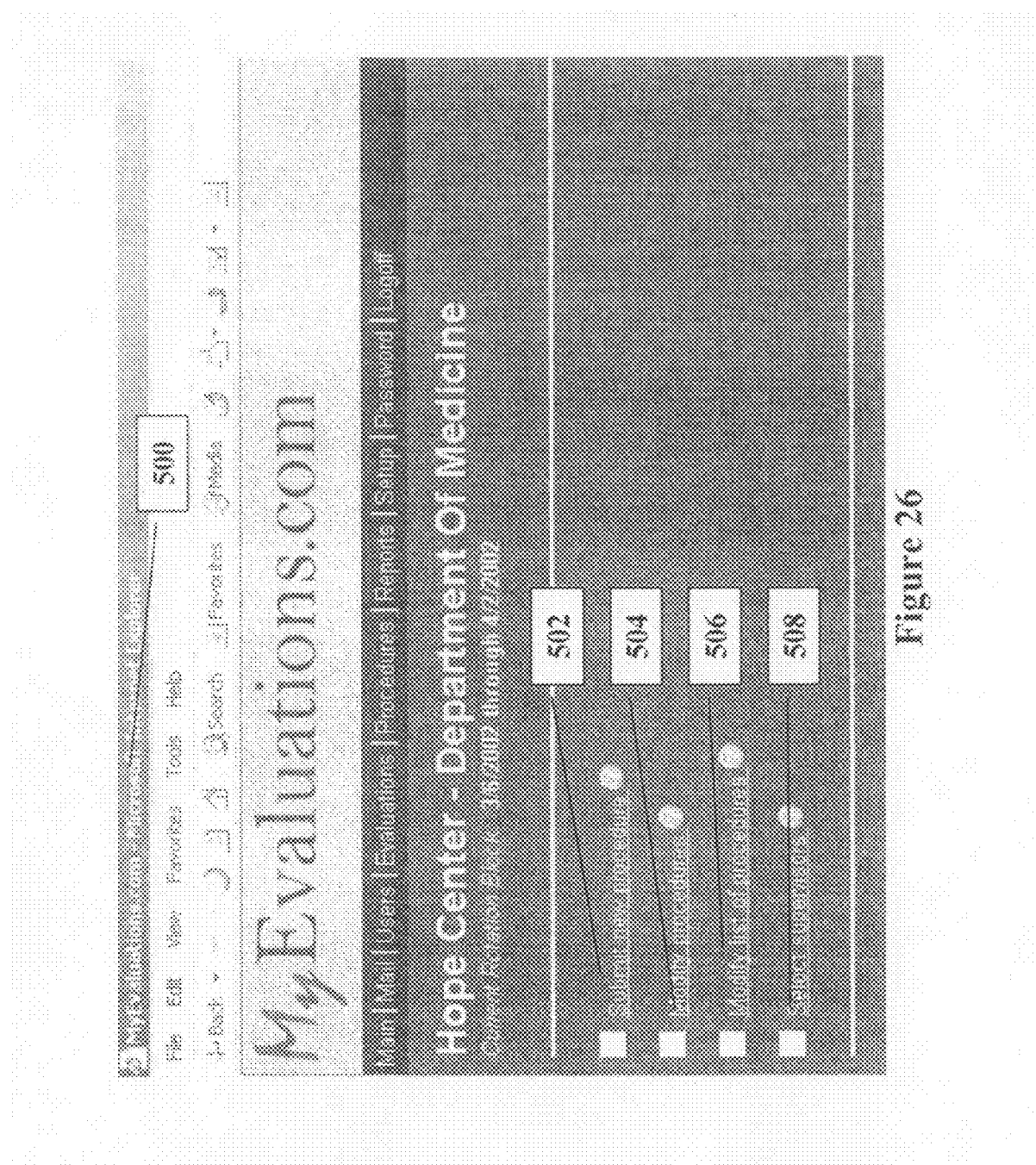
FIG. 26 illustrates an example Procedures Menu Interface 500 for enabling the generation, management and tracking of procedures.

Referring back to FIG. 3(b), there is provided a "Procedures" option 64, the selection of which initiates download of a web-based communication providing a Procedures Menu Interface such as shown in the example Procedures Menu Interface 500 of FIG. 26. As shown in FIG. 26, the web-based interface 500 provides each user with a sub-menu of options that facilitates the on-line collection of all data pertaining to procedures completed by residents and medical students. This functionality is performed by the procedure build and tracking execution threads 25 as shown in FIG. 1. For a user/administrator, these selection options include an option 502 for submitting a new or completed procedure on-line; an option 504 for modifying submitted procedures; an option 506 for modifying the database of available procedure types and enabling design of a procedure; and, an option 508 for selecting a supervisor(s), i.e., identifying attendings qualified as supervisors.

Submit New Procedures

Figure 27:
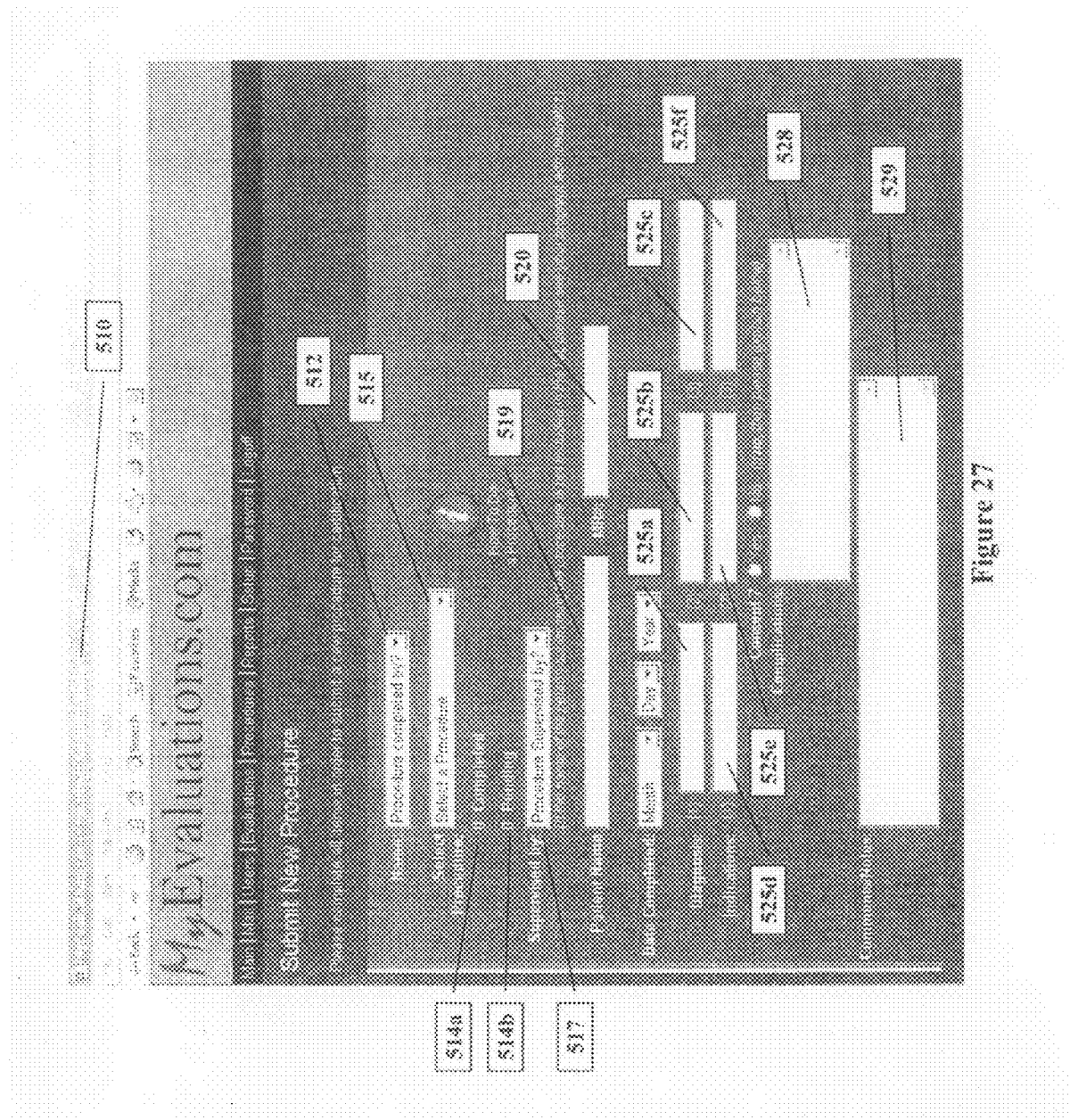
FIG. 27 illustrates an example interface 510 for enabling a user/administrator to add a new completed procedure on-line.

The person completing the procedure logs in to MYEVALUATIONS.COM® and selects a procedure to mark as completed. When selected from the Procedures Menu Interface 500 of FIG. 26, the option 502 for submitting new procedures initiates downloading of a web-based communication providing the submit new procedure interface 510 such as the example interface provided in FIG. 27. It is from this interface 510 of FIG. 27 that enables a user to add a new completed procedure on-line. Based on the Attending identified as qualified to certify procedures, the system presents the user with the names of persons qualified to certify the completed procedure. The user then completes all the details of the procedure by entering the information as specified in the entry fields provided via the interface 510. Then the user submits the completed form via a secure Internet connection for storage in the procedures database 34. Once submitted, the person selected as the certifying individual will receive a message in the MYEVALUATIONS.COM® mailbox, which message provides the certifier with the option to Accept or Reject the procedure completion form. If Accepted, the user receives credit for completing the procedure. More particularly, with reference to FIG. 27, the user enters the following information: a Name field 512 for entering the name of the person performing the procedure. For users such as residents and medical students, the name field will display the First name and Last name. It is a fixed field based on the user login information. For users such as administrators, the name field comprises a drop-down menu option including the names of all residents and medical students with the name displayed as Last name, First name; a Select procedure field 514 which provides a pull-down menu 515 displaying procedure names available for certification. This field will only display procedures marked as "Included" in the procedure database. For a resident, after logging in, only procedures marked as "Yes" in an Inc-Residents field (not shown) will be displayed. When a medical student logs-in, only procedures marked as "Yes" in the Inc-Med_Stu field will be displayed. The Completed field 514 is provided to display the total number of completed procedures 514a, i.e., a count for the selected individual with reference to the selected procedure. A pending field 514b displays a number result of pending procedures, i.e., the number of required procedures minus the number of Completed procedures ((Required)-(Completed)); If the number of completed is greater than the number required, then this value will be set to zero. An option 516 is additionally provided via interface 510 that provides details about how to perform the selected procedure. The "Supervised by" field 517 displays the names of the Supervisors. Persons qualified to be supervisors include: Certified Residents and Attendings selected as supervisors. Certified Residents are residents who complete the number of procedures required to be certified and the Procedures Database will include a certification number for those certified residents maintained in the "Supervised by" field. For Attendings, a separate module for Attendings may be added or removed from this list; see "Select Supervisors". Further included is a Patient name entry field 519 which receives a plurality of character spaces for free-form entry of the patients name. An MR# text entry field 520 is additionally provided for receiving alpha-numeric characters for free-form entry of the patients medical record number. The date completed field 524 is additionally provided which comprise drop-down fields for selecting the month, day and year, respectively. As further shown in the submit new procedure interface 510 of FIG. 27, individual text fields 525a-525c are provided for free-form entry of a patient's diagnosis. Furthermore, individual text fields 525d-525f fields are provided for free-form entry of indications to do the procedure. Furthermore, Yes/No radio buttons 527 are provided for verifying whether consent was required to do the procedure. Further, a Complications Note field 528 is provided for free-form entry of any complication associated with the procedure. A Comments/Notes field 529 are additionally provided for free-form entry of any comments. After entry of each of the required fields, the user may then Submit the procedure information by selecting a displayed submit icon. This will function similarly to an evaluation submission and is stored in the procedures database 34 of FIG. 1. The Supervising Resident or Attending will receive an assignment in the section Evaluation/Procedures to be Acknowledged. The supervisor then has the option to modify or, to Approve or Reject the completion of the procedure. Once Approved, the resident or medical student will receive credit for the procedure as completed. It should be understood that Evaluation questions are optionally included. From the "Select Procedure-Eval Questions" menu option the administrator may select standard evaluation questions that will be included in the procedure survey. It should be understood that users will have access to the following other Procedure Sub-Menu options: including an option (not shown) for viewing a detailed history of procedures; and, an option for viewing a Summary of completed reports.

Figure 28:
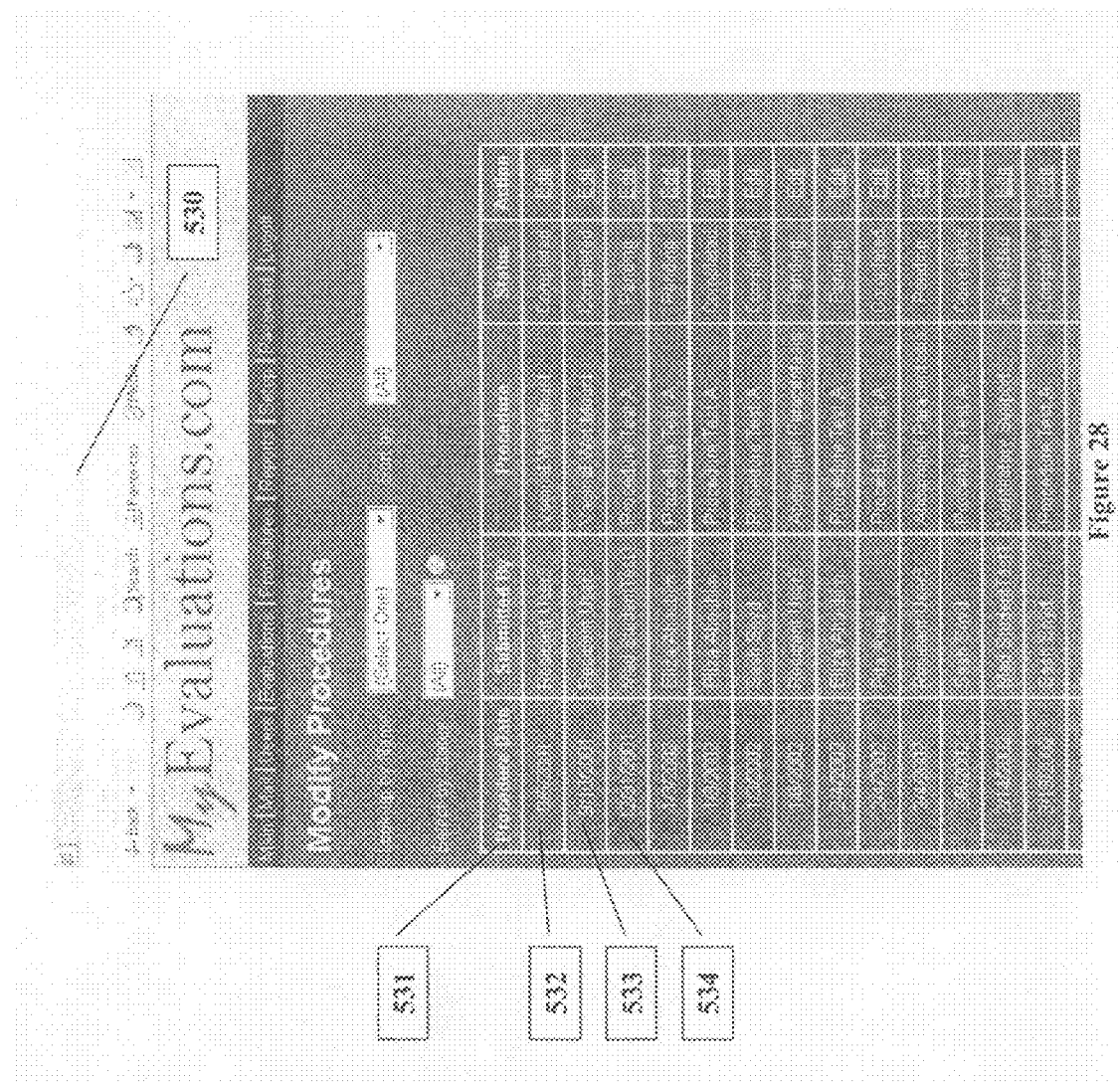
FIG. 28 illustrates an example web-based communication providing an interface 530 for modifying submitted procedures.

When selected from FIG. 26, the option 504 for modifying submitted procedures initiates functionality for generating a detailed summary, as shown in the example web-based communication 530 such as shown in FIG. 28, providing a list of selected medical students/residents submitters 531, their associated submitted procedures in column 532, and the status of the procedures 533. Any action that is required for the procedure may be edited by selecting an edit action 534 next to the selected procedure which returns the user/administrator to the submit new procedure screen (FIG. 27) for modifying/editing the data entered.

Figure 29:
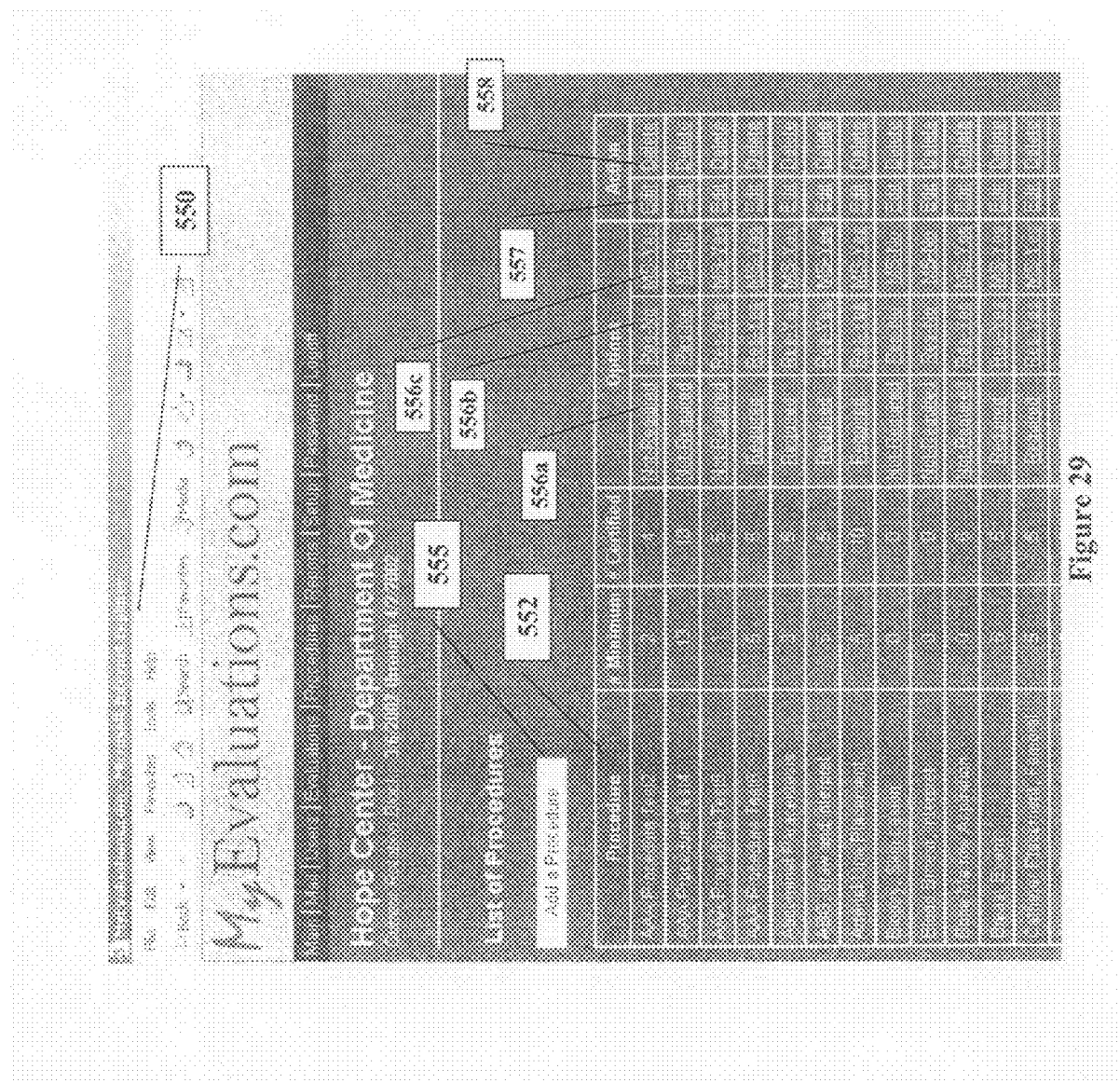
FIG. 29 illustrates an example web-based communication providing an interface 550 for generating a detailed list of all procedures and functionality for initiating addition of new procedures.

It should be understood that functionality is provided for designing a procedure. That is, when selected from FIG. 26, the option 506 for modifying submitted procedures initiates functionality for generating a detailed list of all procedures 552, as shown in the example web-based communication 550 such as shown in FIG. 29. For each procedure, certain criteria may be modified. For example, by user selection of the option required field 556a will initiate toggling of that particular procedure as being required/non-required. Likewise, user selection of the option resident field 556b will initiate toggling of that particular procedure as being required for a resident or not. Similarly, user selection of the option medical student field 556c will initiate toggling of that particular procedure as being required for a medical student or not. Further action 557 may be taken to edit that particular procedure, for example, changing the procedure's name, changing the minimum number of procedures required to be performed for graduation or the certification, or by changing that procedures requirement as being available to residents, medical students or, both. Further functionality 558 is provided to delete that particular procedure from the list of procedures 552.

Figure 30:
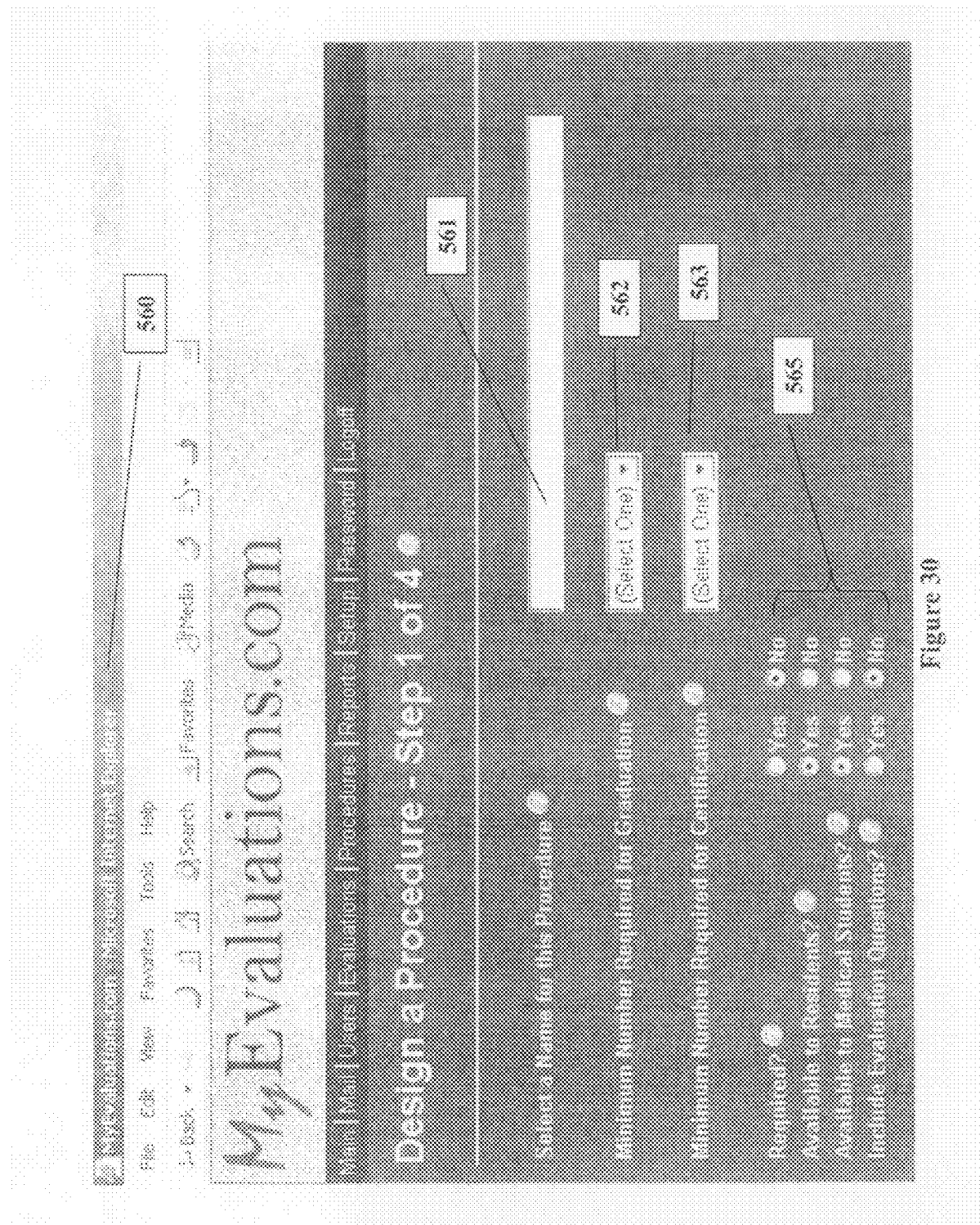
FIG. 30 illustrates an example web-based communication providing an interface 560 for designing a new procedure; and, FIG. 31 illustrates the example web-based communication providing an interface 570 for selecting an attending who is to supervise the procedure.

Further with respect to FIG. 29, a button option 555 is provided for designing a procedure and adding it to the procedures database 34 of FIG. 1. Selection of option 555 particularly initiates generation of a Design a Procedure screen display 560 such as the example display shown in FIG. 30. From this display 560, an administrator may perform the following functions: enter a new procedure's name in entry field 561; entering the minimum number of procedures required to be performed for graduation 562 or the certification 563, or radio button selection options 565 specifying whether the new procedure is to be available to residents, medical students or, both.

Figure 31:
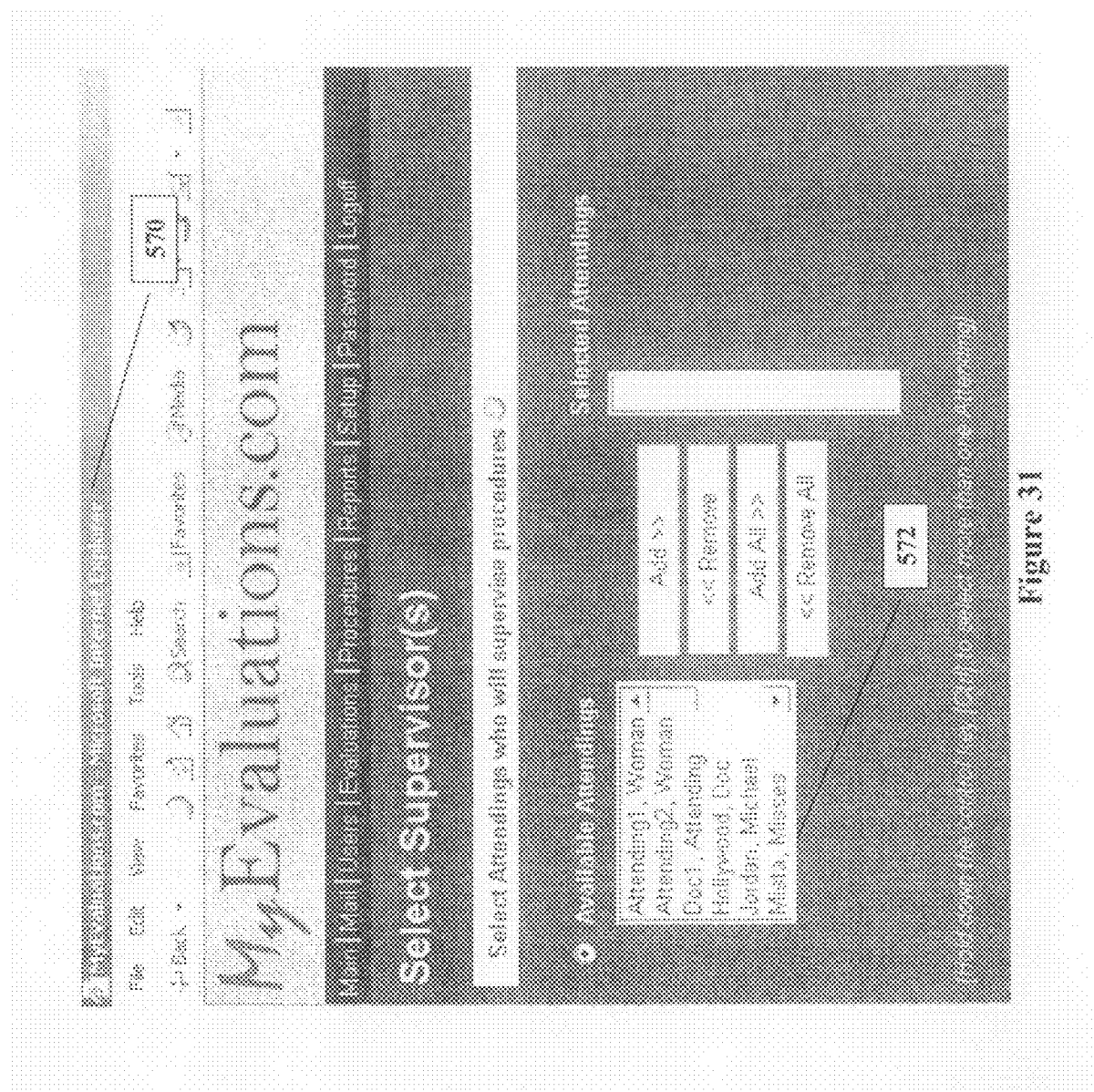

Referring back to FIG. 8, there is provided the selection option 508 for selecting a supervisor(s), i.e., identifying attendings qualified as supervisors. FIG. 31 illustrates the example web-based communication providing an interface 570 for selecting an attending who is to supervise the procedure. As shown in FIG. 31, functionality 572 is provided to enable selection of attendings to review including mechanisms for Adding, Adding All, Removing, and Removing All available attendings, as described herein, particularly by selection of a name, for example, from the list of Available Attendings and then selecting "Add>>" button to select the name(s); or, selecting all residents names from the list of Available Residents by clicking the "Add All>>" to select all the names. Further functionality for removing some or all of the selected attendings names is provided.

While the invention has been particularly shown and described with respect to illustrative and preformed embodiments thereof, it will be understood by those skilled in the art that the foregoing and other changes in form and details may be made therein without departing from the spirit and scope of the invention which should be limited only by the scope of the appended claims.

Having thus described our invention, what we claim as new, and desire to secure by Letters Patent is:

1. A program storage device readable by machine, tangibly embodying a program of instructions executable by the machine to perform method steps for a method for facilitating generation and performance of on-line evaluations for one or more individuals to evaluate one or more other individuals of an academic hospital, said method steps comprising:

providing a database accessible by a computer device;

providing to said database information comprising profiles of individuals associated with said hospital, said profiles of individuals including: a user name, a user type, a start date of that user at said hospital, a department of said hospital within which individual is associated; an individual's rotation schedule organized as predetermined time intervals within which an individuals of certain user types are assigned tasks to perform at said hospital; and, a minimum number of evaluations to be completed by said individual within a predetermined time interval; and, assigning evaluations to be completed by one or more individuals selected according to said one or more of: user name, user type, or start date of that user; and, scheduling evaluation assignments to said one or more individuals by a date range commensurate with said predetermined time interval of said rotation schedule, an assigned individual accessing, via a computer device, said assigned evaluation on-line for completion thereof; and, tracking, via a computer device, data comprising a number of pending evaluations assigned to an individual per said date range, and completed by said individual per said date range, and storing said tracked data;

periodically scanning said tracked data computer and obtaining a number of pending evaluations to be completed by an individual within each scheduled date range, said number of pending evaluations comprising overdue evaluations or partially completed evaluations, and, for each assigned evaluation overdue, automatically calculating a number of days beyond said scheduled date range that said assigned evaluation is overdue and, for each assigned evaluation not yet completed within said date range, automatically calculating a remaining number of days within said date range that said individual can complete said assigned evaluation; and, automatically generating for an individual a list of said overdue evaluations including, for each, said number of days overdue and a list of said partially completed evaluations per scheduled date range, including, said remaining number of days within per scheduled date range with which to complete an evaluation; and, automatically notifying said individual with said list of overdue evaluations or partially completed evaluations to ensure increased compliance in performing said evaluations within said academic hospital.

2. A program storage device readable by machine, tangibly embodying a program of instructions executable by the machine to perform method steps for a method of facilitating generation and performance of on-line evaluations for at least one first individual of an academic hospital to evaluate at least one second individual of an academic hospital, said method steps comprising:

providing a database accessible by a computer device, said database including profile information of said first individual and said second individual, said profile information including at least one of:

a name of said individual, a department of said hospital with which said individual is associated, an employment position with which said individual is associated, and at least one predetermined time interval, and at least one evaluation having a due date;

assigning said at least one evaluation to said first individual based on said profile information of said first individual and said profile information of said second individual, said assigned evaluation accessible by said first individual, via said computer device, for the on-line completion thereof;

periodically determining whether said assigned evaluation is complete or incomplete, and whether said due date is expired;

when said evaluation is incomplete and said due date is not expired, calculating a remaining number days until said due date;

when said evaluation is incomplete and said due date is expired, calculating a number of days since said due date has expired;

generating a list of incomplete evaluations, said list associating with each of said incomplete evaluations with at least one of: said remaining number of days until said due date, when said due date has not expired, and said number of days since said due date has expired, when said due date has expired; and providing said list to said first individual; and wherein said evaluation is assigned based on the at least one predetermined time interval of said first individual at least partially overlapping the at least one predetermined time interval of said second individual.

3. The method of claim 2, wherein said predetermined time interval comprises a time interval during which said first individual is associated with said second individual.

4. The method of claim 2, wherein the department of said hospital with which said first individual and said second individual are associated is the same department, and wherein the predetermined time interval comprises a time interval during which said first individual and said second individual are associated with the department.

5. The method of claim 2, wherein the employment position with which said first individual and said second individual are associated is the same employment position, and wherein the predetermined time interval comprises a time interval during which said first individual and said second individual are associated with the employment position.

6. The method of claim 2, wherein the predetermined time interval comprises a time interval during which said individual is associated with an assignment and wherein said assignment of said first individual is the same assignment of said second individual.

7. The method of claim 2, wherein the predetermined time interval comprises a time interval during which the individual is associated with the hospital.

8. The method of claim 2, further comprising the step of:

selecting a plurality of evaluation questions, said evaluation generated from said evaluation questions; and storing said evaluation in said database.

9. The method of claim 8, wherein at least one of said selected evaluation questions is selected from said database.

10. The method of claim 9, wherein said evaluation questions are selectable according to said profile information of said first individual and said second individual.

11. The method of claim 9, wherein said evaluation questions are selectable according to at least one of: an evaluator type, an evaluatee type, and a competency type.

12. The method of claim 8, wherein at least one of said selected evaluation questions is a customized field-entry-type evaluation question.

* * * * *

UNITED STATES PATENT AND TRADEMARK OFFICE
CERTIFICATE OF CORRECTION

PATENT NO. : 7,899,702 B2  
APPLICATION NO. : 11/933979  
DATED : March 1, 2011  
INVENTOR(S) : David P. Melamed Page 1 of 1

It is certified that error appears in the above-identified patent and that said Letters Patent is hereby corrected as shown below:

Title Page

Item (76) Inventors: David P. Melamed, New York, NY (US)

~~Morris Nejat, Short Hills, NJ (US)~~

Signed and Sealed this

Twenty-eighth Day of June, 2011

David J. Kappos
*Director of the United States Patent and Trademark Office*